(12) United States Patent
Bissantz et al.

(10) Patent No.: US 8,404,679 B2
(45) Date of Patent: Mar. 26, 2013

(54) PYRROLIDINE DERIVATIVES AS NK2 RECEPTOR ANTAGONISTS

(75) Inventors: Caterina Bissantz, Village-Neuf (FR); Philippe Jablonski, Steinbrunn-le-Haut (FR); Henner Knust, Rheinfelden (DE); Andreas Koblet, Bottmingen (CH); Anja Limberg, Basel (CH); Matthias Nettekoven, Grenzach-Wyhlen (DE); Hasane Ratni, Habsheim (FR); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/452,981

(22) Filed: Apr. 23, 2012

(65) Prior Publication Data

US 2012/0208803 A1 Aug. 16, 2012

Related U.S. Application Data

(63) Continuation of application No. 12/482,490, filed on Jun. 11, 2009, now abandoned.

(30) Foreign Application Priority Data

Jun. 16, 2008 (EP) ................................. 08158326

(51) Int. Cl.
| | |
|---|---|
| A61K 31/496 | (2006.01) |
| A61K 31/498 | (2006.01) |
| A61K 31/5377 | (2006.01) |
| A61K 31/541 | (2006.01) |
| C07D 207/14 | (2006.01) |
| C07D 403/12 | (2006.01) |
| C07D 405/12 | (2006.01) |
| C07D 405/14 | (2006.01) |
| C07D 417/06 | (2006.01) |
| A61K 31/454 | (2006.01) |
| A61K 31/501 | (2006.01) |
| C07D 401/06 | (2006.01) |
| C07D 401/14 | (2006.01) |
| C07D 403/06 | (2006.01) |
| C07D 405/06 | (2006.01) |

(52) U.S. Cl. ............... 514/227.8; 514/232.2; 514/249; 514/254.01; 544/58.2; 544/141; 544/353; 544/372; 544/114; 544/124; 544/130; 544/238; 546/156; 546/194; 546/208; 546/279.1; 548/131; 548/364.1; 548/517; 548/525; 548/539

(58) Field of Classification Search .................. None
See application file for complete search history.

(56) References Cited

U.S. PATENT DOCUMENTS

| | | | |
|---|---|---|---|
| 4,826,858 A | 5/1989 | Bosies et al. | |
| 2009/0156572 A1* | 6/2009 | Ikeura et al. ............ | 514/210.02 |

FOREIGN PATENT DOCUMENTS

| | | |
|---|---|---|
| DE | 3446713 | 6/1986 |
| EP | 1705176 | 9/2006 |
| EP | 1975165 | 10/2008 |
| WO | 2001/060813 | 8/2001 |
| WO | 2005/032464 | 4/2005 |
| WO | 2009/072643 | 6/2011 |

OTHER PUBLICATIONS

Young et al., "Bioorganic & Medicinal Chem. Letters" 17:5310-5315 (2007).
Charpentier et al., "J. Med. Chem." 38(26):4993 (1995).

* cited by examiner

*Primary Examiner* — Emily Bernhardt
(74) *Attorney, Agent, or Firm* — George W. Johnston; Patricia S. Rocha-Tramaloni; Kimberly J. Prior

(57) ABSTRACT

The present invention relates to compounds of formula I

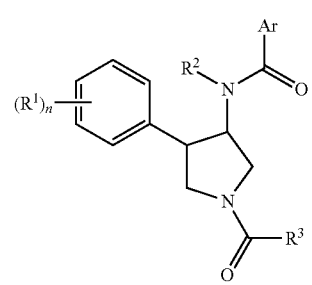

wherein $R^1$, $R^2$, $R^3$, Ar and n are as defined herein and pharmaceutically active salts, racemic mixtures, enantiomers, optical isomers or tautomeric forms thereof. The compounds can be used for the treatment of depression, anxiety or schizophrenia.

10 Claims, No Drawings

PYRROLIDINE DERIVATIVES AS NK2 RECEPTOR ANTAGONISTS

PRIORITY TO RELATED APPLICATION(S)

This application is a continuation of U.S. application Ser. No. 12/482,490, filed Jun. 11, 2009, now pending; which claims the benefit of European Patent Application No. 08158326.2, filed Jun. 16, 2008. The entire contents of the above-identified applications are hereby incorporated by reference.

BACKGROUND OF THE INVENTION

NK2 receptors are found in the periphery and the central nervous system. In the periphery, the NK2 receptor is mainly found in the smooth muscle of the gastrointestinal, respiratory and urinary tracts. In the central nervous system, the presence of NK2 binding sites in the rat brain has been demonstrated in the hippocampus, thalamus and the septum. The presence of NK2 binding sites in several limbic regions suggest that NK2 receptors may modulate emotional processes. Based on this expression pattern, the therapeutic potential of several selective NK2 receptor antagonists has been investigated in animal models of anxiety and depression.

Interestingly, Saredutant (SR48968), a selective and brain penetrant NK2 receptor antagonist was effective in exploration based procedures sensitive to anxiolytics such as elevated plus maze and the light/dark test in rodents. Efficacy in procedures sensitive to anti-depressants in mouse, gerbils and marmosets is also been documented for Saredutant. Currently Saredutant is in clinical development for depression (Phase III).

Together these data suggest that NK2 receptor antagonists have potential as a new class of anti-depressants and anxiolytics.

Furthermore, NK2 receptor antagonists may be used in the treatment of schizophrenia.

SUMMARY OF THE INVENTION

The present invention provides compounds of formula I

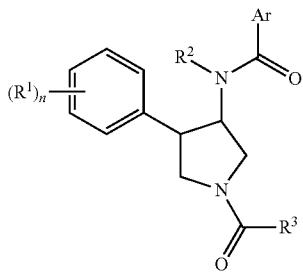

I wherein
$R^1$ is hydrogen, halogen, cyano or lower alkyl; n is 1, 2 or 3;
$R^2$ is hydrogen or lower alkyl;
$R^3$ is aryl- or a heteroaryl, wherein the rings of the aryl or heteroaryl group are optionally substituted by one or two substituents R';
R' is selected from hydrogen, halogen, lower alkyl, lower alkoxy, lower alkyl substituted by halogen, lower alkoxy substituted by halogen, —S(O)$_2$-lower alkyl, CN, —NR$^4$R$^5$, —C(O)-lower alkyl, heterocyclyl or heteroaryl;
$R^4$ and $R^5$ are each independently hydrogen, —(CO)CF$_3$ or lower alkyl or is a non aromatic heterocyclic group

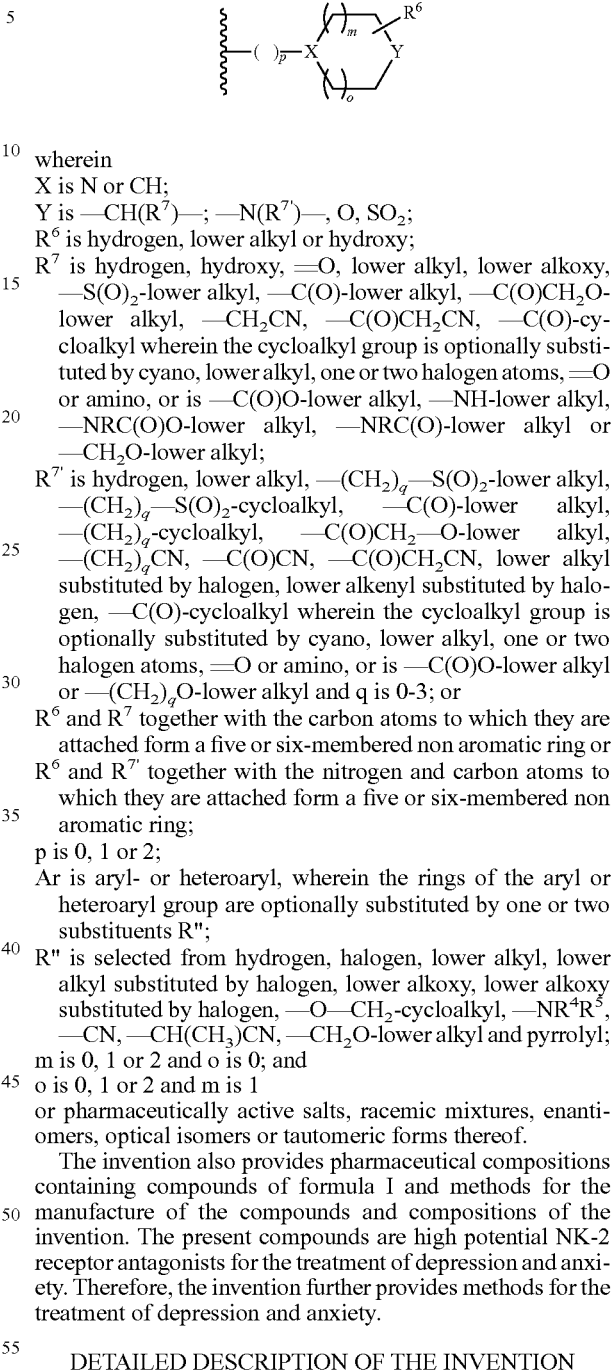

wherein
X is N or CH;
Y is —CH(R$^7$)—; —N(R$^{7'}$)—, O, SO$_2$;
$R^6$ is hydrogen, lower alkyl or hydroxy;
$R^7$ is hydrogen, hydroxy, =O, lower alkyl, lower alkoxy, —S(O)$_2$-lower alkyl, —C(O)-lower alkyl, —C(O)CH$_2$O-lower alkyl, —CH$_2$CN, —C(O)CH$_2$CN, —C(O)-cycloalkyl wherein the cycloalkyl group is optionally substituted by cyano, lower alkyl, one or two halogen atoms, =O or amino, or is —C(O)O-lower alkyl, —NH-lower alkyl, —NRC(O)O-lower alkyl, —NRC(O)-lower alkyl or —CH$_2$O-lower alkyl;
$R^{7'}$ is hydrogen, lower alkyl, —(CH$_2$)$_q$—S(O)$_2$-lower alkyl, —(CH$_2$)$_q$—S(O)$_2$-cycloalkyl, —C(O)-lower alkyl, —(CH$_2$)$_q$-cycloalkyl, —C(O)CH$_2$—O-lower alkyl, —(CH$_2$)$_q$CN, —C(O)CN, —C(O)CH$_2$CN, lower alkyl substituted by halogen, lower alkenyl substituted by halogen, —C(O)-cycloalkyl wherein the cycloalkyl group is optionally substituted by cyano, lower alkyl, one or two halogen atoms, =O or amino, or is —C(O)O-lower alkyl or —(CH$_2$)$_q$O-lower alkyl and q is 0-3; or
$R^6$ and $R^7$ together with the carbon atoms to which they are attached form a five or six-membered non aromatic ring or
$R^6$ and $R^{7'}$ together with the nitrogen and carbon atoms to which they are attached form a five or six-membered non aromatic ring;
p is 0, 1 or 2;
Ar is aryl- or heteroaryl, wherein the rings of the aryl or heteroaryl group are optionally substituted by one or two substituents R";
R" is selected from hydrogen, halogen, lower alkyl, lower alkyl substituted by halogen, lower alkoxy, lower alkoxy substituted by halogen, —O—CH$_2$-cycloalkyl, —NR$^4$R$^5$, —CN, —CH(CH$_3$)CN, —CH$_2$O-lower alkyl and pyrrolyl;
m is 0, 1 or 2 and o is 0; and
o is 0, 1 or 2 and m is 1
or pharmaceutically active salts, racemic mixtures, enantiomers, optical isomers or tautomeric forms thereof.

The invention also provides pharmaceutical compositions containing compounds of formula I and methods for the manufacture of the compounds and compositions of the invention. The present compounds are high potential NK-2 receptor antagonists for the treatment of depression and anxiety. Therefore, the invention further provides methods for the treatment of depression and anxiety.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes an alkyl group as defined above, wherein at least one hydrogen atom is replaced by halogen, for example —CF$_3$, —CHF$_2$, —CH$_2$F, —CH$_2$CF$_3$, —CH$_2$CH$_2$CF$_3$, —CH$_2$CF$_2$CF$_3$ and the like. Preferred lower alkyl substituted by halogen groups are groups having 1-4 carbon atoms.

The term "lower alkoxy" denotes an alkyl group as defined above, which is attached via an oxygen atom, for example, methoxy, ethoxy, propoxy, isopropoxy, n-butoxy, i-butoxy, 2-butoxy, t-butoxy and the like. Preferred alkoxy groups are groups with 1-4 carbon atoms.

The term "lower alkoxy substituted by halogen" denotes an alkoxy group as defined above wherein at least one hydrogen atom is replaced by halogen. Preferred lower alkoxy substituted by halogen groups are groups having 1-4 carbon atoms.

The term "halogen" denotes chlorine, iodine, fluorine and bromine.

The term "non aromatic heterocyclyl" denotes a saturated cyclic ring containing from 5-7 ring atoms, wherein at least one of the ring atoms is heteroatom, selected from N, O and S, for example morpholinyl, pyrrolidinyl, piperidinyl, piperazinyl, azepanyl, and the like. Preferred non aromatic heterocyclyl group is piperizinyl.

The term "aryl" denotes a cyclic aromatic hydrocarbon radical consisting of one or more fused rings containing 6-14 carbon atoms in which at least one ring is aromatic in nature, for example phenyl, benzyl, naphthyl or indanyl. Preferred is the phenyl group.

The term "heteroaryl" denotes a cyclic aromatic radical consisting of one or more fused rings containing 5-14 ring atoms, preferably containing 5-10 ring atoms, in which at least one ring is aromatic in nature and contains at least one heteroatom selected from N, O and S, for example quinoxalinyl, dihydroisoquinolinyl, pyrazinyl, pyrazolyl, pyridinyl, pyridyl, pyrimidinyl, oxadiazolyl, triazolyl, tetrazolyl, thiazolyl, thiadiazolyl, thienyl, furyl, imidazolyl, benzofuranyl, dihydrobenzofuranyl and benzo[1,3]dioxole. Preferred heteroaryl group is pyridinyl, pyrazolyl, benzofuranyl, dihydrobenzofuranyl, benzo[1,3]dioxole, and quinoxalinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The following groups of compounds of formula I are preferred:

Compounds of formula IA

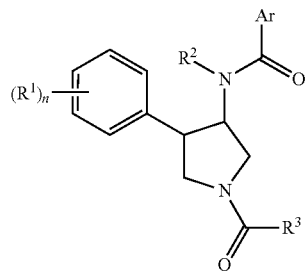

wherein
$R^1$ is hydrogen or halogen; n is 1 or 2;
$R^2$ is lower alkyl;

$R^3$ is

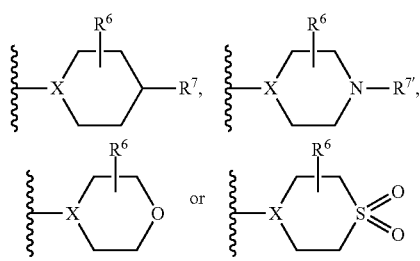

X is N or CH;
$R^6$ is hydrogen, lower alkyl or hydroxy;
$R^7$ is hydrogen, hydroxy, =O, lower alkyl, lower alkoxy, —S(O)$_2$-lower alkyl, —C(O)-lower alkyl, —C(O)CH$_2$O-lower alkyl, —CH$_2$CN, —C(O)CH$_2$CN, —C(O)-cycloalkyl wherein the cycloalkyl group is optionally substituted by cyano, lower alkyl, one or two halogen atoms, =O or amino, or is —C(O)O-lower alkyl, —NH-lower alkyl, —NRC(O)O-lower alkyl, —NRC(O)-lower alkyl or —CH$_2$O-lower alkyl;
$R^{7'}$ is hydrogen, lower alkyl, —(CH$_2$)$_q$—S(O)$_2$-lower alkyl, —(CH$_2$)$_q$—S(O)$_2$-cycloalkyl, —C(O)-lower alkyl, —(CH$_2$)$_q$-cycloalkyl, —C(O)CH$_2$—O-lower alkyl, —(CH$_2$)$_q$CN, —C(O)CN, —C(O)CH$_2$CN, lower alkyl substituted by halogen, lower alkenyl substituted by halogen, —C(O)-cycloalkyl wherein the cycloalkyl group is optionally substituted by cyano, lower alkyl, one or two halogen atoms, =O or amino, or is —C(O)O-lower alkyl or —(CH$_2$)$_q$O-lower alkyl and q is 0-3; or
$R^6$ and $R^7$ together with the carbon atoms to which they are attached form a five or six-membered non aromatic ring or
$R^6$ and $R^{7'}$ together with the nitrogen and carbon atoms to which they are attached form a five or six-membered non aromatic ring;
Ar is aryl- or heteroaryl, wherein the rings of the aryl or heteroaryl group are optionally substituted by one or two substituents R"; and
R" is selected from hydrogen, halogen, lower alkyl, lower alkyl substituted by halogen, lower alkoxy, lower alkoxy substituted by halogen, —O—CH$_2$-cycloalkyl, —NR$^4$R$^5$, —CN, —CH(CH$_3$)CN, —CH$_2$O-lower alkyl and pyrrolyl;
or pharmaceutically active salts, racemic mixtures, enantiomers, optical isomers or tautomeric forms thereof.

Compounds of formula IB

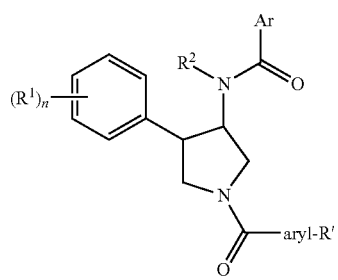

wherein
$R^1$ is hydrogen, halogen, cyano or lower alkyl; n is 1, 2 or 3;
R' is selected from hydrogen, halogen, lower alkyl, lower alkoxy, lower alkyl substituted by halogen, lower alkoxy substituted by halogen, —S(O)₂-lower alkyl, CN, —NR⁴R⁵, —C(O)-lower alkyl, heterocyclyl and heteroaryl;
R⁴ and R⁵ are each independently hydrogen, —(CO)CF₃ or lower alkyl
Ar is aryl- or heteroaryl, wherein the rings of the aryl or heteroaryl group are optionally substituted by one or two substituents R''; and
R'' is selected from hydrogen, halogen, lower alkyl, lower alkyl substituted by halogen, lower alkoxy, lower alkoxy substituted by halogen, —O—CH₂-cycloalkyl, —NR⁴R⁵, —CN, —CH(CH₃)CN, —CH₂O-lower alkyl and pyrrolyl;
or pharmaceutically active salts, racemic mixtures, enantiomers, optical isomers or tautomeric forms thereof.

Compounds of formula IC

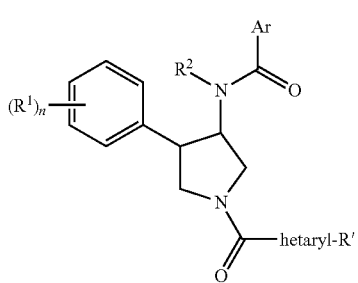

IC wherein
R¹ is hydrogen, halogen, cyano or lower alkyl; n is 1, 2 or 3;
R² is hydrogen or lower alkyl;
R' is selected from hydrogen, halogen, lower alkyl, lower alkoxy, lower alkyl substituted by halogen, lower alkoxy substituted by halogen, —S(O)₂-lower alkyl, CN, —NR⁴R⁵, —C(O)-lower alkyl, heterocyclyl and heteroaryl;
R⁴ and R⁵ are each independently hydrogen, —(CO)CF₃ or lower alkyl
Ar is aryl- or heteroaryl, wherein the rings of the aryl or heteroaryl group are optionally substituted by one or two substituents R'';
R'' is selected from hydrogen, halogen, lower alkyl, lower alkyl substituted by halogen, lower alkoxy, lower alkoxy substituted by halogen, —O—CH₂-cycloalkyl, —NR⁴R⁵, —CN, —CH(CH₃)CN, —CH₂O-lower alkyl and pyrrolyl;
or pharmaceutically active salts, racemic mixtures, enantiomers, optical isomers or tautomeric forms thereof.

Preferred compounds of formula IA are
rac-N-[(3S,4R)-4-(3,4-dichloro-phenyl)-1-(4-methanesulfonyl-piperazine-1-carbonyl)-pyrrolidin-3-yl]-4-methoxy-N-methyl-3-trifluoromethyl-benzamide;
rac-4-chloro-N-[(3S,4R)-4-(3,4-dichloro-phenyl)-1-(4-methanesulfonyl-piperazine-1-carbonyl)-pyrrolidin-3-yl]-N-methyl-benzamide;
rac-N-[(3S,4R)-4-(3,4-dichloro-phenyl)-1-(4-methanesulfonyl-piperazine-1-carbonyl)-pyrrolidin-3-yl]-4-ethyl-N-methyl-benzamide;
rac-N-[(3S,4R)-4-(3,4-dichloro-phenyl)-1-(4-methanesulfonyl-piperazine-1-carbonyl)-pyrrolidin-3-yl]-N-methyl-4-trifluoromethoxy-benzamide;
rac-N-[(3S,4R)-4-(3,4-dichloro-phenyl)-1-(4-methanesulfonyl-piperazine-1-carbonyl)-pyrrolidin-3-yl]-3-fluoro-N-methyl-4-trifluoromethyl-benzamide;
rac-N-[(3S,4R)-4-(3,4-dichloro-phenyl)-1-(4-methanesulfonyl-piperazine-1-carbonyl)-pyrrolidin-3-yl]-2-fluoro-N-methyl-3-trifluoromethyl-benzamide;
rac-N-[(3S,4R)-4-(3,4-dichloro-phenyl)-1-(4-methanesulfonyl-piperazine-1-carbonyl)-pyrrolidin-3-yl]-4-dimethylamino-N-methyl-benzamide;
rac-N-[(3S,4R)-4-(3,4-dichloro-phenyl)-1-(4-methanesulfonyl-piperazine-1-carbonyl)-pyrrolidin-3-yl]-4-fluoro-3,N-dimethyl-benzamide;
rac-N-[(3S,4R)-4-(3,4-dichloro-phenyl)-1-(4-methanesulfonyl-piperazine-1-carbonyl)-pyrrolidin-3-yl]-3-fluoro-4-methoxy-N-methyl-benzamide;
rac-2,2-difluoro-benzo[1,3]dioxole-5-carboxylic acid [(3S,4R)-4-(3,4-dichloro-phenyl)-1-(4-methanesulfonyl-piperazine-1-carbonyl)-pyrrolidin-3-yl]-methyl-amide;
rac-N-[(3S,4R)-4-(3,4-dichloro-phenyl)-1-(4-methanesulfonyl-piperazine-1-carbonyl)-pyrrolidin-3-yl]-N-methyl-4-pyrrol-1-yl-benzamide;
rac-3-chloro-N-[(3S,4R)-4-(3,4-dichloro-phenyl)-1-(4-methanesulfonyl-piperazine-1-carbonyl)-pyrrolidin-3-yl]-4-fluoro-N-methyl-benzamide;
rac-3-chloro-N-[(3S,4R)-4-(3,4-dichloro-phenyl)-1-(4-methanesulfonyl-piperazine-1-carbonyl)-pyrrolidin-3-yl]-4-methoxy-N-methyl-benzamide;
rac-N-[(3S,4R)-4-(3,4-dichloro-phenyl)-1-(4-methanesulfonyl-piperazine-1-carbonyl)-pyrrolidin-3-yl]-4-fluoro-N-methyl-3-trifluoromethyl-benzamide;
rac-N-[(3S,4R)-4-(3,4-dichloro-phenyl)-1-(4-methanesulfonyl-piperazine-1-carbonyl)-pyrrolidin-3-yl]-4-methoxy-N-methyl-benzamide;
rac-N-[(3S,4R)-4-(3,4-dichloro-phenyl)-1-(4-methanesulfonyl-piperazine-1-carbonyl)-pyrrolidin-3-yl]-2-fluoro-N-methyl-5-trifluoromethyl-benzamide;
N-[(3S,4R)-4-(3,4-dichloro-phenyl)-1-((S)-4-methanesulfonyl-3-methyl-piperazine-1-carbonyl)-pyrrolidin-3-yl]-4-methoxy-N-methyl-3-trifluoromethyl-benzamide;
N-[(3S,4R)-4-(3,4-dichloro-phenyl)-1-((R)-4-methanesulfonyl-3-methyl-piperazine-1-carbonyl)-pyrrolidin-3-yl]-4-methoxy-N-methyl-3-trifluoromethyl-benzamide;
N-{(3RS,4SR)-4-(4-chloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide;
N-{(3S,4R)-4-(4-chloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide;
4-{(3SR,4RS)-3-(4-chloro-phenyl)-4-[(4-methoxy-3-trifluoromethyl-benzoyl)-methyl-amino]-pyrrolidine-1-carbonyl}-piperidine-1-carboxylic acid tert-butyl ester;
N-{(3RS,4SR)-4-(3,4-dichloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide;
4-chloro-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-3-trifluoromethyl-benzamide;
N-{(3RS,4SR)-4-(3,4-dichloro-phenyl)-1-[1-(1-methyl-cyclopropanecarbonyl)-piperidine-4-carbonyl]-pyrrolidin-3-yl}-4-fluoro-N-methyl-3-trifluoromethoxy-benzamide;
4-chloro-N-{(3RS,4SR)-4-(3,4-dichloro-phenyl)-1-[1-(1-methyl-cyclopropanecarbonyl)-piperidine-4-carbonyl]-pyrrolidin-3-yl}-3-methoxy-N-methyl-benzamide;
N-{(3RS,4SR)-4-(3,4-dichloro-phenyl)-1-[1-(1-methyl-cyclopropanecarbonyl)-piperidine-4-carbonyl]-pyrrolidin-3-yl}-4-fluoro-N-methyl-benzamide;
N-{(3RS,4SR)-4-(3,4-dichloro-phenyl)-1-[1-(1-methyl-cyclopropanecarbonyl)-piperidine-4-carbonyl]-pyrrolidin-3-yl}-3-(4-fluoro-phenyl)-N-methyl-propionamide;
N-[(3RS,4SR)-4-(4-chloro-phenyl)-1-(piperidine-4-carbonyl)-pyrrolidin-3-yl]-4-methoxy-N-methyl-3-trifluoromethyl-benzamide;

N-[(3RS,4SR)-4-(4-chloro-phenyl)-1-(1-isopropyl-piperidine-4-carbonyl)-pyrrolidin-3-yl]-4-methoxy-N-methyl-3-trifluoromethyl-benzamide;
N-[(3RS,4SR)-4-(4-chloro-phenyl)-1-(1-cyclopropylmethyl-piperidine-4-carbonyl)-pyrrolidin-3-yl]-4-methoxy-N-methyl-3-trifluoromethyl-benzamide;
N-{(3S,4R)-4-(3,4-dichloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide;
5-chloro-pyridine-2-carboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide;
3-cyano-N-{(3RS,4SR)-4-(3,4-dichloro-phenyl)-1-[1-(1-methyl-cyclopropanecarbonyl)-piperidine-4-carbonyl]-pyrrolidin-3-yl}-4-fluoro-N-methyl-benzamide;
N-{(3RS,4SR)-4-(4-chloro-phenyl)-1-[1-(3,3,3-trifluoro-propyl)-piperidine-4-carbonyl]-pyrrolidin-3-yl}-4-methoxy-N-methyl-3-trifluoromethyl-benzamide;
N-{(3RS,4SR)-4-(4-chloro-phenyl)-1-[1-(3,3-dimethyl-butyl)-piperidine-4-carbonyl]-pyrrolidin-3-yl}-4-methoxy-N-methyl-3-trifluoromethyl-benzamide;
2-cyclopentyl-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-acetamide;
N-{(3RS,4SR)-4-(4-chloro-phenyl)-1-[1-(2,2-dimethyl-propyl)-piperidine-4-carbonyl]-pyrrolidin-3-yl}-4-methoxy-N-methyl-3-trifluoromethyl-benzamide;
N-[(3RS,4SR)-4-(4-chloro-phenyl)-1-(1-ethyl-piperidine-4-carbonyl)-pyrrolidin-3-yl]-4-methoxy-N-methyl-3-trifluoromethyl-benzamide;
N-{(3RS,4SR)-4-(4-chloro-phenyl)-1-[1-(3-methylsulfanyl-propyl)-piperidine-4-carbonyl]-pyrrolidin-3-yl}-4-methoxy-N-methyl-3-trifluoromethyl-benzamide;
N-{(3RS,4SR)-4-(4-chloro-phenyl)-1-[1-(3-methanesulfonyl-propyl)-piperidine-4-carbonyl]-pyrrolidin-3-yl}-4-methoxy-N-methyl-3-trifluoromethyl-benzamide;
4-{(3SR,4RS)-3-(3,4-dichloro-phenyl)-4-[(4-methoxy-3-trifluoromethyl-benzoyl)-methyl-amino]-pyrrolidine-1-carbonyl}-piperidine-1-carboxylic acid tert-butyl ester;
N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide;
N-[(3RS,4SR)-1-(1-cyclopropylmethyl-piperidine-4-carbonyl)-4-(3,4-dichloro-phenyl)-pyrrolidin-3-yl]-4-methoxy-N-methyl-3-trifluoromethyl-benzamide;
N-{(3RS,4SR)-4-(3,4-dichloro-phenyl)-1-[1-(3,3,3-trifluoro-propyl)-piperidine-4-carbonyl]-pyrrolidin-3-yl}-4-methoxy-N-methyl-3-trifluoromethyl-benzamide;
N-[(3RS,4SR)-4-(3,4-dichloro-phenyl)-1-(1-ethanesulfonyl-piperidine-4-carbonyl)-pyrrolidin-3-yl]-4-methoxy-N-methyl-3-trifluoromethyl-benzamide;
N-[(3RS,4SR)-1-(1-cyclopropanesulfonyl-piperidine-4-carbonyl)-4-(3,4-dichloro-phenyl)-pyrrolidin-3-yl]-4-methoxy-N-methyl-3-trifluoromethyl-benzamide;
N-[(3RS,4SR)-1-[1-(2-cyano-ethyl)-piperidine-4-carbonyl]-4-(3,4-dichloro-phenyl)-pyrrolidin-3-yl]-4-methoxy-N-methyl-3-trifluoromethyl-benzamide;
N-{(3RS,4SR)-4-(3,4-dichloro-phenyl)-1-[1-(2-methoxy-ethyl)-piperidine-4-carbonyl]-pyrrolidin-3-yl}-4-methoxy-N-methyl-3-trifluoromethyl-benzamide;
4-{(3SR,4RS)-3-(3,4-dichloro-phenyl)-4-[(4-methoxy-3-trifluoromethyl-benzoyl)-methyl-amino]-pyrrolidine-1-carbonyl}-piperidine-1-carboxylic acid ethyl ester;
N-{(3RS,4SR)-4-(3,4-dichloro-phenyl)-1-[4-(3-methyl-[1,2,4]oxadiazol-5-yl)-benzoyl]-pyrrolidin-3-yl}-4-methoxy-N-methyl-3-trifluoromethyl-benzamide;
N-{(3RS,4SR)-4-(3,4-dichloro-phenyl)-1-[1-(2-fluoro-allyl)-piperidine-4-carbonyl]-pyrrolidin-3-yl}-4-methoxy-N-methyl-3-trifluoromethyl-benzamide;
2-cyclopentyl-N-[(3RS,4SR)-1-(1-cyclopropylmethyl-piperidine-4-carbonyl)-4-(3,4-dichloro-phenyl)-pyrrolidin-3-yl]-N-methyl-acetamide;
4-chloro-N-[(3S,4R)-4-(4-chloro-phenyl)-1-(1-cyclopropylmethyl-piperidine-4-carbonyl)-pyrrolidin-3-yl]-N-methyl-3-trifluoromethyl-benzamide;
4-chloro-N-{(3S,4R)-4-(4-chloro-phenyl)-1-[1-(1-methyl-cyclopropanecarbonyl)-piperidine-4-carbonyl]-pyrrolidin-3-yl}-N-methyl-3-trifluoromethyl-benzamide;
4-chloro-N-[(3RS,4SR)-4-(4-chloro-phenyl)-1-(piperidine-4-carbonyl)-pyrrolidin-3-yl]-N-methyl-3-trifluoromethyl-benzamide;
4-chloro-N-[(3RS,4SR)-4-(4-chloro-phenyl)-1-(1-cyclopropanesulfonyl-piperidine-4-carbonyl)-pyrrolidin-3-yl]-N-methyl-3-trifluoromethyl-benzamide;
4-chloro-N-{(3RS,4SR)-4-(4-chloro-phenyl)-1-[1-(tetrahydro-pyran-4-yl)-piperidine-4-carbonyl]-pyrrolidin-3-yl}-N-methyl-3-trifluoromethyl-benzamide;
4-chloro-N-[(3RS,4SR)-4-(4-chloro-phenyl)-1-(1-cyanomethyl-piperidine-4-carbonyl)-pyrrolidin-3-yl]-N-methyl-3-trifluoromethyl-benzamide;
4-chloro-N-[(3RS,4SR)-1-(1-cyclopropylmethyl-piperidine-4-carbonyl)-4-(3,4-dichloro-phenyl)-pyrrolidin-3-yl]-N-methyl-3-trifluoromethyl-benzamide;
4-chloro-N-{(3RS,4SR)-4-(4-chloro-phenyl)-1-[1-(2-cyano-ethyl)-piperidine-4-carbonyl]-pyrrolidin-3-yl}-N-methyl-3-trifluoromethyl-benzamide;
4-trifluoromethyl-pyridine-2-carboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide;
4-chloro-N-[(3R,4S)-1-(1-cyclopropylmethyl-piperidine-4-carbonyl)-4-(3,4-dichloro-phenyl)-pyrrolidin-3-yl]-N-methyl-3-trifluoromethyl-benzamide;
4-trifluoromethyl-pyridine-2-carboxylic acid {(3S,4R)-4-(3,4-dichloro-phenyl)-1-[1-(1-methyl-cyclopropanecarbonyl)-piperidine-4-carbonyl]-pyrrolidin-3-yl}-methyl-amide;
3-bromo-4-chloro-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-benzamide;
4-chloro-3-cyclopropyl-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-benzamide;
4-chloro-N-{(3RS,4SR)-4-(3,4-dichloro-phenyl)-1-[1-(1-methyl-cyclopropanecarbonyl)-piperidine-4-carbonyl]-pyrrolidin-3-yl}-3-ethyl-N-methyl-benzamide; and
4-chloro-3-cyclopropyl-N-{(3S,4R)-4-(3,4-dichloro-phenyl)-1-[1-(1-methyl-cyclopropanecarbonyl)-piperidine-4-carbonyl]-pyrrolidin-3-yl}-N-methyl-benzamide.

Preferred compounds of formula IB are
rac-N-[(3S,4R)-1-(4-cyano-benzoyl)-4-(3,4-dichloro-phenyl)-pyrrolidin-3-yl]-4-methoxy-N-methyl-3-trifluoromethyl-benzamide;
rac-N-[(3S,4R)-4-(3,4-dichloro-phenyl)-1-(4-methoxy-benzoyl)-pyrrolidin-3-yl]-4-methoxy-N-methyl-3-trifluoromethyl-benzamide;
rac-N-[(3S,4R)-4-(3,4-dichloro-phenyl)-1-(4-dimethylamino-benzoyl)-pyrrolidin-3-yl]-4-methoxy-N-methyl-3-trifluoromethyl-benzamide;
rac-N-[(3S,4R)-4-(3,4-dichloro-phenyl)-1-(4-fluoro-benzoyl)-pyrrolidin-3-yl]-4-methoxy-N-methyl-3-trifluoromethyl-benzamide;
rac-N-[(3S,4R)-1-(3-cyano-benzoyl)-4-(3,4-dichloro-phenyl)-pyrrolidin-3-yl]-4-methoxy-N-methyl-3-trifluoromethyl-benzamide;
rac-N-[(3S,4R)-4-(3,4-dichloro-phenyl)-1-(2-fluoro-5-methanesulfonyl-benzoyl)-pyrrolidin-3-yl]-4-methoxy-N-methyl-3-trifluoromethyl-benzamide;

rac-N-[(3S,4R)-4-(3,4-dichloro-phenyl)-1-(4-trifluorom-ethyl-benzoyl)-pyrrolidin-3-yl]-4-methoxy-N-methyl-3-trifluoromethyl-benzamide;

rac-N-[(3S,4R)-4-(3,4-dichloro-phenyl)-1-(4-trifluo-romethoxy-benzoyl)-pyrrolidin-3-yl]-4-methoxy-N-methyl-3-trifluoromethyl-benzamide;

rac-N-[(3S,4R)-4-(3,4-dichloro-phenyl)-1-(3-methanesulfo-nyl-benzoyl)-pyrrolidin-3-yl]-4-methoxy-N-methyl-3-tri-fluoromethyl-benzamide;

rac-N-[(3S,4R)-4-(3,4-dichloro-phenyl)-1-(4-methoxy-3-methyl-benzoyl)-pyrrolidin-3-yl]-4-methoxy-N-methyl-3-trifluoromethyl-benzamide;

rac-N-[(3S,4R)-4-(3,4-dichloro-phenyl)-1-(3,5-dimethyl-benzoyl)-pyrrolidin-3-yl]-4-methoxy-N-methyl-3-trifluo-romethyl-benzamide;

rac-N-[(3S,4R)-1-(4-acetyl-benzoyl)-4-(3,4-dichloro-phe-nyl)-pyrrolidin-3-yl]-4-methoxy-N-methyl-3-trifluorom-ethyl-benzamide;

rac-4-methyl-pyridine-2-carboxylic acid [(3S,4R)-1-(4-cy-ano-benzoyl)-4-(3,4-dichloro-phenyl)-pyrrolidin-3-yl]-methyl-amide;

rac-4-chloro-N-[(3S,4R)-1-(4-cyano-benzoyl)-4-(3,4-dichloro-phenyl)-pyrrolidin-3-yl]-N-methyl-3-trifluo-romethyl-benzamide;

rac-3-tert-butyl-N-[(3S,4R)-1-(4-cyano-benzoyl)-4-(3,4-dichloro-phenyl)-pyrrolidin-3-yl]-4-methoxy-N-methyl-benzamide;

rac-6-chloro-N-[(3S,4R)-1-(4-cyano-benzoyl)-4-(3,4-dichloro-phenyl)-pyrrolidin-3-yl]-N-methyl-nicotina-mide;

rac-N-[(3S,4R)-1-(4-cyano-benzoyl)-4-(3,4-dichloro-phe-nyl)-pyrrolidin-3-yl]-N-methyl-6-trifluoromethyl-nicoti-namide; and N-{(3RS,4SR)-4-(3,4-dichloro-phenyl)-1-[4-(3-methyl-[1,2,4]oxadiazol-5-yl)-benzoyl]-pyrrolidin-3-yl}-4-meth-oxy-N-methyl-3-trifluoromethyl-benzamide.

Preferred compounds of formula IC are rac-N-[(3S,4R)-1-(benzofuran-5-carbonyl)-4-(3,4-dichloro-phenyl)-pyrrolidin-3-yl]-4-methoxy-N-methyl-3-trifluo-romethyl-benzamide;

rac-N-[(3S,4R)-4-(3,4-dichloro-phenyl)-1-(pyridine-4-car-bonyl)-pyrrolidin-3-yl]-4-methoxy-N-methyl-3-trifluo-romethyl-benzamide;

rac-N-[(3S,4R)-4-(3,4-dichloro-phenyl)-1-(2,6-dichloro-py-ridine-4-carbonyl)-pyrrolidin-3-yl]-4-methoxy-N-me-thyl-3-trifluoromethyl-benzamide; and rac-N-[(3S,4R)-4-(3,4-Dichloro-phenyl)-1-(1,5-dimethyl-1H-pyrazole-3-carbonyl)-pyrrolidin-3-yl]-4-methoxy-N-methyl-3-trifluoromethyl-benzamide.

A further embodiment of the invention are compounds of formula I-1

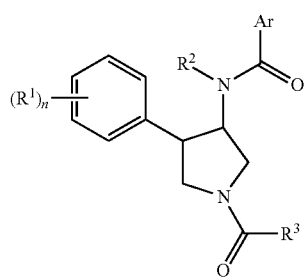

I-1 wherein
$R^1$ is hydrogen, halogen, cyano or lower alkyl; n is 1, 2 or 3;
$R^2$ is hydrogen or lower alkyl;

$R^3$ is aryl- or heteroaryl, wherein the rings of the aryl or heteroaryl group are optionally substituted by one or two substituents R';

R' is selected from hydrogen, halogen, lower alkyl, lower alkoxy, lower alkyl substituted by halogen, lower alkoxy substituted by halogen, —S(O)$_2$-lower alkyl, CN, —NR$^4$R$^5$, and —C(O)-lower alkyl;

$R^4$ and $R^5$ are each independently hydrogen, —(CO)CF$_3$ or lower alkyl or is a non aromatic heterocyclic group

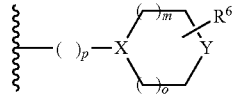

wherein
X is N or CH;
when X is CH, Y is —CH(R$^7$)—; —N(R$^7'$)—, or O; or
when X is N, Y is —CH(R$^7$)—; —N(R$^7$)—, O or SO$_2$,
$R^6$ is hydrogen, lower alkyl or hydroxy;
$R^7$ is hydrogen, hydroxy, =O, lower alkyl, —S(O)$_2$-lower alkyl, —C(O)-lower alkyl, —C(O)CH$_2$O-lower alkyl, —CH$_2$CN, —C(O)CH$_2$CN, —C(O)-cycloalkyl wherein the cycloalkyl group is optionally substituted by cyano, lower alkyl, one or two halogen atoms, =O or amino, or is —C(O)O-lower alkyl, —NH-lower alkyl, —NRC(O)O-lower alkyl, —NRC(O)-lower alkyl or —CH$_2$O-lower alkyl; and
$R^{7'}$ is hydrogen, lower alkyl, —S(O)$_2$-lower alkyl, —C(O)-lower alkyl, —C(O)CH$_2$—O-lower alkyl, —CH$_2$CN, —C(O)CN, —C(O)CH$_2$CN, —C(O)-cycloalkyl wherein the cycloalkyl group is optionally substituted by cyano, lower alkyl, one or two halogen atoms, =O or amino, or is —C(O)O-lower alkyl or —CH$_2$O-lower alkyl; or
$R^6$ and $R^7$ together with the carbon atoms to which they are attached form a five or six-membered non aromatic ring or
$R^6$ and $R^{7'}$ together with the nitrogen and carbon atoms to which they are attached form a five or six-membered non aromatic ring;
p is 0, 1 or 2;
Ar is aryl- or heteroaryl, wherein the rings of the aryl or heteroaryl group are optionally substituted by one or two substituents R";
R" is selected from hydrogen, halogen, lower alkyl, lower alkyl substituted by halogen, lower alkoxy, lower alkoxy substituted by halogen, —O—CH$_2$-cycloalkyl, —NR$^4$R$^5$, —CN, —CH(CH$_3$)CN, —CH$_2$O-lower alkyl and pyrrolyl;
m is 0, 1 or 2 and o is 0; and
is 0, 1 or 2 and m is 1
or pharmaceutically active salts, racemic mixtures, enanti-omers, optical isomers or tautomeric forms thereof.

More specifically, an embodiment of the present invention are compounds of formula I-11

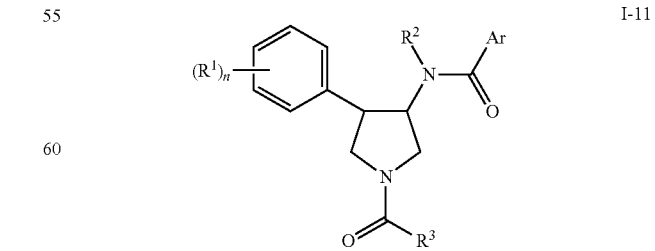

I-11 wherein
$R^1$ is hydrogen or halogen; n is 1 or 2;
$R^2$ is lower alkyl;

R³ is

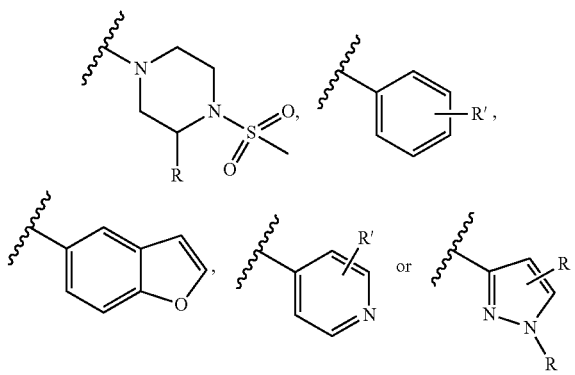

wherein R is hydrogen or lower alkyl; and
R' is selected from hydrogen, halogen, lower alkyl, lower alkoxy, lower alkyl substituted by halogen, lower alkoxy substituted by halogen, —S(O)₂-lower alkyl, CN, —NR⁴R⁵, and —C(O)-lower alkyl;
R⁴ and R⁵ are each independently hydrogen or lower alkyl;
Ar is aryl- or heteroaryl, wherein the rings of the aryl or heteroaryl group are optionally substituted by one or two substituents R";
R" is selected from hydrogen, halogen, lower alkyl, lower alkyl substituted by halogen, lower alkoxy, lower alkoxy substituted by halogen, —O—CH₂-cycloalkyl, —NR⁴R⁵, —CN, —CH(CH₃)CN, —CH₂O-lower alkyl and pyrrolyl;
or pharmaceutically active salts, racemic mixtures, enantiomers, optical isomers or tautomeric forms thereof.

An embodiment of the present invention are further compounds of formula I-12

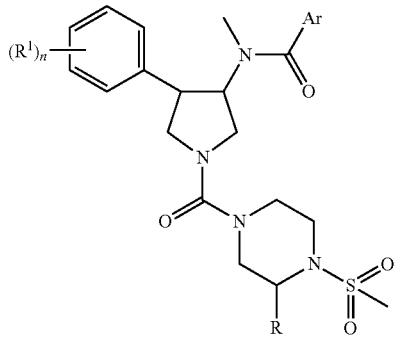

wherein R¹, n, R and Ar are as described above for compounds of formula I-11

An embodiment of the present invention are further compounds of formula I-13

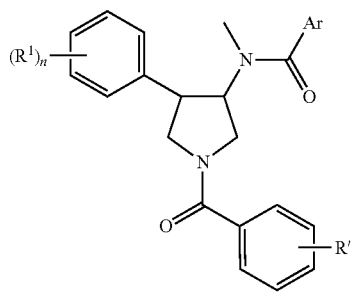

wherein R¹, n, R' and Ar are as described above for compounds of formula I-11

An embodiment of the present invention are further compounds of formula I-14

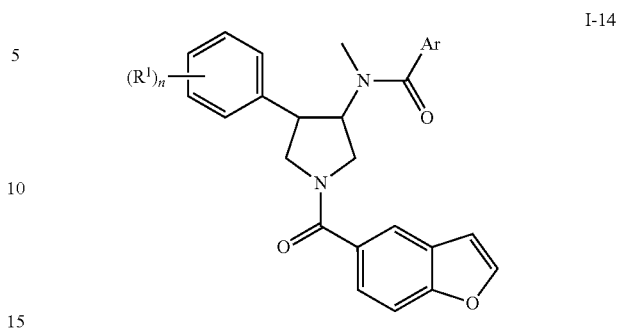

wherein R¹, n, and Ar are as described above for compounds of formula I-11.

An embodiment of the present invention are further compounds of formula I-15

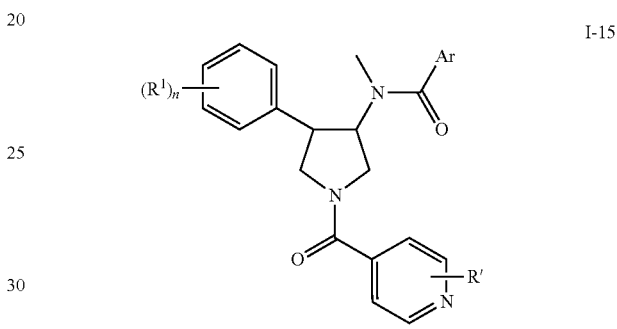

wherein R¹, n, R' and Ar are as described above for compounds of formula I-11.

An embodiment of the present invention are further compounds of formula I-16

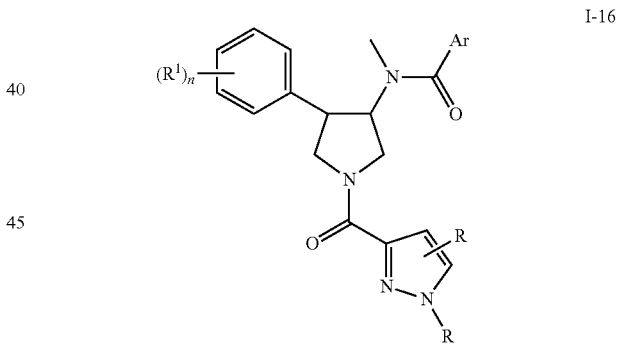

wherein R¹, n, R and Ar are as described above for compounds of formula I-11.

The preparation of compounds of formula I of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by processes described below, which process comprises
a) coupling a compound of formula VIII

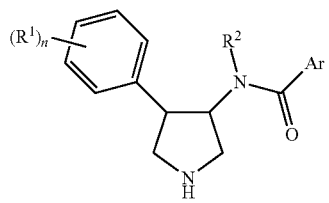

with a suitable carbamoyl chloride, acid chloride or carboxylic acid to obtain a compound of formula I

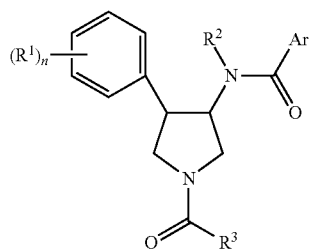

wherein the substituents $R^1$, $R^2$, $R^3$ and Ar are as defined above and if desired, converting the compounds obtained into pharmaceutically acceptable acid addition salts;
or
b) coupling a compound with formula XI

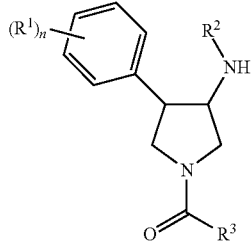

with a corresponding aryl carboxylic acid or aryl acid chloride, to obtain a compound of formula I

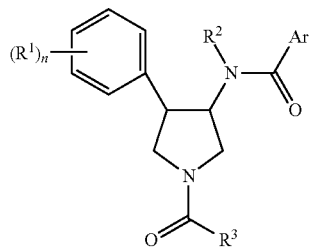

wherein the substituents $R^1$, $R^2$, $R^3$ and Ar are as defined above, and if desired, converting the compounds obtained into pharmaceutically acceptable acid addition salts.

The following schemes 1 and 2 describe the processes for preparation of compounds of formula I in more detail. The starting material of formula II is known compound and can be prepared according to methods known in the art.

Scheme 1

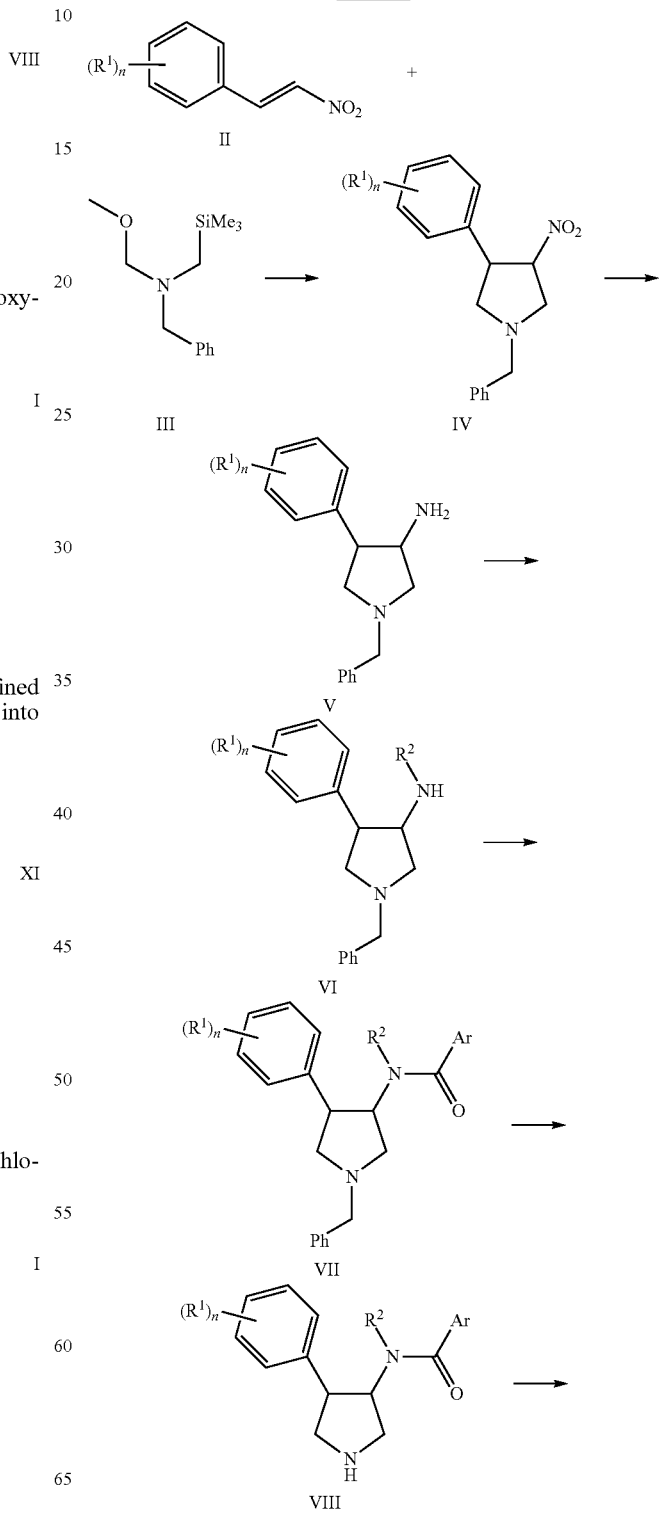

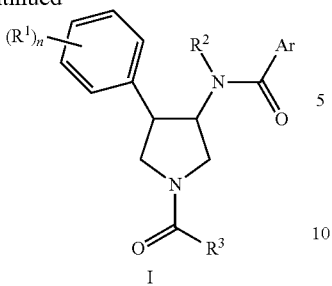

I $R^1$, $R^2$, $R^3$ and Ar have the same meanings as described above.

The 3,4-disubstituted pyrrolidine IV is prepared via a stereo specific 1,3-dipolar cycloaddition between the 2-nitrostyrene derivative II and the azomethine ylide generated in situ from the N-(methoxymethyl)-N-(phenylmethyl)-N-(trimethylsilyl)methylamine III in the presence of a catalytic amount of acid, such as TFA. Reduction of the nitro moiety of IV using standard conditions for example $SnCl_2.H_2O$ yields V. The amino moiety is subsequently alkylated to produce VI. Reaction of VI with an acid chloride in a presence of a base, usually $Et_3N$, or an amide coupling with a carboxylic acid yields VII. Selective N-debenzylation is then carried out using several known procedures which are compatible with the substitution patterns of the aromatic rings to afford VIII. Finally derivatives I are prepared via a coupling with a suitable carbamoyl chloride, acid chloride or carboxylic acide.

Scheme 2

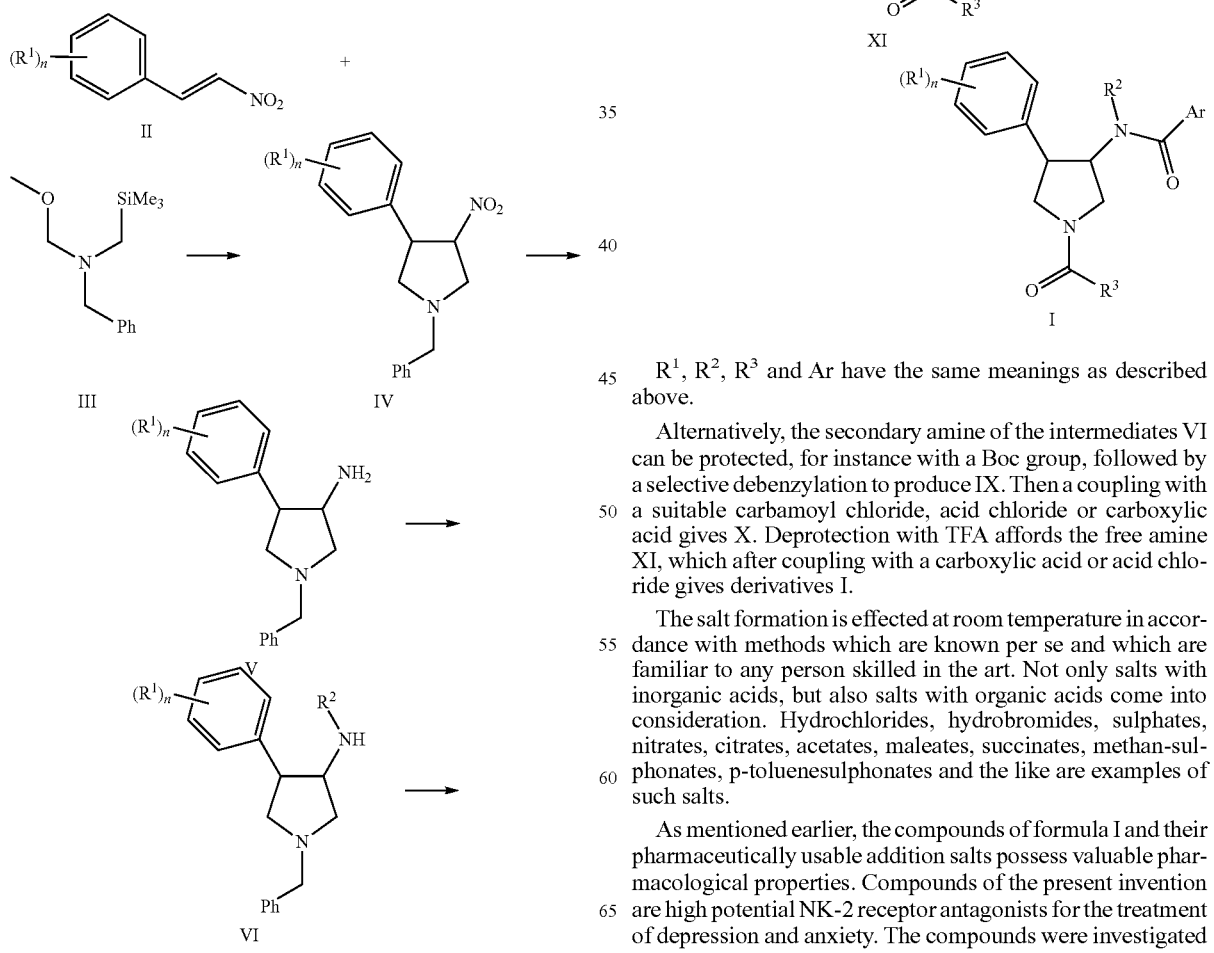

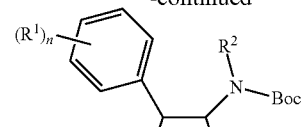

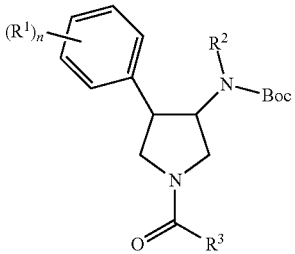

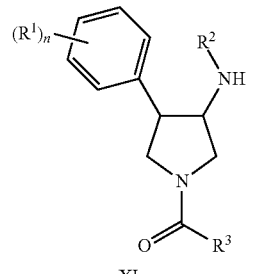

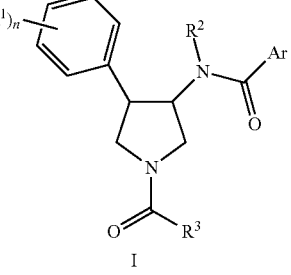

$R^1$, $R^2$, $R^3$ and Ar have the same meanings as described above.

Alternatively, the secondary amine of the intermediates VI can be protected, for instance with a Boc group, followed by a selective debenzylation to produce IX. Then a coupling with a suitable carbamoyl chloride, acid chloride or carboxylic acid gives X. Deprotection with TFA affords the free amine XI, which after coupling with a carboxylic acid or acid chloride gives derivatives I.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

As mentioned earlier, the compounds of formula I and their pharmaceutically usable addition salts possess valuable pharmacological properties. Compounds of the present invention are high potential NK-2 receptor antagonists for the treatment of depression and anxiety. The compounds were investigated in accordance with the tests given hereinafter.

Experimental Procedure

The compounds were investigated in accordance with the tests given hereinafter.

[$^3$H]SR48968 Competition Binding Assay hNK$_2$ receptor binding experiment were performed using [$^3$H]SR48968 (Catalog No. TRK398, specific activity: 27.0 Ci/mmol, Amersham, GE Healthcare UK limited, Buckinghamshire, UK) and membrane isolated from CHO cells stably expressing recombinant human NK2 receptor (product No. 6110510, Perkin Elmer biosignal Inc., Shelton, Conn., USA). After thawing, the membrane homogenates were centrifuged at 48,000×g for 10 min at 4° C., the pellets were resuspended in the 50 mM Tris-HCl, 3 mM MnCl$_2$, 4 μg/mL Chymostatin, 0.04% BSA binding buffer at pH 7.4 to a final assay concentration of 6.5 μg protein/well. For inhibition experiments, membranes were incubated with [$^3$H]SR48968 at a concentration equal to K$_D$ value of radioligand and 10 concentrations of the inhibitory compound (0.0003-10 μM) (in a total reaction volume of 500 μl) for 75 min at room temperature (RT). At the end of the incubation, membranes were filtered onto unitfilter (96-well white microplate with bonded GF/C filter preincubated 1 h in 0.3% polyethylenimine, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 μM 1-{2-[(R)-3-(3,4-dichloro-phenyl)-1-(3,4,5-trimethoxy-benzoyl)-pyrrolidin-3-yl]-ethyl}-4-phenyl-piperidine-4-carboxylic acid amide. The radioactivity on the filter was counted (5 min) on a Packard Top-count microplate scintillation counter with quenching correction after addition of 45 μl of microscint 40 (Canberra Packard S. A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). IC$_{50}$ values were derived from the inhibition curve and the affinity constant (K$_i$) values were calculated using the Cheng-Prussoff equation $K_i=IC_{50}/(1+[L]/K_D)$ where [L] was the concentration of radioligand and K$_D$ was its dissociation constant at the receptor, derived from the saturation isotherm.

Results of some compounds of the invention are provided in Table 1.

| Exp | Ki NK2 (μM) |
|---|---|
| 6 | 0.010709 |
| 7 | 0.033913 |
| 8 | 0.002327 |
| 9 | 0.086851 |
| 10 | 0.028806 |
| 11 | 0.014315 |
| 12 | 0.002745 |
| 13 | 0.0237 |
| 14 | 0.001172 |
| 15 | 0.065161 |
| 16 | 0.005093 |
| 17 | 0.09527 |
| 18 | 0.020671 |
| 20 | 0.002439 |
| 21 | 0.013075 |
| 22 | 0.004631 |
| 23 | 0.010176 |
| 24 | 0.001723 |
| 25 | 0.006013 |
| 26 | 0.009446 |
| 27 | 0.016243 |
| 28 | 0.002037 |
| 30 | 0.00459 |
| 31 | 0.014817 |
| 32 | 0.004574 |
| 33 | 0.008568 |
| 34 | 0.076737 |
| 35 | 0.028488 |
| 36 | 0.003591 |
| 37 | 0.008889 |
| 38 | 0.009498 |
| 39 | 0.068322 |
| 41 | 0.001449 |
| 42 | 0.001397 |
| 43 | 0.0022305 |
| 44 | 0.00424 |
| 45 | 0.002978 |
| 46 | 0.003259 |
| 47 | 0.003649 |
| 48 | 0.005359 |
| 49 | 0.002526 |
| 50 | 0.0063 |
| 51 | 0.003001 |
| 52 | 0.003721 |
| 53 | 0.002905 |
| 54 | 0.003811 |
| 55 | 0.00206 |
| 56 | 0.009521 |
| 57 | 0.001552 |
| 58 | 0.008517 |
| 59 | 0.0128 |
| 63 | 0.00264 |
| 65 | 0.0302 |
| 66 | 0.0498 |
| 67 | 0.0529 |
| 68 | 0.0743 |
| 69 | 0.0233 |
| 70 | 0.0397 |
| 71 | 0.0344 |
| 72 | 0.00058 |
| 73 | 0.0124 |
| 74 | 0.0013 |
| 75 | 0.023 |
| 76 | 0.096 |
| 77 | 0.0288 |
| 78 | 0.0078 |
| 80 | 0.04 |
| 81 | 0.0058 |
| 82 | 0.0117 |
| 83 | 0.0971 |
| 85 | 0.0821 |
| 86 | 0.0178 |
| 87 | 0.0008 |
| 88 | 0.0178 |
| 89 | 0.0233 |
| 90 | 0.0117 |
| 92 | 0.0139 |
| 94 | 0.0006 |
| 95 | 0.0022 |
| 96 | 0.0008 |
| 97 | 0.0007 |
| 98 | 0.0009 |
| 99 | 0.0009 |
| 100 | 0.0023 |
| 101 | 0.0162 |
| 102 | 0.0024 |
| 103 | 0.007 |
| 104 | 0.0041 |
| 105 | 0.0008 |
| 107 | 0.0006 |
| 108 | 0.0026 |
| 109 | 0.0008 |
| 110 | 0.0008 |
| 111 | 0.0007 |
| 113 | 0.0029 |
| 114 | 0.0172 |
| 115 | 0.023 |
| 116 | 0.0497 |
| 118 | 0.0324 |
| 119 | 0.0113 |

-continued

| Exp | Ki NK2 (µM) |
|---|---|
| 120 | 0.0008 |
| 121 | 0.0051 |
| 122 | 0.082 |
| 123 | 0.038 |
| 124 | 0.013 |
| 125 | 0.0679 |
| 126 | 0.0009 |
| 127 | 0.035 |
| 131 | 0.0001 |
| 132 | 0.0013 |
| 133 | 0.0002 |
| 134 | 0.0519 |
| 135 | 0.0854 |
| 138 | 0.0005 |
| 139 | 0.0006 |
| 140 | 0.0007 |
| 141 | 0.0007 |
| 142 | 0.0004 |
| 143 | 0.0269 |
| 144 | 0.0009 |
| 145 | 0.0011 |
| 147 | 0.0014 |
| 148 | 0.0005 |
| 150 | 0.0198 |
| 151 | 0.0067 |
| 152 | 0.023 |
| 153 | 0.0527 |
| 154 | 0.0005 |
| 156 | 0.0008 |
| 158 | 0.0254 |
| 159 | 0.0433 |
| 160 | 0.005 |
| 161 | 0.0017 |
| 162 | 0.0004 |
| 163 | 0.0037 |
| 164 | 0.0005 |
| 165 | 0.0013 |
| 166 | 0.0007 |
| 167 | 0.0936 |
| 168 | 0.0004 |
| 170 | 0.0004 |
| 171 | 0.0008 |
| 173 | 0.0017 |
| 174 | 0.0009 |
| 175 | 0.042 |
| 176 | 0.0006 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 0.01 mg to about 1000 mg per day and person of a compound of general formula I should be appropriate, although the above upper limit can also be exceeded when necessary.

EXAMPLE A

Tablets of the following composition were manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition were manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch were firstly mixed in a mixer and then in a comminuting machine. The mixture was returned to the mixer, the talc was added thereto and mixed thoroughly. The mixture was filled by machine into hard gelatin capsules.

EXAMPLE C

Suppositories of the following composition were manufactured:

|  | mg/supp. |
|---|---|
| Active substance | 15 |
| Suppository mass | 1285 |
| Total | 1300 |

The suppository mass was melted in a glass or steel vessel, mixed thoroughly and cooled to 45° C. Thereupon, the finely powdered active substance was added thereto and stirred until it had dispersed completely. The mixture was poured into suppository moulds of suitable size, left to cool. The suppositories were then removed from the moulds and packed individually in wax paper or metal foil.

The following Examples illustrate the present invention without limiting it. All temperatures are given in degrees Celsius.

Abbreviations
DMAP-=dimethyl-pyridin-4-yl-amine
ES-MS=Electro Spray Mass Spectroscopy
HPLC=high-performance liquid chromatography;
MS=mass spectroscopy;
RT=room temperature
TFA=trifluoroacetic acid
THF=tetrahydrofuran General Procedure I:
To a stirred solution of a pyrrolidine intermediate VIII or XI (1 mmol) in $CH_2Cl_2$ (15 ml) at RT were added ethyl-diisopropyl-amine (2 mmol) and a carbamoyl chloride or acid chloride of formula $R^3COCl$ (1.1 mmol). Stirring was continued until completion of the reaction. The reaction mixture was then concentrated under vacuo and purification by flash chromatography on $SiO_2$ or preparative HPLC yielded I.

General Procedure II:
To a stirred solution of a carboxylic acid derivative (commercially available or known in the literature) (1 mmol) in 10 mL of $CH_2Cl_2$ was added (1.3 mmol) of EDC, (1.3 mmol) of HOBt and $Et_3N$ (1.3 mmol). After one hour at RT, was added a pyrrolidine intermediate of general formula VIII or XI. The mixture was stirred at RT over night and then poured onto water and extracted with $CH_2Cl_2$. The combined organic phases were dried over $Na_2SO_4$ and concentrated under vacuo. Flash chromatography or preparative HPLC afforded the title compound. Description of pyrrolidine intermediates of formula VIII, XI Pyrrolidine Intermediates of Formula VIII Pyrrolidine VIII-1 rac-N-[(3S,4R)-4-(3,4-Dichloro-phenyl)-pyrrolidin-3-yl]-4-methoxy-N-methyl-3-trifluoromethyl-benzamide

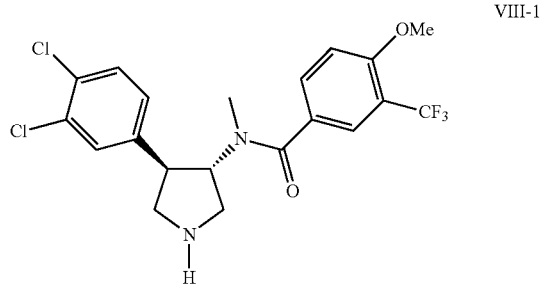 [SMILES: COc1ccc(C(=O)N(C)[C@@H]2CNC[C@H]2c2ccc(Cl)c(Cl)c2)cc1C(F)(F)F]

VIII-1 a) rac-(3R,4S)-1-Benzyl-3-(3,4-dichloro-phenyl)-4-nitro-pyrrolidine (IV-1)
A solution of N-(methoxymethyl)-N-(phenylmethyl)-N-(trimethylsilyl)methylamine (32.50 g, 0.135 mol) in $CH_2Cl_2$ (70 ml) was added drop wise, over a 30 minutes period, to a stirred solution of 1,2-dichloro-4-((E)-2-nitro-vinyl)-benzene (19.60 g, 0.09 mol) and trifluoroacetic acid (1.54 ml, 0.013 mol) in $CH_2Cl_2$ (160 ml) at 0° C. The ice bath was removed, and the solution was stirred at 25° C. for an additional 48 h. It was then concentrated and purification by flash chromatography ($SiO_2$, EtOAc/H 1:6) afforded 25.0 g (79%) of the title compound as a yellow oil. ES-MS m/e: 351.0 (M+H$^+$).

b) rac-(3S,4R)-1-Benzyl-4-(3,4-dichloro-phenyl)-pyrrolidin-3-ylamine (V-1)
To a stirred solution of rac-(3R,4S)-1-benzyl-3-(3,4-dichloro-phenyl)-4-nitro-pyrrolidine (11.60 g, 33.0 mmol) in EtOAc (200 ml) was added in one portion $SnCl_2.2H_2O$ (37.26 g, 0.165 mol). The reaction mixture was then heated at reflux for 4 hours, cooled down to RT and a saturated aqueous solution of $NaHCO_3$ was added. The salts were filtered off and the product extracted with EtOAc. The organic phases were then dried over $Na_2SO_4$, and concentration under vacuum gave 5.7 g (54%) of rac-(3S,4R)-1-benzyl-4-(3,4-dichloro-phenyl)-pyrrolidin-3-ylamine as a yellow oil. The product was then used in the next step without further purification. ES-MS m/e: 321.2 (M+H$^+$).

c) rac-[(3S,4R)-1-Benzyl-4-(3,4-dichloro-phenyl)-pyrrolidin-3-yl]-methyl-amine (VI-1)
To a solution of rac-(3S,4R)-1-benzyl-4-(3,4-dichloro-phenyl)-pyrrolidin-3-ylamine (0.54 g, 1.68 mmol) in THF (5 ml) was added a solution of $K_2CO_3$ (0.46 g, 3.36 mmol) in $H_2O$ (3 ml). After 10 minutes, ethyl chloroformate (0.18 ml, 1.85 mmol) was added and stirring was continued at RT for an additional 2 h. The intermediate carbamate was then extracted with $Et_2O$, dried over $Na_2SO_4$ and concentrated under vacuo to give viscous oil. The oil was taken up in THF (5 ml) and a solution of borane in THF (1M) was added (6.7 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with $Et_2O$ (20 ml) and neutralized with an aqueous solution of $NaHCO_3$. The organic phases were dried over $Na_2SO_4$ and the product purified by flash chromatography ($SiO_2$, $CH_2Cl_2$/MeOH 9:1) to afford 0.29 g (51%) of rac-[(3S,4R)-1-benzyl-4-(3,4-dichloro-phenyl)-pyrrolidin-3-yl]-methyl-amine as a colorless oil. ES-MS m/e: 335.3 (M+H$^+$).

d) rac-N-[(3S,4R)-1-benzyl-4-(3,4-dichloro-phenyl)-pyrrolidin-3-yl]-4-methoxy-N-methyl-3-trifluoromethyl-benzamide (VII-1)
A solution of 4-methoxy-3-trifluoromethyl-benzoyl chloride (commercially available) (0.88 g, 2.76 mmol) in $CH_2Cl_2$ (10 ml) was added drop wise to a stirred solution of rac-[(3S, 4R)-1-benzyl-4-(3,4-dichloro-phenyl)-pyrrolidin-3-yl]-methyl-amine (0.80 g, 2.38 mmol) and ethyl-diisopropyl-amine (0.61 ml, 3.58 mmol) in $CH_2Cl_2$ (10 ml). The reaction mixture was stirred 4 h, concentrated under vacuo and purification by flash chromatography ($SiO_2$, $CH_2Cl_2$/MeOH, 99:1) yielded 1.09 g (86%) of the title product as colorless oil. ES-MS m/e: 537.5 (M+H$^+$).

e) rac-N-[(3S,4R)-4-(3,4-Dichloro-phenyl)-pyrrolidin-3-yl]-4-methoxy-N-methyl-3-trifluoromethyl-benzamide (VIII-1)
To a stirred solution of rac-N-[(3S,4R)-1-benzyl-4-(3,4-dichloro-phenyl)-pyrrolidin-3-yl]-4-methoxy-N-methyl-3-trifluoromethyl-benzamide (1.10 g, 2.05 mmol) in $CH_3CN$ (15 ml) at RT was added 2,2,2-trichloroethyl chloroformate (0.56 ml, 4.10 mmol) in two portions (within 30 min.). The reaction mixture was stirred an additional 2 hours, concentrated under vacuo, and then filtrated on silica gel ($CH_2Cl_2$ as solvent) to afford the intermediate rac-(3R,4S)-3-(3,4-dichloro-phenyl)-4-[(4-methoxy-3-trifluoromethyl-benzoyl)-methyl-amino]-pyrrolidine-1-carboxylic acid 2,2,2-trichloro-ethyl ester. This intermediate was then dissolved in AcOH (10 ml) and zinc powder (300 mg) was added in 4 portions over 3 hours. The reaction mixture was then filtered on celite, concentrated under vacuo, taken up in CH$_2$Cl$_2$, and washed with aq. NaHCO$_3$. The organic phases were dried over Na$_2$SO$_4$, and purification by flash chromatography (SiO$_2$, CH$_2$Cl$_2$/MeOH, 90:10) yielded 0.45 g (50%) of the title product as colorless oil. ES-MS m/e: 447.1 (M+H$^+$).

Pyrrolidine Intermediates of Formula XI

Pyrrolidine XI-1 rac-(4-Methanesulfonyl-piperazin-1-yl)-((3S,4R)-3-methylamino-4-phenyl-pyrrolidin-1-yl)-methanone

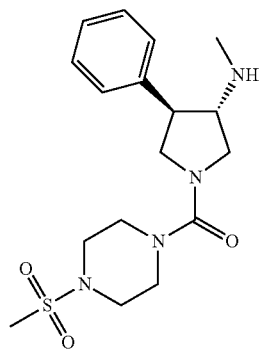

XI-1 a) rac-(3S,4R)-1-Benzyl-3-nitro-4-phenyl-pyrrolidine (IV-1)

A solution of N-(methoxymethyl)-N-(phenylmethyl)-N-(trimethylsilyl)methylamine (0.50 g, 2.02 mmol) in CH$_2$Cl$_2$ (15 ml) was added drop wise, over a 30 minutes period, to a stirred solution of ((E)-2-nitro-vinyl)-benzene (0.30 g, 2.02 mmol) and trifluoroacetic acid (0.17 ml, 0.2 mmol) in CH$_2$Cl$_2$ (10 ml) at 0° C. The ice bath was removed, and the solution was stirred at 25° C. for an additional 48 h. It was then concentrated and purification by flash chromatography (SiO$_2$, EtOAc/H 1:6) afforded 0.38 g (68%) of the title compound as a colorless oil. ES-MS m/e: 283 (M+H$^+$).

b) rac-(3S,4R)-1-Benzyl-4-phenyl-pyrrolidin-3-ylamine (V-1)

To a stirred solution of rac-(3S,4R)-1-benzyl-3-nitro-4-phenyl-pyrrolidine (1.0 g, 3.54 mmol) in EtOAc (50 ml) was added in one portion SnCl$_2$.2H$_2$O (3.99 g, 17.70 mmol). The reaction mixture was then heated at reflux for 2 hours, cooled down to RT and a saturated aqueous solution of NaHCO$_3$ (100 ml) was added. The salts were filtered off and the product extracted with EtOAc. The organic phases were then dried over Na$_2$SO$_4$, and concentration under vacuum gave 0.72 g (80%) of rac-(3S,4R)-1-benzyl-4-phenyl-pyrrolidin-3-ylamine as a light yellow oil. The product was then used in the next step without further purification.

c) rac-((3S,4R)-1-Benzyl-4-phenyl-pyrrolidin-3-yl)-methyl-amine (VI-1)

To a solution of rac-(3S,4R)-1-benzyl-4-phenyl-pyrrolidin-3-ylamine (0.25 g, 1.0 mmol) in THF (5 ml) was added a solution of K$_2$CO$_3$ (0.25 g, 1.8 mmol) in H$_2$O (2 ml). After 10 minutes, ethyl chloroformate (0.119 g, 1.1 mmol) was added and stirring was continued at RT for an additional 4 h. The intermediate carbamate was then extracted with Et$_2$O, dried over Na$_2$SO$_4$ and concentrated under vacuo to give viscous oil. The oil was taken up in THF (5 ml) and a solution of borane in THF (1M) was added (3.5 ml). The reaction mixture was then heated at 65° C. over night, cooled to RT and carefully quenched with conc. HCl (0.5 ml). The mixture was then heated at 80° C. for 2 h, cooled to RT, concentrated under vacuo, diluted with Et$_2$O (20 ml) and neutralized with an aqueous solution of NaHCO$_3$. The organic phases were dried over Na$_2$SO$_4$ and the product purified by flash chromatography (SiO$_2$, CH$_2$Cl$_2$/MeOH 9:1) to afford 0.21 g (82%) of rac-((3S,4R)-1-benzyl-4-phenyl-pyrrolidin-3-yl)-methyl-amine as a colorless oil.

d) rac-Methyl-((3S,4R)-4-phenyl-pyrrolidin-3-yl)-carbamic acid tert-butyl ester (IX-1)

To a solution of rac-((3S,4R)-1-benzyl-4-phenyl-pyrrolidin-3-yl)-methyl-amine (2.0 g, 7.55 mmol) in CH$_2$Cl$_2$ (20 ml) were added Et$_3$N (1.84 ml, 13.3 mmol) DMAP (81 mg, 0.66 mmol) and (Boc)$_2$O (1.74 g, 7.97 mmol). Stirring was continued 1 hour; the organic phase was washed with aq. HCl 1N, dried over Na$_2$SO$_4$ and the product purified by flash chromatography (SiO$_2$, Hx/EtOAc 4:1) to afford 2.03 g (76%) of ((3S,4R)-1-benzyl-4-phenyl-pyrrolidin-3-yl)-methyl-carbamic acid tert-butyl ester as a yellow oil. This intermediate was then dissolved in MeOH (20 ml), ammonium formate (1.60 g, 0.025 mol) and Pd/C (10%, 400 mg) was added. The reaction was stirred 2 hours, and then filtrated on celite, concentrated under vacuo. Purification by flash chromatography (SiO$_2$, CH$_2$Cl$_2$/MeOH 9:1) afforded 0.57 g (41%) of rac-methyl-((3S,4R)-4-phenyl-pyrrolidin-3-yl)-carbamic acid tert-butyl ester as a waxy solid. ES-MS m/e: 277.1 (M+H$^+$).

e) rac-[(3S,4R)-1-(4-Methanesulfonyl-piperazine-1-carbonyl)-4-phenyl-pyrrolidin-3-yl]-methyl-carbamic acid tert-butyl ester (X-1)

To a solution of rac-methyl-((3S,4R)-4-phenyl-pyrrolidin-3-yl)-carbamic acid tert-butyl ester (0.57 g, 2.1 mmol) in CH$_2$Cl$_2$ (15 ml) was added ethyl-diisopropyl-amine (0.53 ml, 3.11 mmol) and 4-methanesulfonyl-piperazine-1-carbonyl chloride (0.56 g, 2.5 mmol). Stirring was continued over night at RT, concentrated under vacuo and purification by flash chromatography (SiO$_2$, EtOAc/Hx 1:1) afforded 0.64 g (66%) of rac-[(3S,4R)-1-(4-methanesulfonyl-piperazine-1-carbonyl)-4-phenyl-pyrrolidin-3-yl]-methyl-carbamic acid tert-butyl ester as a white solid. ES-MS m/e: 467.3 (M+H$^+$).

4-Methanesulfonyl-piperazine-1-carbonyl chloride

To a stirred solution of carbonic acid ditrichloromethyl ester (triphosgene) (1.81 g, 6.09 mmol) in CH$_2$Cl$_2$ (30 ml) at 0° C., was added a solution of 1-methanesulfonyl-piperazine (2.0 g, 12.2 mmol) and pyridine (1.08 ml, 13.4 mmol) in CH$_2$Cl$_2$ (5 ml) over 30 minutes. The temperature was raised to RT, and stirring was continued over night. The organic phase was washed with H$_2$O, dried over Na$_2$SO$_4$. Purification by flash chromatography (SiO$_2$, EtOAc) yielded 2.20 g (79%) of 4-methanesulfonyl-piperazine-1-carbonyl chloride as white solid.

f) rac-(4-Methanesulfonyl-piperazin-1-yl)-((3S,4R)-3-methylamino-4-phenyl-pyrrolidin-1-yl)-methanone (XI-1)

To a solution of rac-[(3S,4R)-1-(4-methanesulfonyl-piperazine-1-carbonyl)-4-phenyl-pyrrolidin-3-yl]-methyl-carbamic acid tert-butyl ester (640 mg, 1.38 mmol) in CH$_2$Cl$_2$ (10 ml) was added TFA (2 ml) at RT. Stirring was continued over night. The reaction mixture was then concentrated under vacuo, the crude dissolved in CH$_2$Cl$_2$, washed with aq. NaHCO$_3$ and the organic phase dried over Na$_2$SO$_4$. Purification by flash chromatography (SiO$_2$, CH$_2$Cl$_2$/MeOH 95:5) yielded 0.49 g (98%) of the title compound as a white solid. ES-MS m/e: 367.1 (M+H$^+$).

Pyrrolidine XI-2 rac-2-(3,5-Bis-trifluoromethyl-phenyl)-N-[(3S,4R)-4-(4-chloro-phenyl)-pyrrolidin-3-yl]-N-methyl-isobutyramide

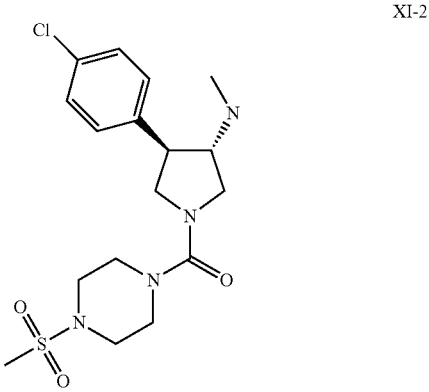 [SMILES: CN[C@@H]1CN(C(=O)N2CCN(S(C)(=O)=O)CC2)C[C@H]1c1ccc(Cl)cc1]

a) rac-(3R,4S)-1-Benzyl-3-(4-chloro-phenyl)-4-nitro-pyrrolidine (IV-2)

A solution of N-(methoxymethyl)-N-(phenylmethyl)-N-(trimethylsilyl)methylamine (6.70 g, 28.2 mmol) in CH$_2$Cl$_2$ (100 ml) was added drop wise, over a 30 minutes period, to a stirred solution of 1-chloro-4-((E)-2-nitro-vinyl)-benzene (4.97 g, 27.1 mmol) and trifluoroacetic acid (0.31 g, 2.7 mmol) in CH$_2$Cl$_2$ (150 ml) at 0° C. The ice bath was removed, and the solution was stirred at 25° C. for an additional 48 h. It was then concentrated and purification by flash chromatography (SiO$_2$, EtOAc/H 1:4) afforded 6.75 g (79%) of the title compound as a colorless oil.

b) rac-(3S,4R)-1-Benzyl-4-(4-chloro-phenyl)-pyrrolidin-3-ylamine (V-2)

Titanium (IV) chloride (0.36 g, 1.89 mmol) was added drop wise to a suspension of zinc powder (0.25 g, 3.78 mmol) in THF (3 ml). This solution was heated at 68° C. for one hour, then cooled to RT before rac-(3R,4S)-1-benzyl-3-(4-chloro-phenyl)-4-nitro-pyrrolidine (0.20 g, 0.63 mmol) in THF (2 ml) was added. The reaction mixture was then stirred at reflux over night. The reaction was cooled to RT, diluted with 300 ml of Et$_2$O, washed with an aqueous solution of NaHCO$_3$ and the organic phases were dried over Na$_2$SO$_4$. Flash chromatography (SiO$_2$, CH$_2$Cl$_2$/MeOH, 9:1) yielded 0.10 g (57%) of rac-(3S,4R)-1-benzyl-4-(4-chloro-phenyl)-pyrrolidin-3-ylamine as a light yellow oil.

c) rac-[(3S,4R)-1-Benzyl-4-(4-chloro-phenyl)-pyrrolidin-3-yl]-methyl-amine (VI-2)

To a solution of rac-(3S,4R)-1-benzyl-4-(4-chloro-phenyl)-pyrrolidin-3-ylamine (1.86 g, 6.51 mmol) in THF (20 ml) was added a solution of K$_2$CO$_3$ (1.80 g, 13.02 mmol) in H$_2$O (15 ml). After 10 minutes, ethyl chloroformate (0.68 ml, 7.16 mmol) was added and stirring was continued at RT for an additional 4 h. The intermediate carbamate was then extracted with Et$_2$O, dried over Na$_2$SO$_4$ and concentrated under vacuo to give viscous oil. The oil was taken up in THF (20 ml) and a solution of borane in THF (1M) was added (26 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with Et$_2$O (100 ml) and neutralized with an aqueous solution of NaHCO$_3$. The organic phases were dried over Na$_2$SO$_4$ and the product purified by flash chromatography (SiO$_2$, CH$_2$Cl$_2$/MeOH 9:1) to afford 1.51 g (77%) of rac-[(3S,4R)-1-benzyl-4-(4-chloro-phenyl)-pyrrolidin-3-yl]-methyl-amine as a colorless oil.

d) rac-[(3S,4R)-4-(4-Chloro-phenyl)-pyrrolidin-3-yl]-methyl-carbamic acid tert-butyl ester (IX-2)

To a solution of rac-[(3S,4R)-1-benzyl-4-(4-chloro-phenyl)-pyrrolidin-3-yl]-methyl-amine (1.19 g, 3.95 mmol) in CH$_2$Cl$_2$ (10 ml) were added Et$_3$N (1.1 ml, 7.91 mmol) DMAP (48 mg, 0.39 mmol) and (Boc)$_2$O (1.04 g, 4.75 mmol). Stirring was continued 1 hour; the organic phase was washed with aq. HCl 1N, dried over Na$_2$SO$_4$ and the product purified by flash chromatography (SiO$_2$, Hx/EtOAc 4:1) to afford 1.41 g (89%) of [(3S,4R)-1-benzyl-4-(4-chloro-phenyl)-pyrrolidin-3-yl]-methyl-carbamic acid tert-butyl ester as a yellow oil. This intermediate was dissolved in toluene (20 ml), and then chloroethyl chloroformate (0.75 g, 5.26 mmol) was added. Stirring was continued at 110° C. for 18 h, cooled to RT and MeOH (30 ml) was added. The solution was stirred at 80° C. over night, concentrated under vacuo, taken up in EtOAc, washed with an aqueous solution of NaHCO$_3$ and the organic phases dried over Na$_2$SO$_4$. Purification by flash chromatography (SiO$_2$, CH$_2$Cl$_2$/MeOH 90:10) yielded 0.77 g (62%) of rac-[(3S,4R)-4-(4-chloro-phenyl)-pyrrolidin-3-yl]-methyl-carbamic acid tert-butyl ester as light brown oil. ES-MS m/e: 311.4 (M+H$^+$).

e) rac-[(3S,4R)-1-(4-Methanesulfonyl-piperazine-1-carbonyl)-4-phenyl-pyrrolidin-3-yl]-methyl-carbamic acid tert-butyl ester (X-2)

To a solution of rac-[(3S,4R)-4-(4-chloro-phenyl)-pyrrolidin-3-yl]-methyl-carbamic acid tert-butyl ester (0.76 g, 2.46 mmol) in CH$_2$Cl$_2$ (10 ml) was added ethyl-diisopropyl-amine (0.51 ml, 2.95 mmol) and 4-methanesulfonyl-piperazine-1-carbonyl chloride (0.61 g, 2.7 mmol). Stirring was continued over night at RT, concentrated under vacuo and purification by flash chromatography (SiO$_2$, EtOAc/Hx 1:1) afforded 0.87 g (70%) of the title compound as a white solid. ES-MS m/e: 501.4 (M+H$^+$).

f) rac-[(3R,4S)-3-(4-Chloro-phenyl)-4-methylamino-pyrrolidin-1-yl]-(4-methanesulfonyl-piperazin-1-yl)-methanone (XI-2)

To a solution of rac-[(3S,4R)-1-(4-methanesulfonyl-piperazine-1-carbonyl)-4-phenyl-pyrrolidin-3-yl]-methyl-carbamic acid tert-butyl ester (0.86 g, 1.61 mmol) in CH$_2$Cl$_2$ (12 ml) was added TFA (3 ml) at RT. Stirring was continued over night. The reaction mixture was then concentrated under vacuo, the crude dissolved in CH$_2$Cl$_2$, washed with aq.NaHCO$_3$ and the organic phase dried over Na$_2$SO$_4$. Purification by flash chromatography (SiO$_2$, CH$_2$Cl$_2$/MeOH 95:5) yielded 0.68 g (98%) of the title compound as a white solid. ES-MS m/e: 401.3 (M+H$^+$).

Pyrrolidine XI-3 rac-[(3R,4S)-3-(3,4-Dichloro-phenyl)-4-methylamino-pyrrolidin-1-yl]-(4-methanesulfonyl-piperazin-1-yl)-methanone

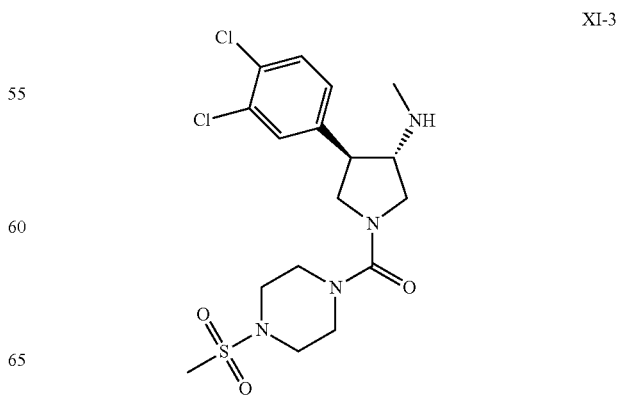

a) rac-[(3S,4R)-4-(3,4-Dichloro-phenyl)-pyrrolidin-3-yl]-methyl-carbamic acid tert-butyl ester (IX-3)

To a solution of rac-[(3S,4R)-1-benzyl-4-(3,4-dichloro-phenyl)-pyrrolidin-3-yl]-methyl-amine (described herein above) (0.28 g, 0.85 mmol) in CH$_2$Cl$_2$ (4 ml) were added Et$_3$N (0.24 ml, 1.71 mmol), DMAP (10 mg, 0.081 mmol) and (Boc)$_2$O (0.223 g, 1.02 mmol). Stirring was continued 1 hour; the organic phase was washed with aq. HCl 1N, dried over Na$_2$SO$_4$ and the product purified by flash chromatography (SiO$_2$, Hx/EtOAc 4:1) to afford 0.28 g (75%) of rac-[(3S,4R)-1-benzyl-4-(3,4-dichloro-phenyl)-pyrrolidin-3-yl]-methyl-carbamic acid tert-butyl ester as a colorless oil. This intermediate was then dissolved in CH$_3$CN (5 ml), and then 2,2,2-trichloroethyl chloroformate (0.11 ml, 0.78 mmol) was added. The reaction mixture was stirred at RT for 2 h and concentrated under vacuo. The crude product was then dissolved in AcOH (3 ml) and zinc powder (80 mg) was added in two portions. After 2 hours, the reaction mixture was filtrated on celite, the solvent evaporated, and then the crude product was taken up in CH$_2$Cl$_2$ and washed with aq. NaHCO$_3$. The organic phase was dried over Na$_2$SO$_4$ and purification by flash chromatography (SiO$_2$, CH$_2$Cl$_2$/MeOH 90:10) yielded 0.13 g (44%) of rac-[(3S,4R)-4-(3,4-dichloro-phenyl)-pyrrolidin-3-yl]-methyl-carbamic acid tert-butyl ester as light yellow oil. ES-MS m/e: 345.20 (M+H$^+$).

b) rac-[(3S,4R)-4-(3,4-Dichloro-phenyl)-1-(4-methanesulfonyl-piperazine-1-carbonyl)-pyrrolidin-3-yl]-methyl-carbamic acid tert-butyl ester (X-3)

To a solution of rac-[(3S,4R)-4-(3,4-dichloro-phenyl)-pyrrolidin-3-yl]-methyl-carbamic acid tert-butyl ester (130 mg, 0.376 mmol) in CH$_2$Cl$_2$ (5 ml) was added ethyl-diisopropyl-amine (0.10 ml, 0.56 mmol) and 4-methanesulfonyl-piperazine-1-carbonyl chloride (94 mg, 0.41 mmol). Stirring was continued over night at RT, concentrated under vacuo and purification by flash chromatography (SiO$_2$, EtOAc/Hx 3:1) afforded 135 mg (66%) of the title compound as a white solid. ES-MS m/e: 535.1 (M+H$^+$).

c) rac-[(3R,4S)-3-(3,4-Dichloro-phenyl)-4-methylamino-pyrrolidin-1-yl]-(4-methanesulfonyl-piperazin-1-yl)-methanone (XI-3)

To a solution of rac-[(3S,4R)-4-(3,4-dichloro-phenyl)-1-(4-methanesulfonyl-piperazine-1-carbonyl)-pyrrolidin-3-yl]-methyl-carbamic acid tert-butyl ester (130 mg, 0.24 mmol) in CH$_2$Cl$_2$ (5 ml) was added TFA (1 ml) at RT. Stirring was continued over night. The reaction mixture was then concentrated under vacuo, the crude dissolved in CH$_2$Cl$_2$, washed with aq.NaHCO$_3$ and the organic phase was dried over Na$_2$SO$_4$. Purification by flash chromatography (SiO$_2$, CH$_2$Cl$_2$/MeOH 95:5) yielded 100 mg (92%) of the title compound as light yellow oil. ES-MS m/e: 435.37 (M+H$^+$).

Pyrrolidine XI-4 rac-[(3R,4S)-3-(3,4-Dichloro-phenyl)-4-ethylamino-pyrrolidin-1-yl]-(4-methanesulfonyl-piperazin-1-yl)-methanone

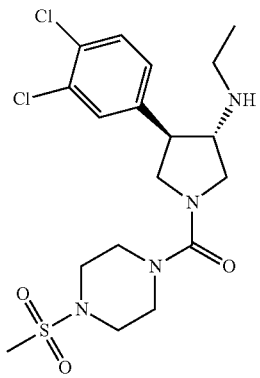

XI-4 a) rac-[(3S,4R)-1-Benzyl-4-(3,4-dichloro-phenyl)-pyrrolidin-3-yl]-ethyl-amine (VI-4)

To a stirred solution of acetic anhydride (0.75 ml, 7.97 mmol) in THF (10 ml) was added a solution of rac-(3S,4R)-1-benzyl-4-(3,4-dichloro-phenyl)-pyrrolidin-3-ylamine (described herein above) (2.00 g, 6.22 mmol) in THF (10 ml) dropwise over 30 minutes. The reaction mixture was stirred one additional hour, concentrated under vacuo, taken up in EtOAc, washed with aq. NaHCO3. and then the organic phase was dried over Na2SO4 to afford the intermediate N-[(3S,4R)-1-benzyl-4-(3,4-dichloro-phenyl)-pyrrolidin-3-yl]-acetamide. To this intermediate in THF (10 ml) at 0° C., was added portion wise LiAlH4 (0.49 g, 12.83 mmol). Stirring was continued over night at 65° C.). The reaction mixture was then heated at 65° C. over night, cooled to RT and carefully quenched with aq. NaHCO3. The product was extracted several times with EtOAc, the organic phases were then dried over Na$_2$SO$_4$ and the product purified by flash chromatography (SiO$_2$, CH$_2$Cl$_2$/MeOH 9:1) to afford 1.03 g (46%) of rac-[(3S,4R)-1-benzyl-4-(3,4-dichloro-phenyl)-pyrrolidin-3-yl]-ethyl-amine as a colorless oil. ES-MS m/e: 349.10 (M+H$^+$).

b) rac-[(3S,4R)-4-(3,4-Dichloro-phenyl)-pyrrolidin-3-yl]-ethyl-carbamic acid tert-butyl ester (IX-4)

To a solution of rac-[(3S,4R)-1-benzyl-4-(3,4-dichloro-phenyl)-pyrrolidin-3-yl]-ethyl-amine (0.99 g, 2.83 mmol) in CH$_2$Cl$_2$ (15 ml) were added Et$_3$N (0.78 ml, 5.67 mmol), DMAP (35 mg, 0.28 mmol) and (Boc)$_2$O (0.68 g, 3.11 mmol). Stirring was continued at RT over night; the organic phase was washed with aq. HCl 1N, dried over Na$_2$SO$_4$ and the product purified by flash chromatography (SiO$_2$, Hx/EtOAc 4:1) to afford 0.98 g (77%) of rac-[(3S,4R)-1-benzyl-4-(3,4-dichloro-phenyl)-pyrrolidin-3-yl]-ethyl-carbamic acid tert-butyl ester as a colorless oil. This intermediate was then dissolved in CH$_3$CN (10 ml), and then 2,2,2-trichloroethyl chloroformate (0.30 ml, 2.21 mmol) was added. The reaction mixture was stirred at RT for 2 h and concentrated under vacuo. The crude product was then dissolved in AcOH (5 ml) and zinc powder (300 mg) was added in two portions. After 2 hours, the reaction mixture was filtrated on celite, the solvent evaporated, and then the crude product was taken up in CH$_2$Cl$_2$ and washed with aq. NaHCO$_3$. The organic phase was dried over Na$_2$SO$_4$ and purification by flash chromatography (SiO$_2$, CH$_2$Cl$_2$/MeOH 90:10) yielded 0.25 g (33%) of rac-[(3S,4R)-4-(3,4-dichloro-phenyl)-pyrrolidin-3-yl]-ethyl-carbamic acid tert-butyl ester as light yellow oil. ES-MS m/e: 359.3 (M+H$^+$).

c) rac-[(3S,4R)-4-(3,4-Dichloro-phenyl)-1-(4-methanesulfonyl-piperazine-1-carbonyl)-pyrrolidin-3-yl]-ethyl-carbamic acid tert-butyl ester (X-4)

To a solution of rac-[(3S,4R)-4-(3,4-dichloro-phenyl)-pyrrolidin-3-yl]-ethyl-carbamic acid tert-butyl ester (0.25 g, 0.69 mmol) in CH$_2$Cl$_2$ (5 ml) was added ethyl-diisopropyl-amine (0.20 ml, 1.1 mmol) and 4-methanesulfonyl-piperazine-1-carbonyl chloride (189 mg, 0.83 mmol). Stirring was continued over night at RT, concentrated under vacuo and purification by flash chromatography (SiO$_2$, EtOAc) afforded 0.37 g (97%) of the title compound as a white solid. ES-MS m/e: 549.3 (M+H$^+$).

d) rac-[(3R,4S)-3-(3,4-Dichloro-phenyl)-4-ethylamino-pyrrolidin-1-yl]-(4-methanesulfonyl-piperazin-1-yl)-methanone (XI-3)

To a solution of rac-[(3S,4R)-4-(3,4-dichloro-phenyl)-1-(4-methanesulfonyl-piperazine-1-carbonyl)-pyrrolidin-3-yl]-ethyl-carbamic acid tert-butyl ester (0.36 g, 0.66 mmol) in CH$_2$Cl$_2$ (10 ml) was added TFA (2 ml) at RT. Stirring was continued over night. The reaction mixture was then concentrated under vacuo, the crude dissolved in CH$_2$Cl$_2$, washed with aq.NaHCO$_3$ and the organic phase was dried over Na$_2$SO$_4$. Purification by flash chromatography (SiO$_2$, CH$_2$Cl$_2$/MeOH 95:5) yielded 0.25 g (84%) of the title compound as light yellow oil. ES-MS m/e: 449.8 (M+H$^+$).

Pyrrolidine XI-5 rac-4-[(3R,4S)-3-(3,4-Dichloro-phenyl)-4-methylamino-pyrrolidine-1-carbonyl]-benzonitrile

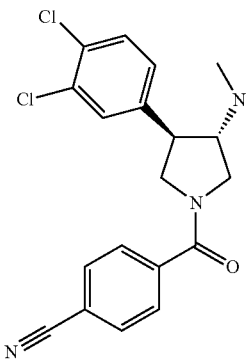

a) rac-[(3S,4R)-1-(4-Cyano-benzoyl)-4-(3,4-dichloro-phenyl)-pyrrolidin-3-yl]-methyl-carbamic acid tert-butyl ester (X-5)

To a solution of rac-[(3S,4R)-4-(3,4-dichloro-phenyl)-pyrrolidin-3-yl]-methyl-carbamic acid tert-butyl ester (810 mg, 2.35 mmol, described herein above) in CH$_2$Cl$_2$ (20 ml) was added triethyl-amine (0.42 ml, 3.05 mmol) and 4-cyano-benzoyl chloride (466 mg, 2.81 mmol). Stirring was continued over night at RT, concentrated under vacuo and purification by flash chromatography (SiO$_2$, EtOAc/Hx 2:1) afforded 1.09 g (98%) of the title compound as a white foam. ES-MS m/e: 474.4 (M+H$^+$).

b) rac-4-[(3R,4S)-3-(3,4-Dichloro-phenyl)-4-methylamino-pyrrolidine-1-carbonyl]-benzonitrile (XI-5)

To a solution of rac-[(3S,4R)-1-(4-cyano-benzoyl)-4-(3,4-dichloro-phenyl)-pyrrolidin-3-yl]-methyl-carbamic acid tert-butyl ester (1.08 g, 2.28 mmol) in CH$_2$Cl$_2$ (25 ml) was added TFA (5 ml) at RT. Stirring was continued one hour. The reaction mixture was then concentrated under vacuo, the crude dissolved in CH$_2$Cl$_2$, washed with aq.NaHCO$_3$ and the organic phase was dried over Na$_2$SO$_4$. Purification by flash chromatography (SiO$_2$, CH$_2$Cl$_2$/MeOH 95:5) yielded 0.72 g (85%) of the title compound as light yellow foam. ES-MS m/e: 374.0 (M+H$^+$).

EXAMPLE 1 rac-N-[(3S,4R)-1-(4-Methanesulfonyl-piperazine-1-carbonyl)-4-phenyl-pyrrolidin-3-yl]-N-methyl-3,5-bis-trifluoromethyl-benzamide

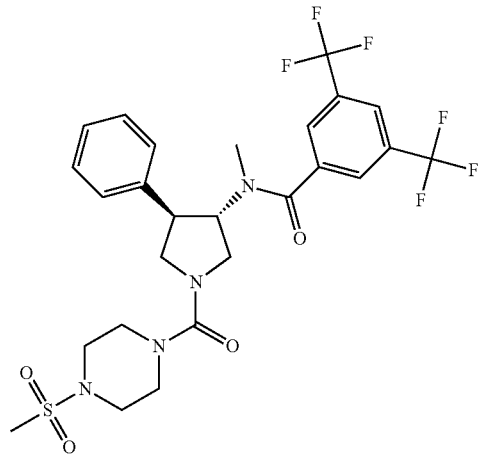 [SMILES: CN(C(=O)c1cc(C(F)(F)F)cc(C(F)(F)F)c1)[C@@H]1CN(C(=O)N2CCN(S(C)(=O)=O)CC2)C[C@H]1c1ccccc1]

Coupling according to general procedure I:

Pyrrolidine intermediate: rac-(4-Methanesulfonyl-piperazin-1-yl)-((3S,4R)-3-methylamino-4-phenyl-pyrrolidin-1-yl)-methanone (XI-1), Acid chloride: 3,5-Bis-trifluoromethyl-benzoyl chloride (commercially available), ES-MS m/e: 607.3 (M+H$^+$).

EXAMPLE 2 rac-N-[(3S,4R)-1-(4-Methanesulfonyl-piperazine-1-carbonyl)-4-phenyl-pyrrolidin-3-yl]-N-methyl-4-trifluoromethyl-benzamide

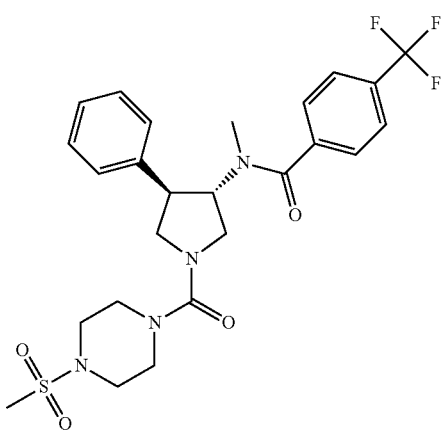 [SMILES: CN(C(=O)c1ccc(C(F)(F)F)cc1)[C@@H]1CN(C(=O)N2CCN(S(C)(=O)=O)CC2)C[C@H]1c1ccccc1]

Coupling according to general procedure I:

Pyrrolidine intermediate: rac-(4-Methanesulfonyl-piperazin-1-yl)-((3S,4R)-3-methylamino-4-phenyl-pyrrolidin-1-yl)-methanone (XI-1), Acid chloride: 4-Trifluoromethyl-benzoyl chloride (commercially available), ES-MS m/e: 539.5 (M+H$^+$).

EXAMPLE 3 rac-4-Dimethylamino-N-[(3S,4R)-1-(4-methanesulfonyl-piperazine-1-carbonyl)-4-phenyl-pyrrolidin-3-yl]-N-methyl-benzamide

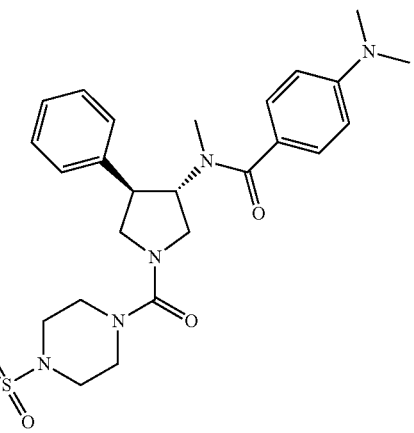

Coupling according to general procedure I:

Pyrrolidine intermediate: rac-(4-Methanesulfonyl-piperazin-1-yl)-((3S,4R)-3-methylamino-4-phenyl-pyrrolidin-1-yl)-methanone (XI-1), Acid chloride: 4-Dimethylamino-benzoyl chloride (commercially available), ES-MS m/e: 514.5 (M+H⁺).

EXAMPLE 4 rac-N-[(3S,4R)-1-(4-Methanesulfonyl-piperazine-1-carbonyl)-4-phenyl-pyrrolidin-3-yl]-4-methoxy-N-methyl-3-trifluoromethyl-benzamide

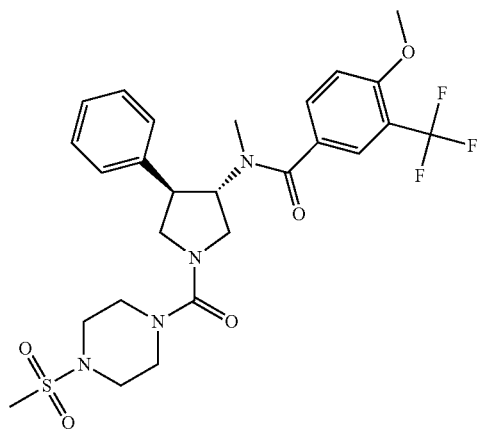 [SMILES: COc1ccc(C(=O)N(C)[C@@H]2CN(C(=O)N3CCN(S(C)(=O)=O)CC3)C[C@H]2c2ccccc2)cc1C(F)(F)F]

Coupling according to general procedure I:
Pyrrolidine intermediate: rac-(4-Methanesulfonyl-piperazin-1-yl)-((3S,4R)-3-methylamino-4-phenyl-pyrrolidin-1-yl)-methanone (XI-1),
Acid chloride: 4-Methoxy-3-trifluoromethyl-benzoyl chloride (commercially available), ES-MS m/e: 569.3 (M+H⁺).

EXAMPLE 5 rac-3,5-Dichloro-N-[(3S,4R)-1-(4-methanesulfonyl-piperazine-1-carbonyl)-4-phenyl-pyrrolidin-3-yl]-N-methyl-benzamide

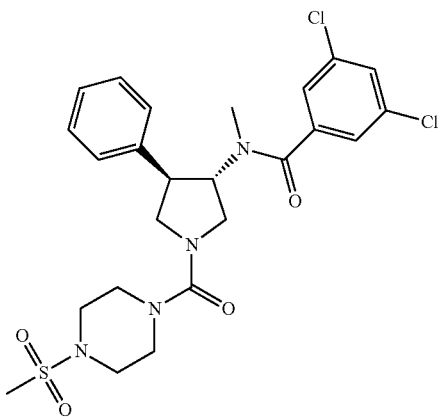 [SMILES: CN(C(=O)c1cc(Cl)cc(Cl)c1)[C@@H]1CN(C(=O)N2CCN(S(C)(=O)=O)CC2)C[C@H]1c1ccccc1]

Coupling according to general procedure I:
Pyrrolidine intermediate: rac-(4-Methanesulfonyl-piperazin-1-yl)-((3S,4R)-3-methylamino-4-phenyl-pyrrolidin-1-yl)-methanone (XI-1), Acid chloride: 3,5-Dichloro-benzoyl chloride (commercially available), ES-MS m/e: 540.1 (M+H⁺).

EXAMPLE 6 rac-N-[(3S,4R)-4-(4-Chloro-phenyl)-1-(4-methanesulfonyl-piperazine-1-carbonyl)-pyrrolidin-3-yl]-4-methoxy-N-methyl-3-trifluoromethyl-benzamide

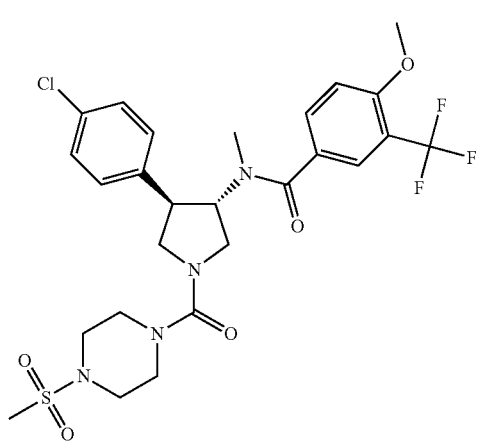 [SMILES: COc1ccc(C(=O)N(C)[C@@H]2CN(C(=O)N3CCN(S(C)(=O)=O)CC3)C[C@H]2c2ccc(Cl)cc2)cc1C(F)(F)F]

Coupling according to general procedure I:
Pyrrolidine intermediate: rac-[(3R,4S)-3-(4-Chloro-phenyl)-4-methylamino-pyrrolidin-1-yl]-(4-methanesulfonyl-piperazin-1-yl)-methanone (XI-2),
Acid chloride: 4-Methoxy-3-trifluoromethyl-benzoyl chloride (commercially available), ES-MS m/e: 603.3 (M+H⁺).

EXAMPLE 7 rac-N-[(3S,4R)-4-(4-Chloro-phenyl)-1-(4-methanesulfonyl-piperazine-1-carbonyl)-pyrrolidin-3-yl]-N-methyl-3-trifluoromethyl-benzamide

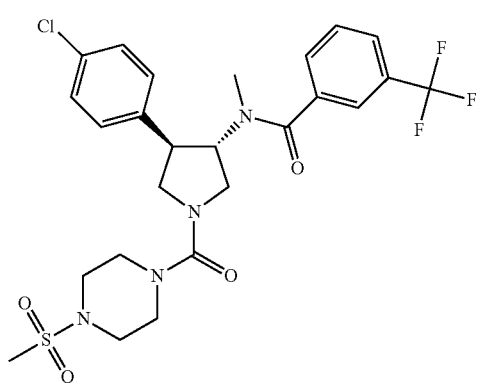 [SMILES: CN(C(=O)c1cccc(C(F)(F)F)c1)[C@@H]1CN(C(=O)N2CCN(S(C)(=O)=O)CC2)C[C@H]1c1ccc(Cl)cc1]

Coupling according to general procedure I:
Pyrrolidine intermediate: rac-[(3R,4S)-3-(4-Chloro-phenyl)-4-methylamino-pyrrolidin-1-yl]-(4-methanesulfonyl-piperazin-1-yl)-methanone (XI-2), Acid chloride: 3-Trifluoromethyl-benzoyl chloride (commercially available), ES-MS m/e: 573.1 (M+H⁺).

EXAMPLE 8 rac-N-[(3S,4R)-4-(3,4-Dichloro-phenyl)-1-(4-methanesulfonyl-piperazine-1-carbonyl)-pyrrolidin-3-yl]-4-methoxy-N-methyl-3-trifluoromethyl-benzamide

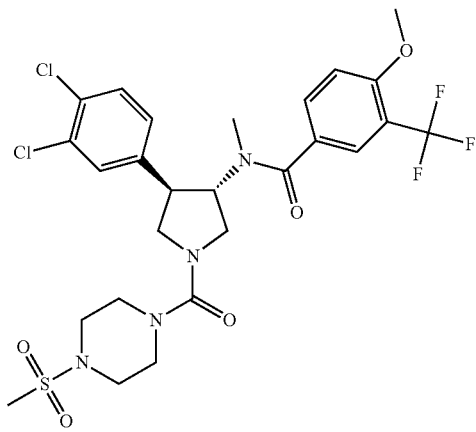 [SMILES: COc1ccc(C(=O)N(C)[C@@H]2CN(C(=O)N3CCN(S(C)(=O)=O)CC3)C[C@H]2c2ccc(Cl)c(Cl)c2)cc1C(F)(F)F]

Coupling according to general procedure I:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Acid chloride: 4-Methoxy-3-trifluoromethyl-benzoyl chloride (commercially available), ES-MS m/e: 637.2 (M+H⁺).

EXAMPLE 9 rac-N-[(3S,4R)-4-(3,4-Dichloro-phenyl)-1-(4-methanesulfonyl-piperazine-1-carbonyl)-pyrrolidin-3-yl]-N-methyl-benzamide

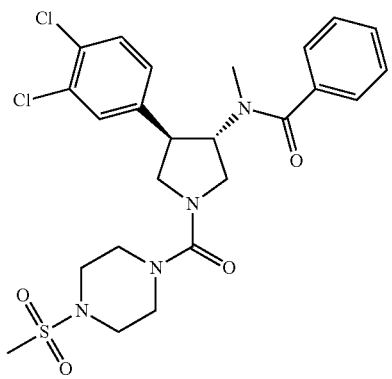 [SMILES: CN(C(=O)c1ccccc1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Acid chloride: Benzoyl chloride (commercially available), ES-MS m/e: 539.3 (M+H⁺).

EXAMPLE 10 rac-N-[(3S,4R)-4-(3,4-Dichloro-phenyl)-1-(4-methanesulfonyl-piperazine-1-carbonyl)-pyrrolidin-3-yl]-4-fluoro-N-methyl-benzamide

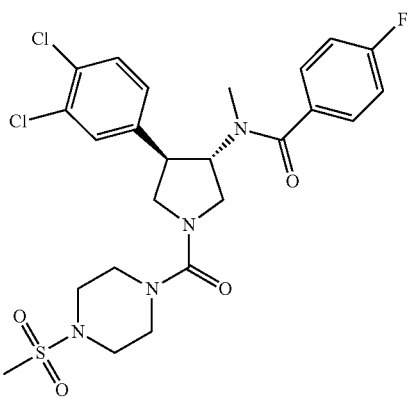 [SMILES: CN(C(=O)c1ccc(F)cc1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Acid chloride: 4-Fluoro-benzoyl chloride (commercially available), ES-MS m/e: 557.1 (M+H⁺).

EXAMPLE 11 rac-3-Chloro-N-[(3S,4R)-4-(3,4-dichloro-phenyl)-1-(4-methanesulfonyl-piperazine-1-carbonyl)-pyrrolidin-3-yl]-N-methyl-benzamide

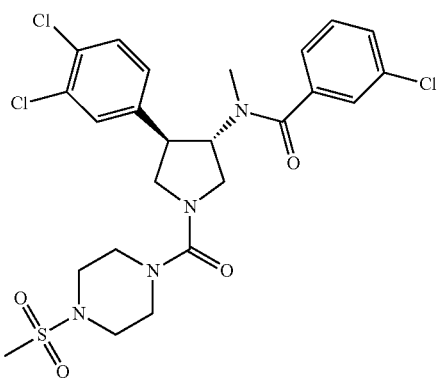 [SMILES: CN(C(=O)c1cccc(Cl)c1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Acid chloride: 3-Chloro-benzoyl chloride (commercially available), ES-MS m/e: 575.2 (M+H⁺).

EXAMPLE 12 rac-4-Chloro-N-[(3S,4R)-4-(3,4-dichloro-phenyl)-1-(4-methanesulfonyl-piperazine-1-carbonyl)-pyrrolidin-3-yl]-N-methyl-benzamide

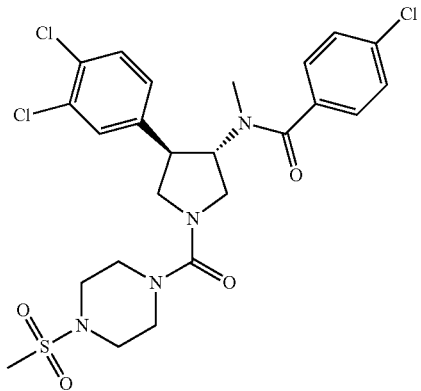 [SMILES: CN(C(=O)c1ccc(Cl)cc1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3), Acid chloride: 4-Chloro-benzoyl chloride (commercially available), ES-MS m/e: 575.2 (M+H⁺).

EXAMPLE 13 rac-4-Cyano-N-[(3S,4R)-4-(3,4-dichloro-phenyl)-1-(4-methanesulfonyl-piperazine-1-carbonyl)-pyrrolidin-3-yl]-N-methyl-benzamide

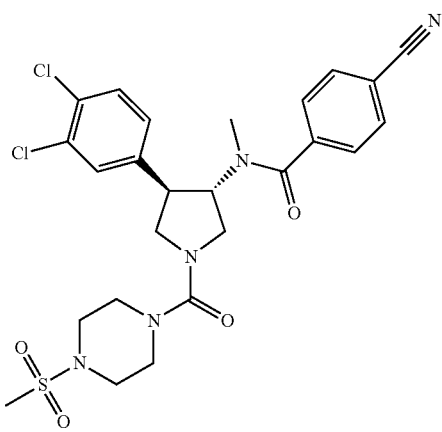 [SMILES: CN(C(=O)c1ccc(C#N)cc1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3), Acid chloride: 4-Cyano-benzoyl chloride (commercially available), ES-MS m/e: 564.3 (M+H⁺).

EXAMPLE 14 rac-N-[(3S,4R)-4-(3,4-Dichloro-phenyl)-1-(4-methanesulfonyl-piperazine-1-carbonyl)-pyrrolidin-3-yl]-4-ethyl-N-methyl-benzamide

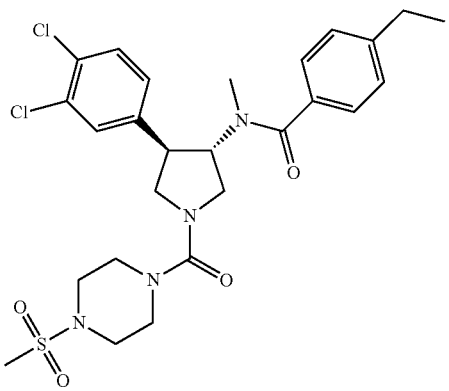 [SMILES: CCc1ccc(C(=O)N(C)[C@@H]2CN(C(=O)N3CCN(S(C)(=O)=O)CC3)C[C@H]2c2ccc(Cl)c(Cl)c2)cc1]

Coupling according to general procedure I:

Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3), Acid chloride: 4-Ethyl-benzoyl chloride (commercially available), ES-MS m/e: 567.3 (M+H⁺).

EXAMPLE 15 rac-3-Cyano-N-[(3S,4R)-4-(3,4-dichloro-phenyl)-1-(4-methanesulfonyl-piperazine-1-carbonyl)-pyrrolidin-3-yl]-N-methyl-benzamide

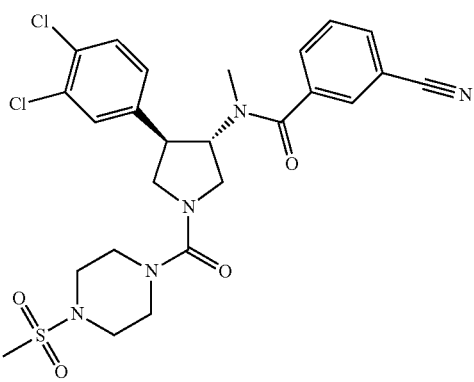 [SMILES: CN(C(=O)c1cccc(C#N)c1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3), Acid chloride: 3-Cyano-benzoyl chloride (commercially available), ES-MS m/e: 564.5 (M+H⁺).

EXAMPLE 16 rac-N-[(3S,4R)-4-(3,4-Dichloro-phenyl)-1-(4-methanesulfonyl-piperazine-1-carbonyl)-pyrrolidin-3-yl]-N-methyl-4-trifluoromethoxy-benzamide

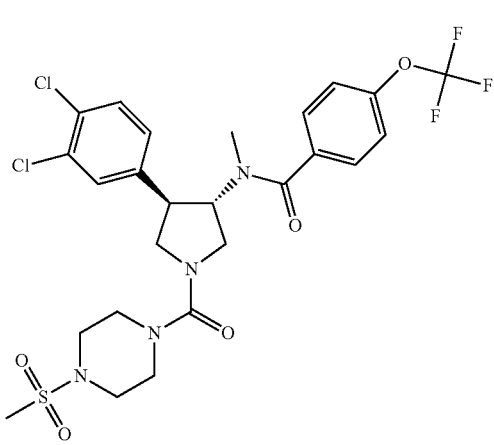 [SMILES: CN(C(=O)c1ccc(OC(F)(F)F)cc1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3),
Acid chloride: 4-Trifluoromethoxy-benzoyl chloride (commercially available), ES-MS m/e: 623.3 (M+H⁺).

EXAMPLE 17 rac-N-[(3S,4R)-4-(3,4-Dichloro-phenyl)-1-(4-methanesulfonyl-piperazine-1-carbonyl)-pyrrolidin-3-yl]-3-fluoro-N-methyl-benzamide

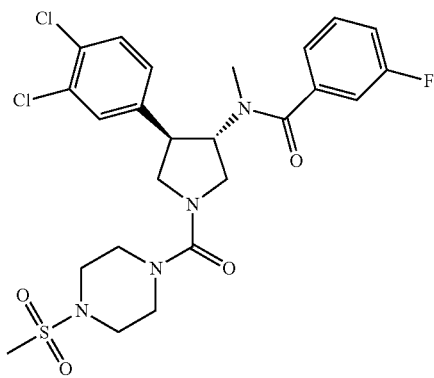 [SMILES: CN(C(=O)c1cccc(F)c1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Acid chloride: 3-Fluoro-benzoyl chloride (commercially available), ES-MS m/e: 557.2 (M+H⁺).

EXAMPLE 18 rac-N-[(3S,4R)-4-(3,4-Dichloro-phenyl)-1-(4-methanesulfonyl-piperazine-1-carbonyl)-pyrrolidin-3-yl]-3-fluoro-N-methyl-5-trifluoromethyl-benzamide

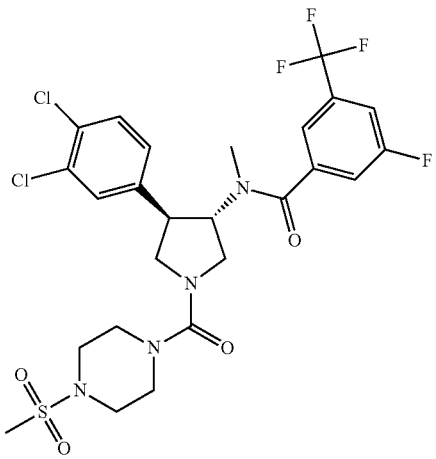 [SMILES: CN(C(=O)c1cc(F)cc(C(F)(F)F)c1)[C@@H]1CN(C(=O)N2CCN(S(C)(=O)=O)CC2)C[C@H]1c1ccc(Cl)c(Cl)c1]

Coupling according to general procedure I:
Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3),
Acid chloride: 3-Fluoro-5-trifluoromethyl-benzoyl chloride (commercially available), ES-MS m/e: 627.2 (M+H⁺).

EXAMPLE 19 rac-N-[(3S,4R)-4-(3,4-Dichloro-phenyl)-1-(4-methanesulfonyl-piperazine-1-carbonyl)-pyrrolidin-3-yl]-3,5-difluoro-N-methyl-benzamide

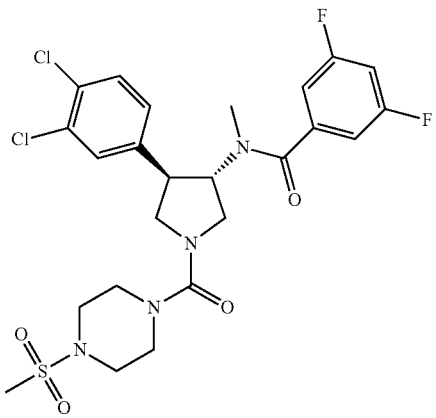 [SMILES: CN(C(=O)c1cc(F)cc(F)c1)[C@@H]1CN(C(=O)N2CCN(S(C)(=O)=O)CC2)C[C@H]1c1ccc(Cl)c(Cl)c1]

Coupling according to general procedure I:
Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Acid chloride: 3,5-Difluoro-benzoyl chloride (commercially available), ES-MS m/e: 575.3 (M+H⁺).

EXAMPLE 20 rac-N-[(3S,4R)-4-(3,4-Dichloro-phenyl)-1-(4-methanesulfonyl-piperazine-1-carbonyl)-pyrrolidin-3-yl]-3-fluoro-N-methyl-4-trifluoromethyl-benzamide

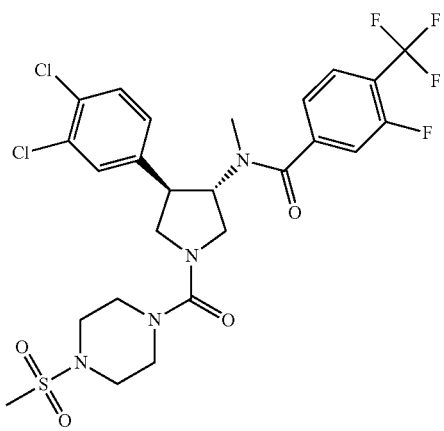 [SMILES: CN(C(=O)c1ccc(C(F)(F)F)c(F)c1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Acid chloride: 3-Fluoro-4-trifluoromethyl-benzoyl chloride (commercially available), ES-MS m/e: 627.3 (M+H⁺).

EXAMPLE 21 rac-3-Chloro-N-[(3S,4R)-4-(3,4-dichloro-phenyl)-1-(4-methanesulfonyl-piperazine-1-carbonyl)-pyrrolidin-3-yl]-2-fluoro-N-methyl-benzamide

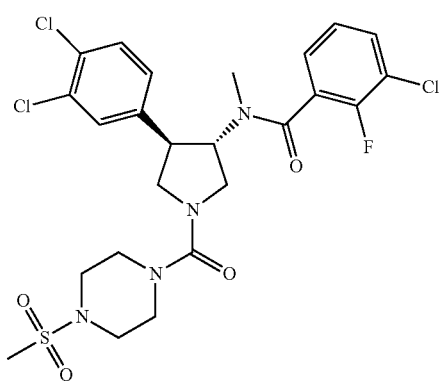 [SMILES: CN(C(=O)c1cccc(Cl)c1F)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Acid chloride: 3-Chloro-2-fluoro-benzoyl chloride (commercially available), ES-MS m/e: 591.3 (M+H⁺).

EXAMPLE 22 rac-N-[(3S,4R)-4-(3,4-Dichloro-phenyl)-1-(4-methanesulfonyl-piperazine-1-carbonyl)-pyrrolidin-3-yl]-2-fluoro-N-methyl-3-trifluoromethyl-benzamide

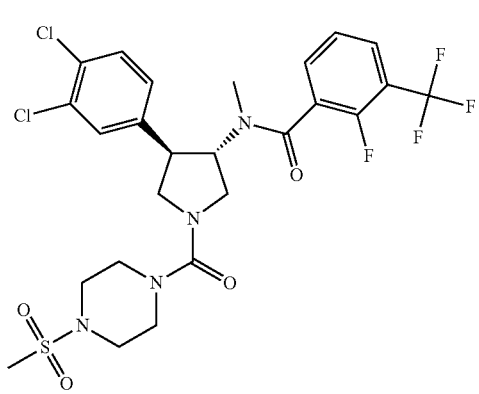 [SMILES: CN(C(=O)c1cccc(C(F)(F)F)c1F)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Acid chloride: 2-Fluoro-3-trifluoromethyl-benzoyl chloride (commercially available), ES-MS m/e: 627.2 (M+H⁺).

EXAMPLE 23 rac-Benzofuran-5-carboxylic acid [(3S,4R)-4-(3,4-dichloro-phenyl)-1-(4-methanesulfonyl-piperazine-1-carbonyl)-pyrrolidin-3-yl]-methyl-amide

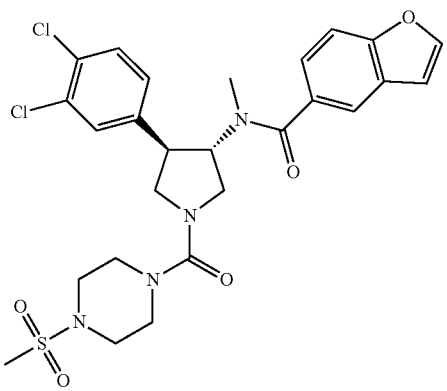 [SMILES: CN(C(=O)c1ccc2occc2c1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Acid chloride: Benzofuran-5-carbonyl chloride (commercially available), ES-MS m/e: 579.3 (M+H⁺).

EXAMPLE 24 rac-N-[(3S,4R)-4-(3,4-Dichloro-phenyl)-1-(4-methanesulfonyl-piperazine-1-carbonyl)-pyrrolidin-3-yl]-4-dimethylamino-N-methyl-benzamide

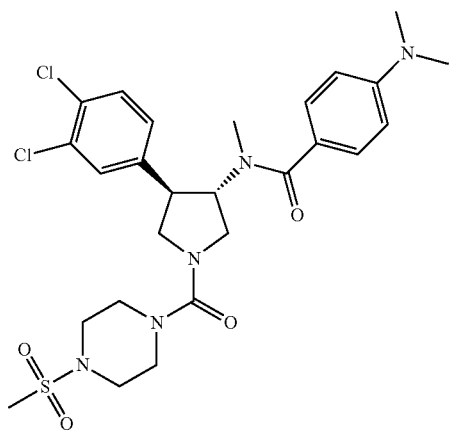

Coupling according to general procedure I:

Pyrrolidine intermediate: rac-[(3R,4S)-3-(3,4-Dichlorophenyl)-4-methylamino-pyrrolidin-1-yl]-(4-methanesulfonyl-piperazin-1-yl)-methanone (XI-3), Acid chloride: 4-Dimethylamino-benzoyl chloride (commercially available), ES-MS m/e: 582.2 (M+H⁺).

EXAMPLE 25 rac-N-[(3S,4R)-4-(3,4-Dichloro-phenyl)-1-(4-methanesulfonyl-piperazine-1-carbonyl)-pyrrolidin-3-yl]-4-fluoro-3,N-dimethyl-benzamide

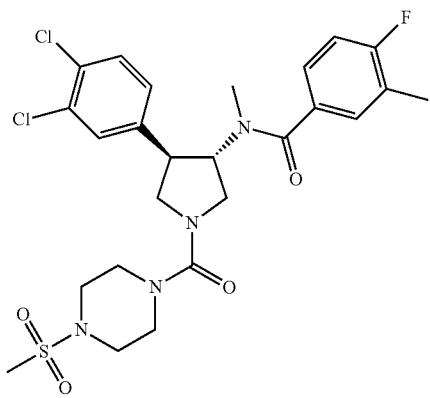

Coupling according to general procedure I:

Pyrrolidine intermediate: rac-[(3R,4S)-3-(3,4-Dichlorophenyl)-4-methylamino-pyrrolidin-1-yl]-(4-methanesulfonyl-piperazin-1-yl)-methanone (XI-3), Acid chloride: 4-Fluoro-3-methyl-benzoyl chloride (commercially available), ES-MS m/e: 571.3 (M+H⁺).

EXAMPLE 26 rac-N-[(3S,4R)-4-(3,4-Dichloro-phenyl)-1-(4-methanesulfonyl-piperazine-1-carbonyl)-pyrrolidin-3-yl]-3-fluoro-4-methoxy-N-methyl-benzamide

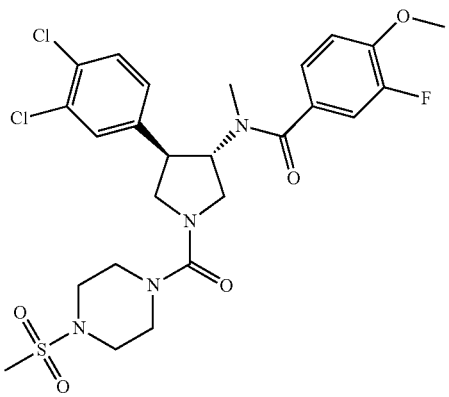

Coupling according to general procedure II:

Pyrrolidine intermediate: rac-[(3R,4S)-3-(3,4-Dichlorophenyl)-4-methylamino-pyrrolidin-1-yl]-(4-methanesulfonyl-piperazin-1-yl)-methanone (XI-3), Carboxylic acid: 3-Fluoro-4-methoxy-benzoic acid (commercially available), ES-MS m/e: 587.1 (M+H⁺).

EXAMPLE 27 rac-N-[(3S,4R)-4-(3,4-Dichloro-phenyl)-1-(4-methanesulfonyl-piperazine-1-carbonyl)-pyrrolidin-3-yl]-3,4-difluoro-N-methyl-benzamide

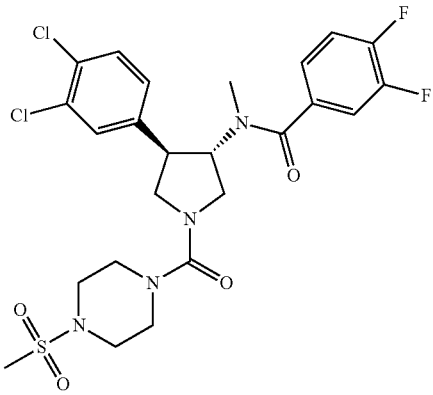 [SMILES: CN(C(=O)c1ccc(F)c(F)c1)[C@@H]1CN(C(=O)N2CCN(S(C)(=O)=O)CC2)C[C@H]1c1ccc(Cl)c(Cl)c1]

Coupling according to general procedure II:

Pyrrolidine intermediate: rac-[(3R,4S)-3-(3,4-Dichlorophenyl)-4-methylamino-pyrrolidin-1-yl]-(4-methanesulfonyl-piperazin-1-yl)-methanone (XI-3), Carboxylic acid: 3,4-Difluoro-benzoic acid (commercially available), ES-MS m/e: 575.2 (M+H⁺).

EXAMPLE 28 rac-2,2-Difluoro-benzo[1,3]dioxole-5-carboxylic acid [(3S,4R)-4-(3,4-dichloro-phenyl)-1-(4-methane-sulfonyl-piperazine-1-carbonyl)-pyrrolidin-3-yl]-methyl-amide

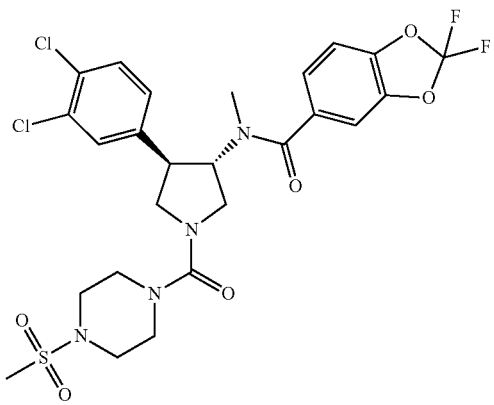 [SMILES: CN(C(=O)c1ccc2c(c1)OC(F)(F)O2)[C@@H]1CN(C(=O)N2CCN(S(C)(=O)=O)CC2)C[C@H]1c1ccc(Cl)c(Cl)c1]

Coupling according to general procedure II:
Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3),
Carboxylic acid: 2,2-Difluoro-benzo[1,3]dioxole-5-carboxylic acid (commercially available), ES-MS m/e: 619.3 (M+H⁺).

EXAMPLE 29 rac-N-[(3S,4R)-4-(3,4-Dichloro-phenyl)-1-(4-methanesulfonyl-piperazine-1-carbonyl)-pyrrolidin-3-yl]-N-methyl-4-(2,2,2-trifluoro-acetylamino)-benzamide

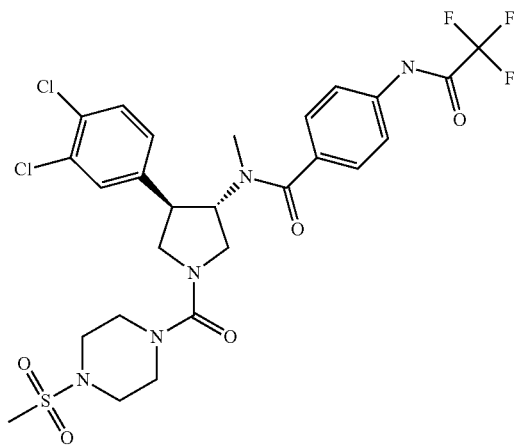 [SMILES: CN(C(=O)c1ccc(NC(=O)C(F)(F)F)cc1)[C@@H]1CN(C(=O)N2CCN(S(C)(=O)=O)CC2)C[C@H]1c1ccc(Cl)c(Cl)c1]

Coupling according to general procedure II:
Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3),
Carboxylic acid: 4-(2,2,2-Trifluoro-acetylamino)-benzoic acid (commercially available), ES-MS m/e: 650.3 (M+H⁺).

EXAMPLE 30 rac-N-[(3S,4R)-4-(3,4-Dichloro-phenyl)-1-(4-methanesulfonyl-piperazine-1-carbonyl)-pyrrolidin-3-yl]-N-methyl-4-pyrrol-1-yl-benzamide

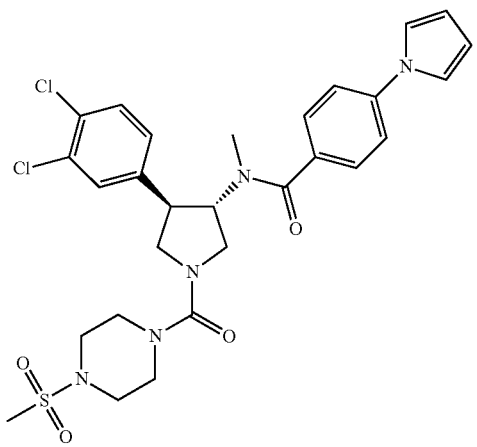 [SMILES: CN(C(=O)c1ccc(-n2cccc2)cc1)[C@@H]1CN(C(=O)N2CCN(S(C)(=O)=O)CC2)C[C@H]1c1ccc(Cl)c(Cl)c1]

Coupling according to general procedure II:
Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3),
Carboxylic acid: 4-Pyrrol-1-yl-benzoic acid (commercially available), ES-MS m/e: 604.3 (M+H⁺).

EXAMPLE 31 rac-2,3-Dihydro-benzofuran-5-carboxylic acid [(3S,4R)-4-(3,4-dichloro-phenyl)-1-(4-methanesulfonyl-piperazine-1-carbonyl)-pyrrolidin-3-yl]-methyl-amide

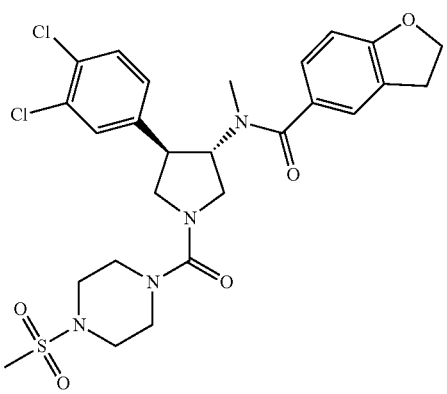 [SMILES: CN(C(=O)c1ccc2c(c1)CCO2)[C@@H]1CN(C(=O)N2CCN(S(C)(=O)=O)CC2)C[C@H]1c1ccc(Cl)c(Cl)c1]

Coupling according to general procedure II:
Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3), Carboxylic acid: 2,3-Dihydro-benzofuran-5-carboxylic acid (commercially available), ES-MS m/e: 581.2 (M+H$^+$).

EXAMPLE 32 rac-3-Chloro-N-[(3S,4R)-4-(3,4-dichloro-phenyl)-1-(4-methanesulfonyl-piperazine-1-carbonyl)-pyrrolidin-3-yl]-4-fluoro-N-methyl-benzamide

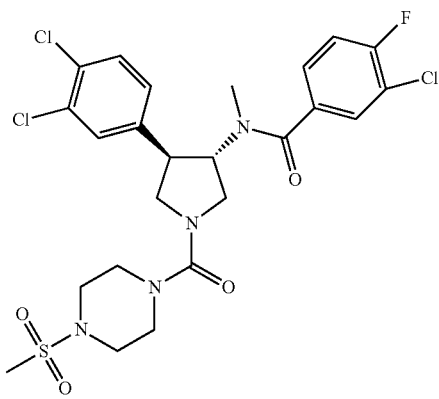 [SMILES: CN(C(=O)c1ccc(F)c(Cl)c1)[C@@H]1CN(C(=O)N2CCN(S(C)(=O)=O)CC2)C[C@H]1c1ccc(Cl)c(Cl)c1]

Coupling according to general procedure II:

Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3), Carboxylic acid: 3-Chloro-4-fluoro-benzoic acid (commercially available), ES-MS m/e: 593.3 (M+H$^+$).

EXAMPLE 33 rac-3-Chloro-N-[(3S,4R)-4-(3,4-dichloro-phenyl)-1-(4-methanesulfonyl-piperazine-1-carbonyl)-pyrrolidin-3-yl]-4-methoxy-N-methyl-benzamide

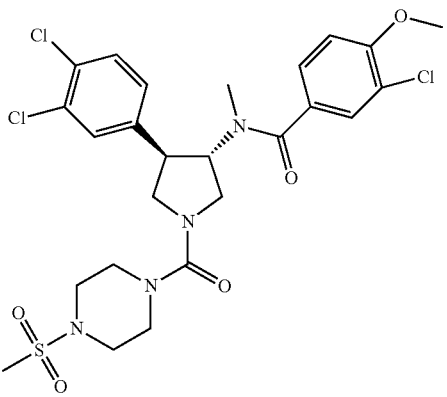

Coupling according to general procedure II:

Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3), Carboxylic acid: 3-Chloro-4-methoxy-benzoic acid (commercially available), ES-MS m/e: 605.3 (M+H$^+$).

EXAMPLE 34 rac-Quinoxaline-6-carboxylic acid [(3S,4R)-4-(3,4-dichloro-phenyl)-1-(4-methanesulfonyl-piperazine-1-carbonyl)-pyrrolidin-3-yl]-methyl-amide

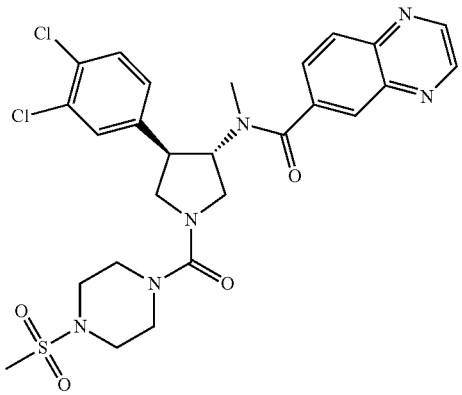 [SMILES: CN(C(=O)c1ccc2nccnc2c1)[C@@H]1CN(C(=O)N2CCN(S(C)(=O)=O)CC2)C[C@H]1c1ccc(Cl)c(Cl)c1]

Coupling according to general procedure II:

Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3), Carboxylic acid: Quinoxaline-6-carboxylic acid (commercially available), ES-MS m/e: 591.3 (M+H$^+$).

EXAMPLE 35 rac-3-(Cyano-methyl-methyl)-N-[(3S,4R)-4-(3,4-dichloro-phenyl)-1-(4-methanesulfonyl-piperazine-1-carbonyl)-pyrrolidin-3-yl]-N-methyl-benzamide

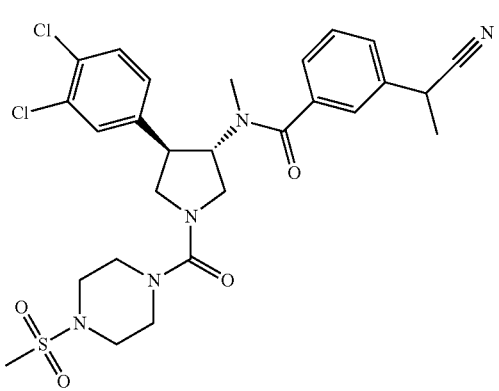 [SMILES: CC(C#N)c1cccc(C(=O)N(C)[C@@H]2CN(C(=O)N3CCN(S(C)(=O)=O)CC3)C[C@H]2c2ccc(Cl)c(Cl)c2)c1]

Coupling according to general procedure II:

Pyrrolidine intermediate: rac-[(3R,4S)-3-(3,4-Dichloro-phenyl)-4-methylamino-pyrrolidin-1-yl]-(4-methane-sulfonyl-piperazin-1-yl)-methanone (XI-3), Carboxylic acid: 3-(Cyano-methyl-methyl)-benzoic acid (commercially available), ES-MS m/e: 592.5 (M+H⁺).

EXAMPLE 36 rac-N-[(3S,4R)-4-(3,4-Dichloro-phenyl)-1-(4-methanesulfonyl-piperazine-1-carbonyl)-pyrrolidin-3-yl]-4-fluoro-N-methyl-3-trifluoromethyl-benzamide

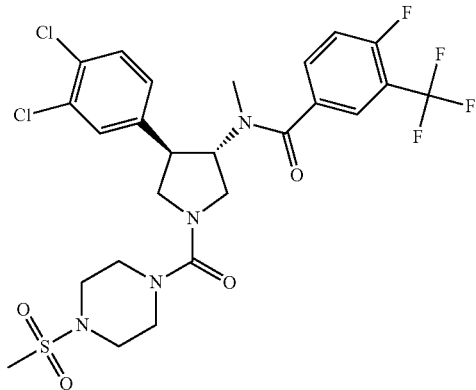 [SMILES: CN(C(=O)c1ccc(F)c(C(F)(F)F)c1)[C@@H]1CN(C(=O)N2CCN(S(C)(=O)=O)CC2)C[C@H]1c1ccc(Cl)c(Cl)c1]

Coupling according to general procedure II:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Carboxylic acid: 4-Fluoro-3-trifluoromethyl-benzoic acid (commercially available), ES-MS m/e: 625.1 (M+H⁺).

EXAMPLE 37 rac-N-[(3S,4R)-4-(3,4-Dichloro-phenyl)-1-(4-methanesulfonyl-piperazine-1-carbonyl)-pyrrolidin-3-yl]-4-methoxy-N-methyl-benzamide

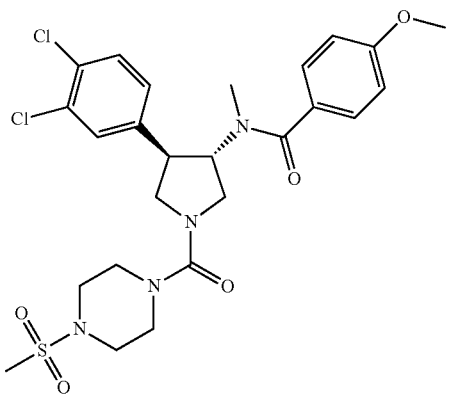

Coupling according to general procedure II:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Carboxylic acid: 4-Methoxy-benzoic acid (commercially available), ES-MS m/e: 569.3 (M+H⁺).

EXAMPLE 38 rac-N-[(3S,4R)-4-(3,4-Dichloro-phenyl)-1-(4-methanesulfonyl-piperazine-1-carbonyl)-pyrrolidin-3-yl]-2-fluoro-N-methyl-5-trifluoromethyl-benzamide

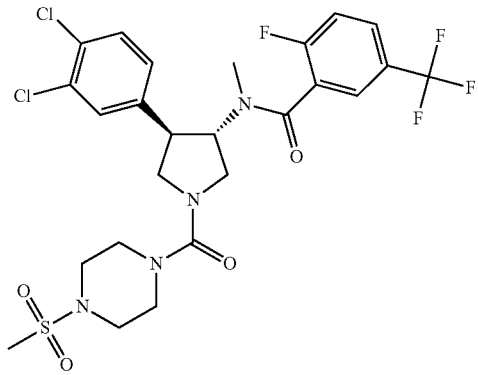 [SMILES: CN(C(=O)c1cc(C(F)(F)F)ccc1F)[C@@H]1CN(C(=O)N2CCN(S(C)(=O)=O)CC2)C[C@H]1c1ccc(Cl)c(Cl)c1]

Coupling according to general procedure II:

Pyrrolidine intermediate: rac-[(3R,4S)-3-(3,4-Dichloro-phenyl)-4-methylamino-pyrrolidin-1-yl]-(4-methanesulfonyl-piperazin-1-yl)-methanone (XI-3), Carboxylic acid: 2-Fluoro-5-trifluoromethyl-benzoic acid (commercially available), ES-MS m/e: 625.1 (M+H⁺).

EXAMPLE 39 rac-N-[(3S,4R)-4-(3,4-Dichloro-phenyl)-1-(4-methanesulfonyl-piperazine-1-carbonyl)-pyrrolidin-3-yl]-N-ethyl-4-methoxy-3-trifluoromethyl-benzamide

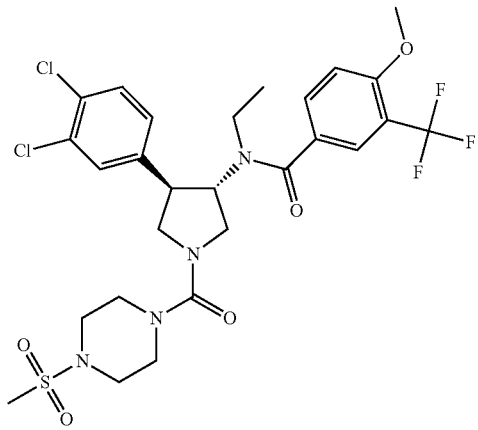 [SMILES: CCN(C(=O)c1ccc(OC)c(C(F)(F)F)c1)[C@@H]1CN(C(=O)N2CCN(S(C)(=O)=O)CC2)C[C@H]1c1ccc(Cl)c(Cl)c1]

Coupling according to general procedure I:

Pyrrolidine intermediate: rac-[(3R,4S)-3-(3,4-Dichloro-phenyl)-4-ethylamino-pyrrolidin-1-yl]-(4-methanesulfonyl-piperazin-1-yl)-methanone (XI-4), Acid chloride: 4-Methoxy-3-trifluoromethyl-benzoyl chloride (commercially available), ES-MS m/e: 650.8 (M+H⁺).

EXAMPLE 40 rac-N-[(3S,4R)-4-(3,4-Dichloro-phenyl)-1-(4-methanesulfonyl-piperazine-1-carbonyl)-pyrrolidin-3-yl]-N-ethyl-2-fluoro-5-trifluoromethyl-benzamide

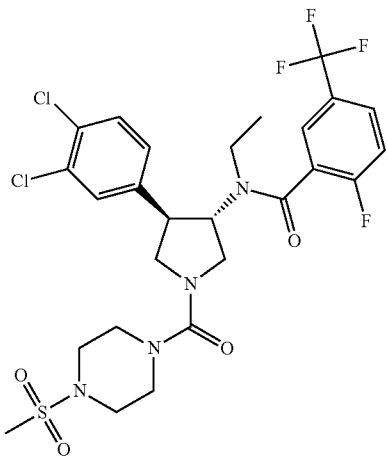 [SMILES: CCN(C(=O)c1cc(C(F)(F)F)ccc1F)[C@@H]1CN(C(=O)N2CCN(S(C)(=O)=O)CC2)C[C@H]1c1ccc(Cl)c(Cl)c1]

Coupling according to general procedure I:
Pyrrolidine intermediate: rac-[(3R,4S)-3-(3,4-Dichlorophenyl)-4-ethylamino-pyrrolidin-1-yl]-(4-methanesulfonyl-piperazin-1-yl)-methanone (XI-4),
Acid chloride: 2-Fluoro-5-trifluoromethyl-benzoyl chloride (commercially available), ES-MS m/e: 638.7 (M+H⁺).

EXAMPLE 41 rac-N-[(3S,4R)-1-(4-Cyano-benzoyl)-4-(3,4-dichloro-phenyl)-pyrrolidin-3-yl]-4-methoxy-N-methyl-3-trifluoromethyl-benzamide

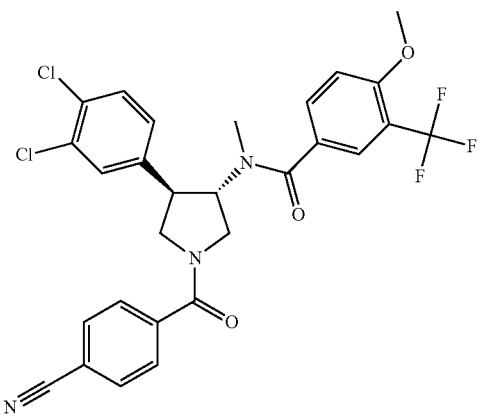 [SMILES: COc1ccc(C(=O)N(C)[C@@H]2CN(C(=O)c3ccc(C#N)cc3)C[C@H]2c2ccc(Cl)c(Cl)c2)cc1C(F)(F)F]

Coupling according to general procedure I:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1), Acid chloride: 4-Cyano-benzoyl chloride (commercially available), ES-MS m/e: 576.3 (M+H⁺).

EXAMPLE 42

N-[(3S,4R)-4-(3,4-Dichloro-phenyl)-1-(S)-4-methanesulfonyl-3-methyl-piperazine-1-carbonyl)-pyrrolidin-3-yl]-4-methoxy-N-methyl-3-trifluoromethyl-benzamide

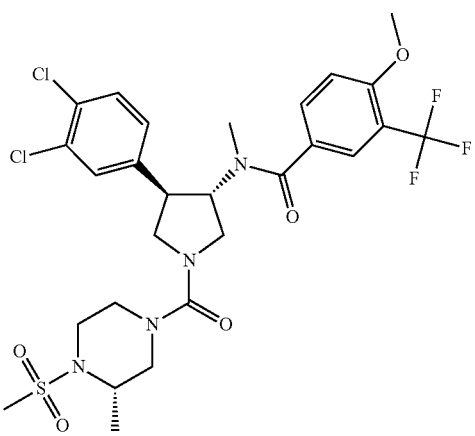 [SMILES: COc1ccc(C(=O)N(C)[C@@H]2CN(C(=O)N3CCN(S(C)(=O)=O)[C@@H](C)C3)C[C@H]2c2ccc(Cl)c(Cl)c2)cc1C(F)(F)F]

Coupling according to general procedure I:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1),
Carbamoyl chloride: (S)-4-Methanesulfonyl-3-methyl-piperazine-1-carbonyl chloride ES-MS m/e: 651.3 (M+H⁺).

(S)-4-Methanesulfonyl-3-methyl-piperazine-1-carbonyl chloride

First step: To a stirred solution of commercially available (S)-3-methyl-piperazine-1-carboxylic acid tert-butyl ester (2.38 g, 12 mmol) in CH$_2$Cl$_2$ (25 mL) at 0° C. were added pyridine (1.91 mL, 24 mmol) and methanesulfonyl chloride (0.92 mL, 12 mmol). Stirring was continued at RT overnight, the reaction was poured onto water and extracted with CH$_2$Cl$_2$. The combined organic phases were dried on Na$_2$SO$_4$ and concentrated under vacuo. The crude product was dissolved in CH$_2$Cl$_2$ (20 mL) and TFA (4 mL) was added. After 2 hours at RT, the volatiles were removed under vacuo, the crude was dissolved in CH$_2$Cl$_2$ and washed with aq. NaHCO$_3$ (until pH=8). The organic phase was dried on Na$_2$SO$_4$ and concentrated under vacuo to yield 0.83 g (39%) of (s)-1-methanesulfonyl-2-methyl-piperazine as a light yellow oil.

Second step: To a stirred solution of carbonic acid ditrichloromethyl ester (triphosgene) (560 mg, 1.88 mmol) in CH$_2$Cl$_2$ (10 mL) at −78° C., was added a solution of (S)-1-methanesulfonyl-2-methyl-piperazine (838 mg, 4.70 mmol) and pyridine (0.74 mL, 9.4 mmol) in CH$_2$Cl$_2$ (10 mL) over 1 hour. The temperature was raised to RT, and stirring was continued over night. The organic phase was washed with H$_2$O, dried over Na$_2$SO$_4$. Concentration under vacuo and flash chromatography (SiO$_2$, EtOAc/H, 1:1) yielded 0.70 g (62%) of (S)-4-methanesulfonyl-3-methyl-piperazine-1-carbonylchloride as a light yellow solid.

EXAMPLE 43

N-[(3S,4R)-4-(3,4-Dichloro-phenyl)-1-(R)-4-methanesulfonyl-3-methyl-piperazine-1-carbonyl)-pyrrolidin-3-yl]-4-methoxy-N-methyl-3-trifluoromethyl-benzamide

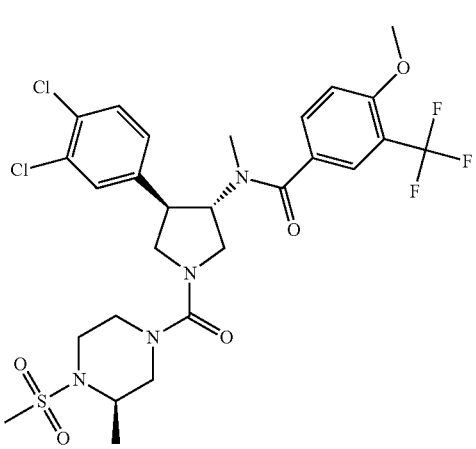 [SMILES: COc1ccc(C(=O)N(C)[C@@H]2CN(C(=O)N3CCN(S(C)(=O)=O)[C@H](C)C3)C[C@H]2c2ccc(Cl)c(Cl)c2)cc1C(F)(F)F]

Coupling according to general procedure I:

Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1), Carbamoyl chloride: (R)-4-Methanesulfonyl-3-methyl-piperazine-1-carbonyl chloride ES-MS m/e: 651.3 (M+H$^+$).

(R)-4-Methanesulfonyl-3-methyl-piperazine-1-carbonyl chloride

First step: To a stirred solution of commercially available (R)-3-methyl-piperazine-1-carboxylic acid tert-butyl ester (8.78 g, 44 mmol) in CH$_2$Cl$_2$ (80 mL) at 0° C. were added Et$_3$N (12.15 mL, 88 mmol) and methanesulfonyl chloride (5.09 mL, 66 mmol). Stirring was continued at RT overnight, the reaction was poured onto water and extracted with CH$_2$Cl$_2$. The combined organic phases were dried on Na$_2$SO$_4$ and concentrated under vacuo. The crude product was dissolved in CH$_2$Cl$_2$ (50 mL) and TFA (15 mL) was added. After 2 hours at RT, the volatiles were removed under vacuo, the crude was dissolved in CH$_2$Cl$_2$ and washed with aq. NaHCO$_3$ (until pH=8). The organic phase was dried on Na$_2$SO$_4$ and concentrated under vacuo to yield 2.63 g (34%) of (R)-1-methanesulfonyl-2-methyl-piperazine as a light yellow oil.

Second step: To a stirred solution of carbonic acid ditrichloromethyl ester (triphosgene) (1.17 g, 3.95 mmol) in CH$_2$Cl$_2$ (20 mL) at −78° C., was added a solution of (R)-1-methanesulfonyl-2-methyl-piperazine (1.76 g, 9.9 mmol) and pyridine (1.60 mL, 20 mmol) in CH$_2$Cl$_2$ (20 mL) over 1 hour. The temperature was raised to RT, and stirring was continued over night. The organic phase was washed with H$_2$O, dried over Na$_2$SO$_4$. Concentration under vacuo and flash chromatography (SiO$_2$, EtOAc/H, 1:1) yielded 1.70 g (71%) of (R)-4-methanesulfonyl-3-methyl-piperazine-1-carbonyl chloride as a light yellow solid.

EXAMPLE 44 rac-N-[(3S,4R)-4-(3,4-Dichloro-phenyl)-1-(4-methoxy-benzoyl)-pyrrolidin-3-yl]-4-methoxy-N-methyl-3-trifluoromethyl-benzamide

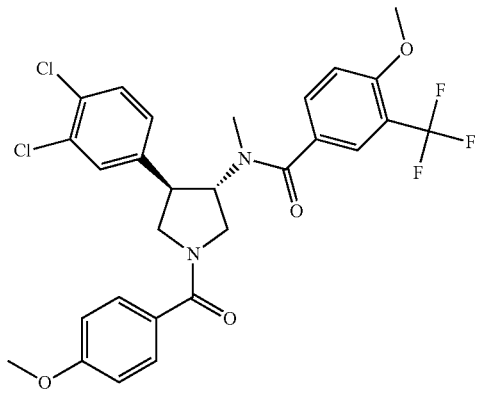 [SMILES: COc1ccc(C(=O)N2C[C@@H](N(C)C(=O)c3ccc(OC)c(C(F)(F)F)c3)[C@H](c3ccc(Cl)c(Cl)c3)C2)cc1]

Coupling according to general procedure I:

Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1), Acid chloride: 4-Methoxy-benzoyl chloride (commercially available), ES-MS m/e: 580.8 (M+H$^+$).

EXAMPLE 45 rac-N-[(3S,4R)-4-(3,4-Dichloro-phenyl)-1-(4-dimethylamino-benzoyl)-pyrrolidin-3-yl]-4-methoxy-N-methyl-3-trifluoromethyl-benzamide

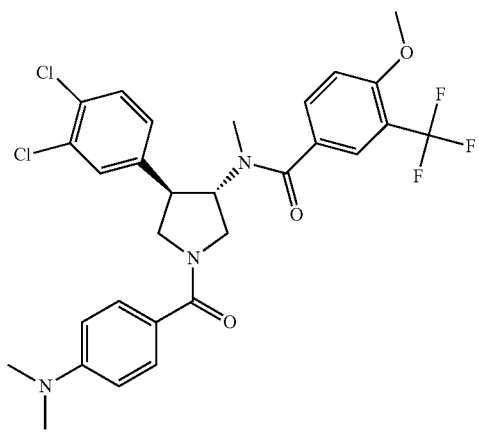 [SMILES: COc1ccc(C(=O)N(C)[C@@H]2CN(C(=O)c3ccc(N(C)C)cc3)C[C@H]2c2ccc(Cl)c(Cl)c2)cc1C(F)(F)F]

Coupling according to general procedure I:

Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1), Acid chloride: 4-Dimethylamino-benzoyl chloride (commercially available), ES-MS m/e: 593.7 (M+H⁺).

EXAMPLE 46 rac-N-[(3S,4R)-4-(3,4-Dichloro-phenyl)-1-(4-fluoro-benzoyl)-pyrrolidin-3-yl]-4-methoxy-N-methyl-3-trifluoromethyl-benzamide

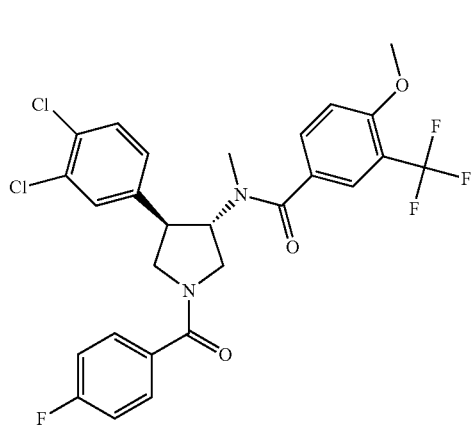 [SMILES: COc1ccc(C(=O)N(C)[C@@H]2CN(C(=O)c3ccc(F)cc3)C[C@H]2c2ccc(Cl)c(Cl)c2)cc1C(F)(F)F]

Coupling according to general procedure I:

Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1), Acid chloride: 4-Fluoro-benzoyl chloride (commercially available), ES-MS m/e: 568.7 (M+H⁺).

EXAMPLE 47 rac-N-[(3S,4R)-1-(3-Cyano-benzoyl)-4-(3,4-dichloro-phenyl)-pyrrolidin-3-yl]-4-methoxy-N-methyl-3-trifluoromethyl-benzamide

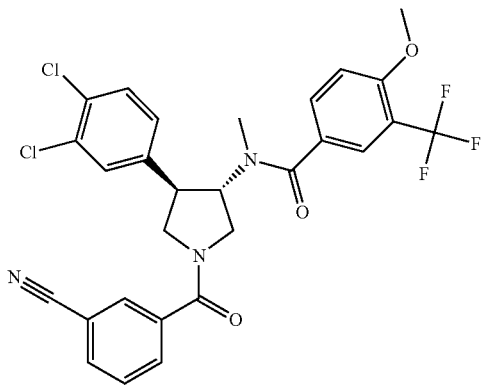 [SMILES: COc1ccc(C(=O)N(C)[C@@H]2CN(C(=O)c3cccc(C#N)c3)C[C@H]2c2ccc(Cl)c(Cl)c2)cc1C(F)(F)F]

Coupling according to general procedure I:

Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1), Acid chloride: 3-Cyano-benzoyl chloride (commercially available), ES-MS m/e: 575.8 (M+H⁺).

EXAMPLE 48 rac-N-[(3S,4R)-1-(Benzofuran-5-carbonyl)-4-(3,4-dichloro-phenyl)-pyrrolidin-3-yl]-4-methoxy-N-methyl-3-trifluoromethyl-benzamide

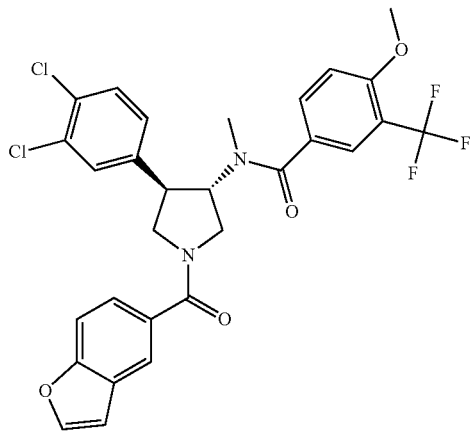 [SMILES: COc1ccc(C(=O)N(C)[C@@H]2CN(C(=O)c3ccc4occc4c3)C[C@H]2c2ccc(Cl)c(Cl)c2)cc1C(F)(F)F]

Coupling according to general procedure I:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1),
Acid chloride: Benzofuran-5-carbonyl chloride (commercially available), ES-MS m/e: 590.8 (M+H⁺).

EXAMPLE 49 rac-N-[(3S,4R)-4-(3,4-Dichloro-phenyl)-1-(2-fluoro-5-methanesulfonyl-benzoyl)-pyrrolidin-3-yl]-4-methoxy-N-methyl-3-trifluoromethyl-benzamide

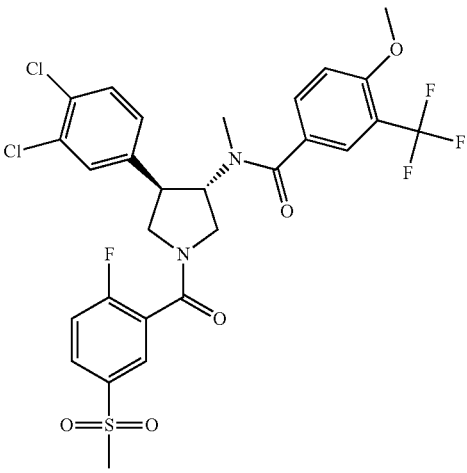 [SMILES: COc1ccc(C(=O)N(C)[C@@H]2CN(C(=O)c3cc(S(C)(=O)=O)ccc3F)C[C@H]2c2ccc(Cl)c(Cl)c2)cc1C(F)(F)F]

Coupling according to general procedure I:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1), Acid chloride: 2-Fluoro-5-methanesulfonyl-benzoyl chloride (commercially available), ES-MS m/e: 646.8 (M+H⁺).

EXAMPLE 50 rac-N-[(3S,4R)-4-(3,4-Dichloro-phenyl)-1-(4-trifluoromethyl-benzoyl)-pyrrolidin-3-yl]-4-methoxy-N-methyl-3-trifluoromethyl-benzamide

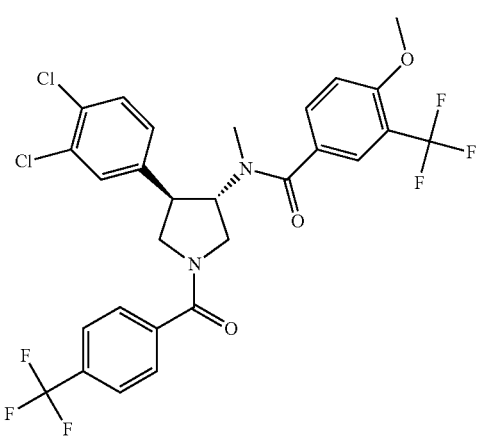 [SMILES: COc1ccc(C(=O)N(C)[C@@H]2CN(C(=O)c3ccc(C(F)(F)F)cc3)C[C@H]2c2ccc(Cl)c(Cl)c2)cc1C(F)(F)F]

Coupling according to general procedure I:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1),
Acid chloride: 4-Trifluoromethyl-benzoyl chloride (commercially available), ES-MS m/e: 618.7 (M+H⁺).

EXAMPLE 51 rac-N-[(3S,4R)-4-(3,4-Dichloro-phenyl)-1-(pyridine-4-carbonyl)-pyrrolidin-3-yl]-4-methoxy-N-methyl-3-trifluoromethyl-benzamide

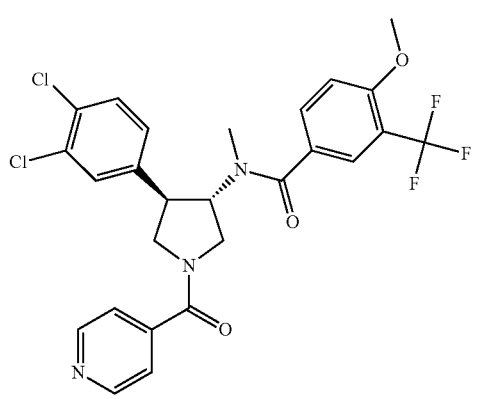 [SMILES: COc1ccc(C(=O)N(C)[C@@H]2CN(C(=O)c3ccncc3)C[C@H]2c2ccc(Cl)c(Cl)c2)cc1C(F)(F)F]

Coupling according to general procedure I:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1),
Acid chloride: Isonicotinoyl chloride (commercially available), ES-MS m/e: 551.7 (M+H⁺).

EXAMPLE 52 rac-N-[(3S,4R)-4-(3,4-Dichloro-phenyl)-1-(2,6-dichloro-pyridine-4-carbonyl)-pyrrolidin-3-yl]-4-methoxy-N-methyl-3-trifluoromethyl-benzamide

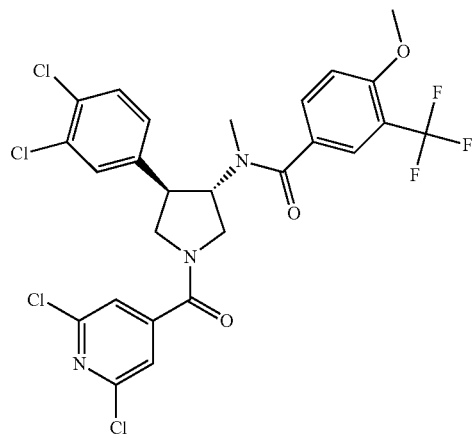 [SMILES: COc1ccc(C(=O)N(C)[C@@H]2CN(C(=O)c3cc(Cl)nc(Cl)c3)C[C@H]2c2ccc(Cl)c(Cl)c2)cc1C(F)(F)F]

Coupling according to general procedure I:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1),
Acid chloride: 2,6-Dichloro-isonicotinoyl chloride (commercially available), ES-MS m/e: 621.6 (M+H⁺).

EXAMPLE 53 rac-N-[(3S,4R)-4-(3,4-Dichloro-phenyl)-1-(4-trifluoromethoxy-benzoyl)-pyrrolidin-3-yl]-4-methoxy-N-methyl-3-trifluoromethyl-benzamide

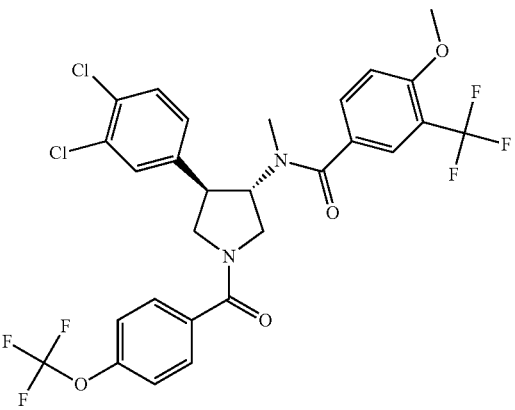 [SMILES: COc1ccc(C(=O)N(C)[C@@H]2CN(C(=O)c3ccc(OC(F)(F)F)cc3)C[C@H]2c2ccc(Cl)c(Cl)c2)cc1C(F)(F)F]

Coupling according to general procedure I:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1), Acid chloride: 4-Trifluoromethoxy-benzoyl chloride (commercially available), ES-MS m/e: 634.5 (M+H⁺).

EXAMPLE 54 rac-N-[(3S,4R)-4-(3,4-Dichloro-phenyl)-1-(3-methanesulfonyl-benzoyl)-pyrrolidin-3-yl]-4-methoxy-N-methyl-3-trifluoromethyl-benzamide

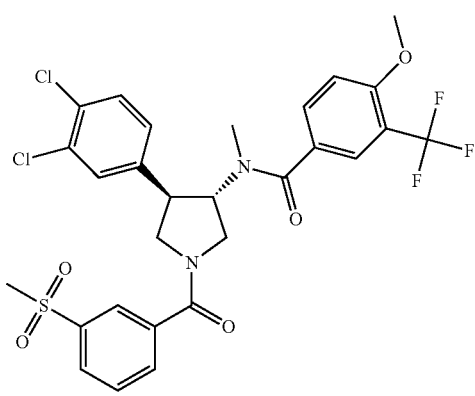 [SMILES: COc1ccc(C(=O)N(C)[C@@H]2CN(C(=O)c3cccc(S(C)(=O)=O)c3)C[C@H]2c2ccc(Cl)c(Cl)c2)cc1C(F)(F)F]

Coupling according to general procedure II:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1),
Carboxylic acid: 3-Methanesulfonyl-benzoic acid (commercially available), ES-MS m/e: 628.8 (M+H⁺).

EXAMPLE 55 rac-N-[(3S,4R)-4-(3,4-Dichloro-phenyl)-1-(4-methoxy-3-methyl-benzoyl)-pyrrolidin-3-yl]-4-methoxy-N-methyl-3-trifluoromethyl-benzamide

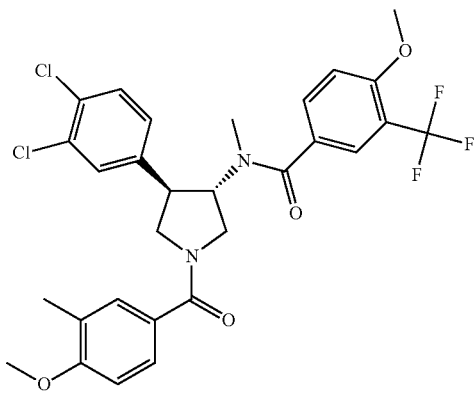 [SMILES: COc1ccc(C(=O)N2C[C@@H](N(C)C(=O)c3ccc(OC)c(C(F)(F)F)c3)[C@H](c3ccc(Cl)c(Cl)c3)C2)cc1C]

Coupling according to general procedure II:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1), Carboxylic acid: 4-Methoxy-3-methyl-benzoic acid (commercially available), ES-MS m/e: 594.8 (M+H⁺).

EXAMPLE 56 rac-N-[(3S,4R)-4-(3,4-Dichloro-phenyl)-1-(3,5-dimethyl-benzoyl)-pyrrolidin-3-yl]-4-methoxy-N-methyl-3-trifluoromethyl-benzamide

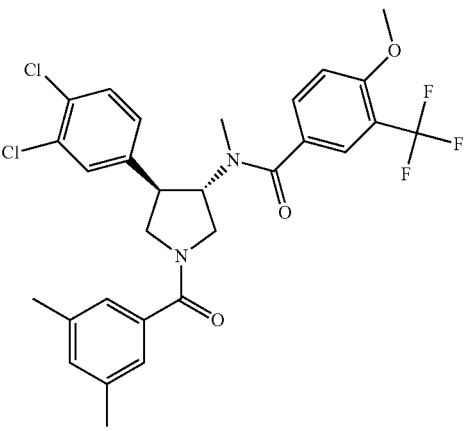 [SMILES: COc1ccc(C(=O)N(C)[C@@H]2CN(C(=O)c3cc(C)cc(C)c3)C[C@H]2c2ccc(Cl)c(Cl)c2)cc1C(F)(F)F]

Coupling according to general procedure II:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1),
Carboxylic acid: 3,5-Dimethyl-benzoic acid (commercially available), ES-MS m/e: 578.7 (M+H⁺).

EXAMPLE 57 rac-N-[(3S,4R)-1-(4-Acetyl-benzoyl)-4-(3,4-dichloro-phenyl)-pyrrolidin-3-yl]-4-methoxy-N-methyl-3-trifluoromethyl-benzamide

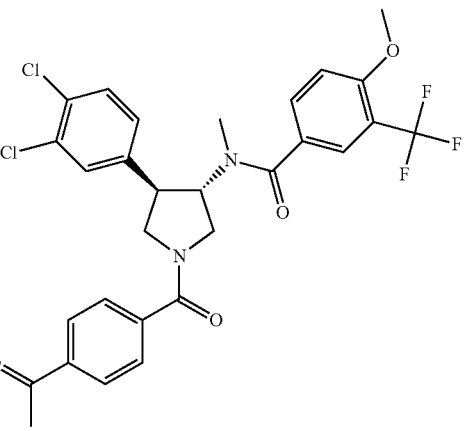

Coupling according to general procedure II:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1), Carboxylic acid: 4-Acetyl-benzoic acid (commercially available), ES-MS m/e: 592.8 (M+H⁺).

EXAMPLE 58 rac-N-[(3S,4R)-4-(3,4-Dichloro-phenyl)-1-(1,5-dimethyl-1H-pyrazole-3-carbonyl)-pyrrolidin-3-yl]-4-methoxy-N-methyl-3-trifluoromethyl-benzamide

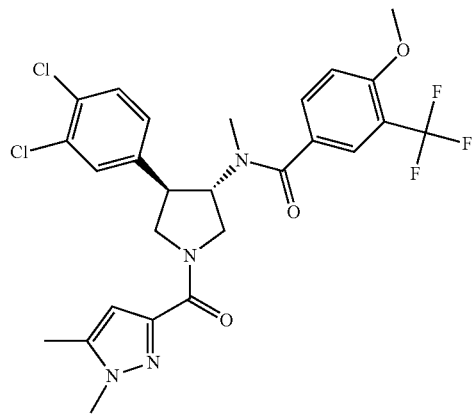 [SMILES: COc1ccc(C(=O)N(C)[C@@H]2CN(C(=O)c3cc(C)n(C)n3)C[C@H]2c2ccc(Cl)c(Cl)c2)cc1C(F)(F)F]

Coupling according to general procedure II:
Pyrrolidine intermediate: rac-N-[(3S,4R)-4-(3,4-Dichloro-phenyl)-pyrrolidin-3-yl]-4-methoxy-N-methyl-3-trifluoromethyl-benzamide (VIII-1),
Carboxylic acid: 1,5-Dimethyl-1H-pyrazole-3-carboxylic acid (commercially available), ES-MS m/e: 568.7 (M+H⁺).

EXAMPLE 59 rac-4-Chloro-pyridine-2-carboxylic acid [(3S,4R)-1-(4-cyano-benzoyl)-4-(3,4-dichloro-phenyl)-pyrrolidin-3-yl]-methyl-amide

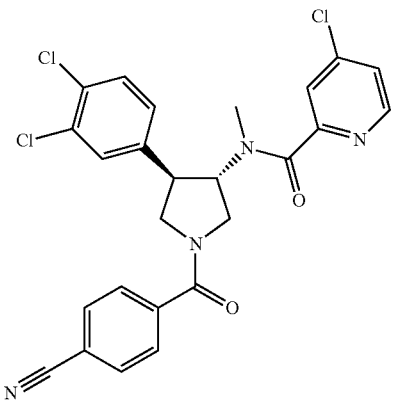 [SMILES: CN(C(=O)c1cc(Cl)ccn1)[C@@H]1CN(C(=O)c2ccc(C#N)cc2)C[C@H]1c1ccc(Cl)c(Cl)c1]

Coupling according to general procedure II:
Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 4-Chloro-pyridine-2-carboxylic acid (commercially available), ES-MS m/e: 515.0 (M+H⁺).

EXAMPLE 60 rac-3-Methyl-pyridine-2-carboxylic acid [(3S,4R)-1-(4-cyano-benzoyl)-4-(3,4-dichloro-phenyl)-pyrrolidin-3-yl]-methyl-amide

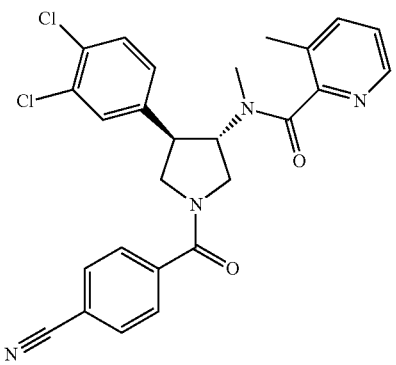 [SMILES: Cc1cccnc1C(=O)N(C)[C@@H]1CN(C(=O)c2ccc(C#N)cc2)C[C@H]1c1ccc(Cl)c(Cl)c1]

Coupling according to general procedure II:
Pyrrolidine intermediate: rac-4-[(3R,4S)-3-(3,4-Dichloro-phenyl)-4-methylamino-pyrrolidine-1-carbonyl]-benzonitrile (XI-5),
Carboxylic acid: 3-Methyl-pyridine-2-carboxylic acid (commercially available), ES-MS m/e: 495.2 (M+H⁺).

EXAMPLE 61 rac-6-Chloro-3-fluoro-pyridine-2-carboxylic acid [(3S,4R)-1-(4-cyano-benzoyl)-4-(3,4-dichloro-phenyl)-pyrrolidin-3-yl]-methyl-amide

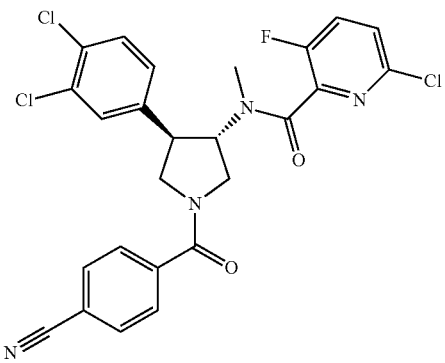 [SMILES: CN(C(=O)c1nc(Cl)ccc1F)[C@@H]1CN(C(=O)c2ccc(C#N)cc2)C[C@H]1c1ccc(Cl)c(Cl)c1]

Coupling according to general procedure II:
Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 6-Chloro-3-fluoro-pyridine-2-carboxylic acid (commercially available), ES-MS m/e: 533.0 (M+H⁺).

EXAMPLE 62 rac-6-Methyl-pyridine-2-carboxylic acid[(3S,4R)-1-(4-cyano-benzoyl)-4-(3,4-dichloro-phenyl)-pyrrolidin-3-yl]-methyl-amide

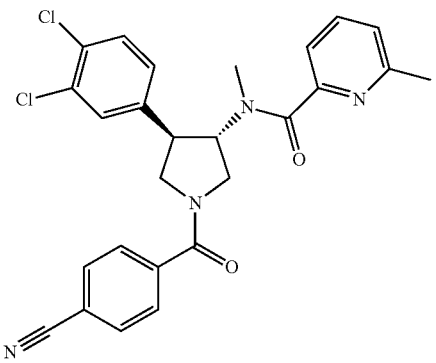 [SMILES: Cc1cccc(C(=O)N(C)[C@@H]2CN(C(=O)c3ccc(C#N)cc3)C[C@H]2c2ccc(Cl)c(Cl)c2)n1]

Coupling according to general procedure II:

Pyrrolidine intermediate: rac-4-[(3R,4S)-3-(3,4-Dichlorophenyl)-4-methylamino-pyrrolidine-1-carbonyl]-benzonitrile (XI-5), Carboxylic acid: 6-Methyl-pyridine-2-carboxylic acid (commercially available), ES-MS m/e: 493.3 (M+H⁺).

EXAMPLE 63 rac-4-Methyl-pyridine-2-carboxylic acid [(3S,4R)-1-(4-cyano-benzoyl)-4-(3,4-dichloro-phenyl)-pyrrolidin-3-yl]-methyl-amide

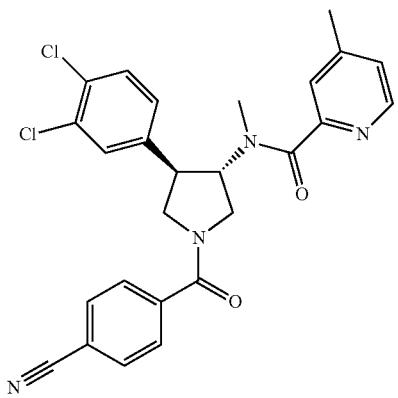 [SMILES: Cc1ccnc(C(=O)N(C)[C@@H]2CN(C(=O)c3ccc(C#N)cc3)C[C@H]2c2ccc(Cl)c(Cl)c2)c1]

Coupling according to general procedure II:

Pyrrolidine intermediate: rac-4-[(3R,4S)-3-(3,4-Dichlorophenyl)-4-methylamino-pyrrolidine-1-carbonyl]-benzonitrile (XI-5), Carboxylic acid: 4-Methyl-pyridine-2-carboxylic acid (commercially available), ES-MS m/e: 493.1 (M+H⁺).

EXAMPLE 64 rac-6-Methoxy-pyridine-2-carboxylic acid [(3S,4R)-1-(4-cyano-benzoyl)-4-(3,4-dichloro-phenyl)-pyrrolidin-3-yl]-methyl-amide

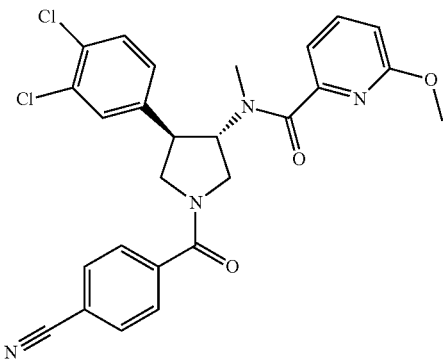 [SMILES: COc1cccc(C(=O)N(C)[C@@H]2CN(C(=O)c3ccc(C#N)cc3)C[C@H]2c2ccc(Cl)c(Cl)c2)n1]

Coupling according to general procedure II:

Pyrrolidine intermediate: rac-4-[(3R,4S)-3-(3,4-Dichlorophenyl)-4-methylamino-pyrrolidine-1-carbonyl]-benzonitrile (XI-5), Carboxylic acid: 6-Methoxy-pyridine-2-carboxylic acid (commercially available), ES-MS m/e: 509.2 (M+H⁺).

EXAMPLE 65 rac-5-Ethoxymethyl-pyridine-2-carboxylic acid [(3S,4R)-1-(4-cyano-benzoyl)-4-(3,4-dichloro-phenyl)-pyrrolidin-3-yl]-methyl-amide

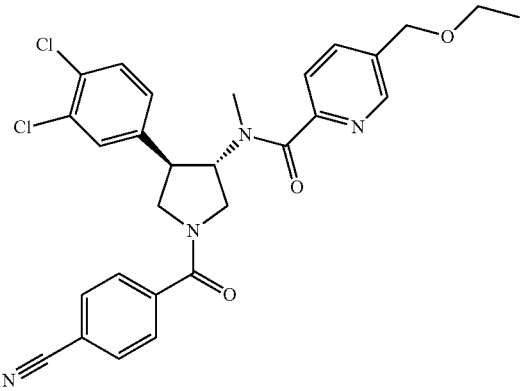 [SMILES: CCOCc1ccc(C(=O)N(C)[C@@H]2CN(C(=O)c3ccc(C#N)cc3)C[C@H]2c2ccc(Cl)c(Cl)c2)nc1]

Coupling according to general procedure II:

Pyrrolidine intermediate: rac-4-[(3R,4S)-3-(3,4-Dichlorophenyl)-4-methylamino-pyrrolidine-1-carbonyl]-benzonitrile (XI-5), Carboxylic acid: 5-Ethoxymethyl-pyridine-2-carboxylic acid (commercially available), ES-MS m/e: 539.3 (M+H⁺).

EXAMPLE 66 rac-4-Chloro-6-methyl-pyridine-2-carboxylic acid [(3S,4R)-1-(4-cyano-benzoyl)-4-(3,4-dichloro-phenyl)-pyrrolidin-3-yl]-methyl-amide

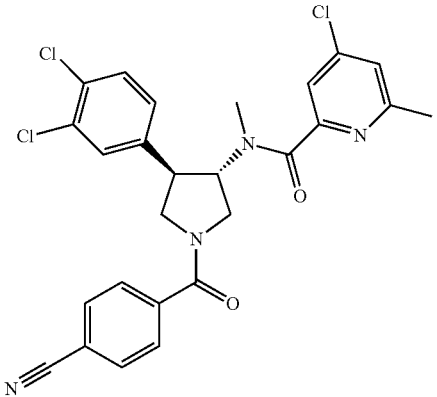 [SMILES: Cc1cc(Cl)cc(C(=O)N(C)[C@@H]2CN(C(=O)c3ccc(C#N)cc3)C[C@H]2c2ccc(Cl)c(Cl)c2)n1]

Coupling according to general procedure II:
Pyrrolidine intermediate: rac-4-[(3R,4S)-3-(3,4-Dichlorophenyl)-4-methylamino-pyrrolidine-1-carbonyl]-benzonitrile (XI-5),
Carboxylic acid: 4-Chloro-6-methyl-pyridine-2-carboxylic acid (commercially available), ES-MS m/e: 529.2 (M+H⁺).

EXAMPLE 67 rac-4-Methoxy-quinoline-2-carboxylic acid [(3S,4R)-1-(4-cyano-benzoyl)-4-(3,4-dichloro-phenyl)-pyrrolidin-3-yl]-methyl-amide

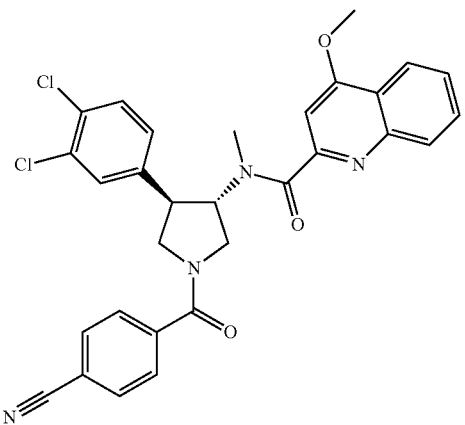 [SMILES: COc1cc(C(=O)N(C)[C@@H]2CN(C(=O)c3ccc(C#N)cc3)C[C@H]2c2ccc(Cl)c(Cl)c2)nc2ccccc12]

Coupling according to general procedure II:
Pyrrolidine intermediate: rac-4-[(3R,4S)-3-(3,4-Dichlorophenyl)-4-methylamino-pyrrolidine-1-carbonyl]-benzonitrile (XI-5),
Carboxylic acid: 4-Methoxy-quinoline-2-carboxylic acid (commercially available), ES-MS m/e: 559.2 (M+H⁺).

EXAMPLE 68 rac-4-Chloro-6-ethyl-pyridine-2-carboxylic acid [(3S,4R)-1-(4-cyano-benzoyl)-4-(3,4-dichloro-phenyl)-pyrrolidin-3-yl]-methyl-amide

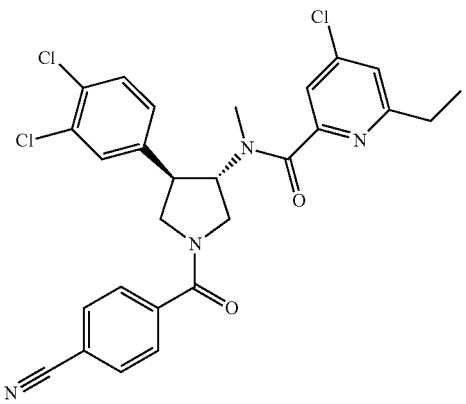 [SMILES: CCc1cc(Cl)cc(C(=O)N(C)[C@@H]2CN(C(=O)c3ccc(C#N)cc3)C[C@H]2c2ccc(Cl)c(Cl)c2)n1]

Coupling according to general procedure II:
Pyrrolidine intermediate: rac-4-[(3R,4S)-3-(3,4-Dichlorophenyl)-4-methylamino-pyrrolidine-1-carbonyl]-benzonitrile (XI-5),
Carboxylic acid: 4-Chloro-6-ethyl-pyridine-2-carboxylic acid, ES-MS m/e: 543.1 (M+H⁺).

EXAMPLE 69 rac-5-Chloro-pyridine-2-carboxylic acid [(3S,4R)-1-(4-cyano-benzoyl)-4-(3,4-dichloro-phenyl)-pyrrolidin-3-yl]-methyl-amide

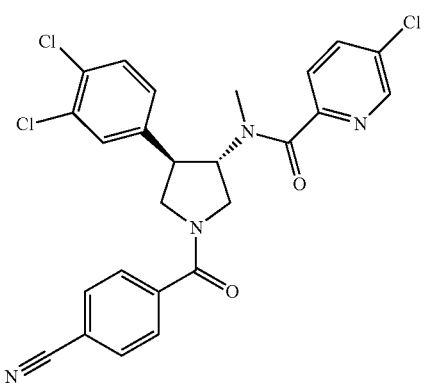 [SMILES: CN(C(=O)c1ccc(Cl)cn1)[C@@H]1CN(C(=O)c2ccc(C#N)cc2)C[C@H]1c1ccc(Cl)c(Cl)c1]

Coupling according to general procedure II:
Pyrrolidine intermediate: rac-4-[(3R,4S)-3-(3,4-Dichlorophenyl)-4-methylamino-pyrrolidine-1-carbonyl]-benzonitrile (XI-5), Carboxylic acid: 5-Chloro-pyridine-2-carboxylic acid (commercially available), ES-MS m/e: 515.0 (M+H⁺).

EXAMPLE 70 rac-5-Cyano-pyridine-2-carboxylic acid [(3S,4R)-1-(4-cyano-benzoyl)-4-(3,4-dichloro-phenyl)-pyrrolidin-3-yl]-methyl-amide

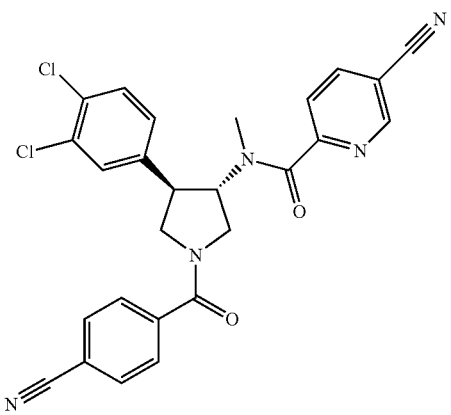 [SMILES: CN(C(=O)c1ccc(C#N)cn1)[C@@H]1CN(C(=O)c2ccc(C#N)cc2)C[C@H]1c1ccc(Cl)c(Cl)c1]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 5-Cyano-pyridine-2-carboxylic acid (commercially available), ES-MS m/e: 504.1 (M+H⁺).

EXAMPLE 71 rac-5-Cyano-6-methoxy-pyridine-2-carboxylic acid [(3S,4R)-1-(4-cyano-benzoyl)-4-(3,4-dichloro-phenyl)-pyrrolidin-3-yl]-methyl-amide

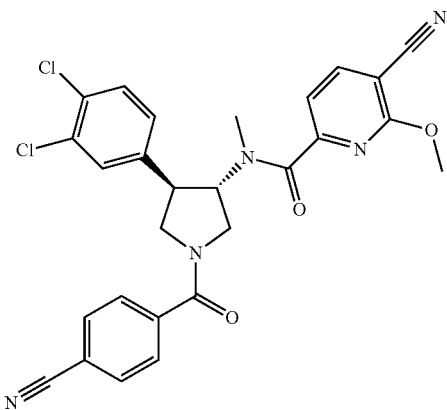 [SMILES: COc1nc(C(=O)N(C)[C@@H]2CN(C(=O)c3ccc(C#N)cc3)C[C@H]2c2ccc(Cl)c(Cl)c2)ccc1C#N]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 5-Cyano-6-methoxy-pyridine-2-carboxylic acid (described in the patent DE3446713), ES-MS m/e: 534.1 (M+H⁺).

EXAMPLE 72 rac-4-Chloro-N-[(3S,4R)-1-(4-cyano-benzoyl)-4-(3,4-dichloro-phenyl)-pyrrolidin-3-yl]-N-methyl-3-trifluoromethyl-benzamide

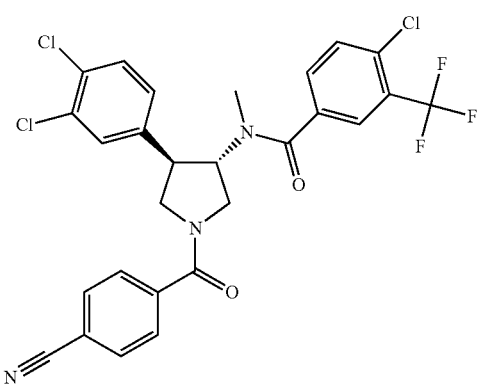 [SMILES: CN(C(=O)c1ccc(Cl)c(C(F)(F)F)c1)[C@@H]1CN(C(=O)c2ccc(C#N)cc2)C[C@H]1c1ccc(Cl)c(Cl)c1]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 4-Chloro-3-trifluoromethyl-benzoic acid (commercially available), ES-MS m/e: 582.3 (M+H⁺).

EXAMPLE 73 rac-N-[(3S,4R)-1-(4-Cyano-benzoyl)-4-(3,4-dichloro-phenyl)-pyrrolidin-3-yl]-3-fluoro-4-methoxy-N-methyl-benzamide

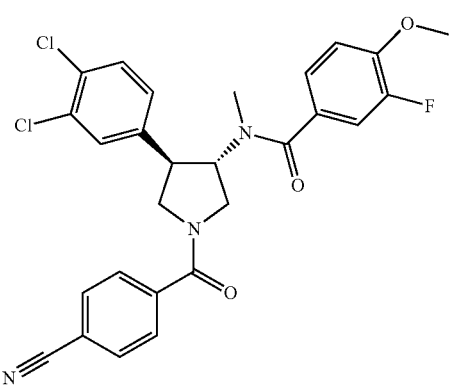 [SMILES: COc1ccc(C(=O)N(C)[C@@H]2CN(C(=O)c3ccc(C#N)cc3)C[C@H]2c2ccc(Cl)c(Cl)c2)cc1F]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 3-Fluoro-4-methoxy-benzoic acid (commercially available), ES-MS m/e: 526.1 (M+H⁺).

EXAMPLE 74 rac-3-tert-Butyl-N-[(3S,4R)-1-(4-cyano-benzoyl)-4-(3,4-dichloro-phenyl)-pyrrolidin-3-yl]-4-methoxy-N-methyl-benzamide

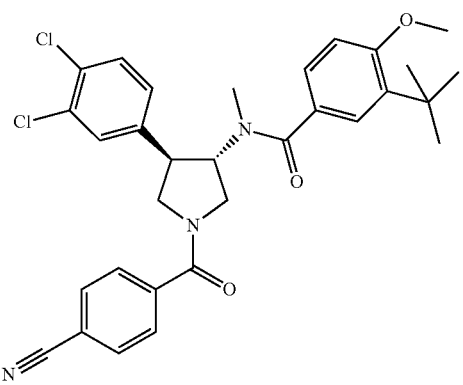 [SMILES: COc1ccc(C(=O)N(C)[C@@H]2CN(C(=O)c3ccc(C#N)cc3)C[C@H]2c2ccc(Cl)c(Cl)c2)cc1C(C)(C)C]

Coupling according to general procedure II:
Pyrrolidine intermediate: rac-4-[(3R,4S)-3-(3,4-Dichloro-phenyl)-4-methylamino-pyrrolidine-1-carbonyl]-benzonitrile (XI-5),
Carboxylic acid: 3-tert-Butyl-4-methoxy-benzoic acid (described in *J. Med. Chem.*, 1995, 38(26), 4993), ES-MS m/e: 564.2 (M+H⁺).

EXAMPLE 75 rac-N-[(3S,4R)-1-(4-Cyano-benzoyl)-4-(3,4-dichloro-phenyl)-pyrrolidin-3-yl]-4-cyclopropyl-methoxy-N-methyl-benzamide

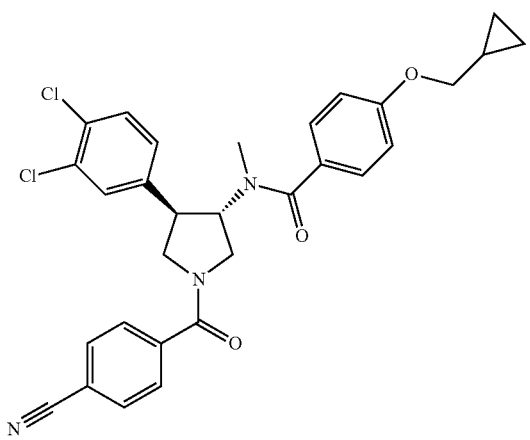 [SMILES: CN(C(=O)c1ccc(OCC2CC2)cc1)[C@@H]1CN(C(=O)c2ccc(C#N)cc2)C[C@H]1c1ccc(Cl)c(Cl)c1]

Coupling according to general procedure II:
Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 4-Cyclopropylmethoxy-benzoic acid (described in patent WO2001060813), ES-MS m/e: 548.2 (M+H⁺).

EXAMPLE 76 rac-2-Methoxy-pyrimidine-5-carboxylic acid [(3S,4R)-1-(4-cyano-benzoyl)-4-(3,4-dichloro-phenyl)-pyrrolidin-3-yl]-methyl-amide

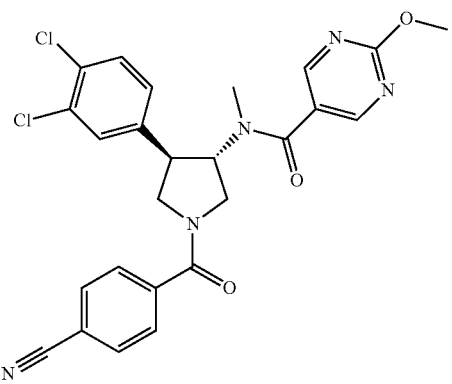 [SMILES: COc1ncc(C(=O)N(C)[C@@H]2CN(C(=O)c3ccc(C#N)cc3)C[C@H]2c2ccc(Cl)c(Cl)c2)cn1]

Coupling according to general procedure II:
Pyrrolidine intermediate: rac-4-[(3R,4S)-3-(3,4-Dichloro-phenyl)-4-methylamino-pyrrolidine-1-carbonyl]-benzonitrile (XI-5),
Carboxylic acid: 2-Methoxy-pyrimidine-5-carboxylic acid (commercially available), ES-MS m/e: 510.1 (M+H⁺).

EXAMPLE 77 rac-N-[(3S,4R)-1-(4-Cyano-benzoyl)-4-(3,4-dichloro-phenyl)-pyrrolidin-3-yl]-6,N-dimethyl-nicotinamide

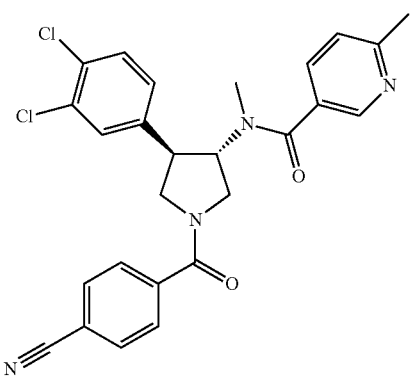 [SMILES: Cc1ccc(C(=O)N(C)[C@@H]2CN(C(=O)c3ccc(C#N)cc3)C[C@H]2c2ccc(Cl)c(Cl)c2)cn1]

Coupling according to general procedure II:
Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 6-Methyl-nicotinic acid (commercially available), ES-MS m/e: 495.3 (M+H⁺).

EXAMPLE 78 rac-6-Chloro-N-[(3S,4R)-1-(4-cyano-benzoyl)-4-(3,4-dichloro-phenyl)-pyrrolidin-3-yl]-N-methyl-nicotinamide

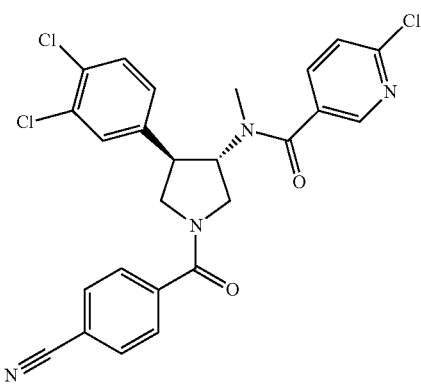 [SMILES: CN(C(=O)c1ccc(Cl)nc1)[C@@H]1CN(C(=O)c2ccc(C#N)cc2)C[C@H]1c1ccc(Cl)c(Cl)c1]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 6-Chloro-nicotinic acid (commercially available), ES-MS m/e: 514.9 (M+H⁺).

EXAMPLE 79 rac-N-[(3S,4R)-1-(4-Cyano-benzoyl)-4-(3,4-dichloro-phenyl)-pyrrolidin-3-yl]-2-fluoro-N-methyl-nicotinamide

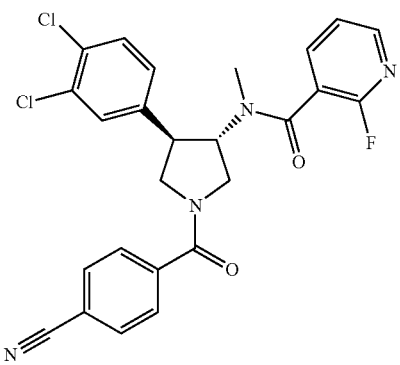 [SMILES: CN(C(=O)c1cccnc1F)[C@@H]1CN(C(=O)c2ccc(C#N)cc2)C[C@H]1c1ccc(Cl)c(Cl)c1]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 2-Fluoro-nicotinic acid (commercially available), ES-MS m/e: 498.9 (M+H⁺).

EXAMPLE 80 rac-6-Cyano-N-[(3S,4R)-1-(4-cyano-benzoyl)-4-(3,4-dichloro-phenyl)-pyrrolidin-3-yl]-N-methyl-nicotinamide

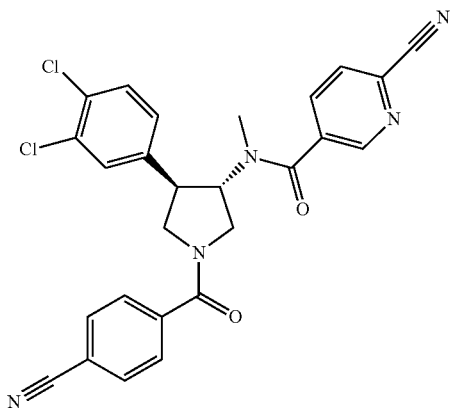 [SMILES: CN(C(=O)c1ccc(C#N)nc1)[C@@H]1CN(C(=O)c2ccc(C#N)cc2)C[C@H]1c1ccc(Cl)c(Cl)c1]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 6-Cyano-nicotinic acid (commercially available), ES-MS m/e: 504.2 (M+H⁺).

EXAMPLE 81 rac-N-[(3S,4R)-1-(4-Cyano-benzoyl)-4-(3,4-dichloro-phenyl)-pyrrolidin-3-yl]-N-methyl-6-trifluoromethyl-nicotinamide

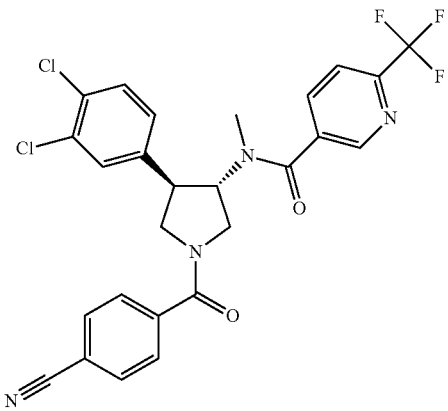 [SMILES: CN(C(=O)c1ccc(C(F)(F)F)nc1)[C@@H]1CN(C(=O)c2ccc(C#N)cc2)C[C@H]1c1ccc(Cl)c(Cl)c1]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 6-Trifluoromethyl-nicotinic acid (commercially available), ES-MS m/e: 547.2 (M+H+).

EXAMPLE 82 rac-N-[(3S,4R)-1-(4-Cyano-benzoyl)-4-(3,4-dichloro-phenyl)-pyrrolidin-3-yl]-N-methyl-6-(2,2,2-trifluoro-ethoxy)-nicotinamide

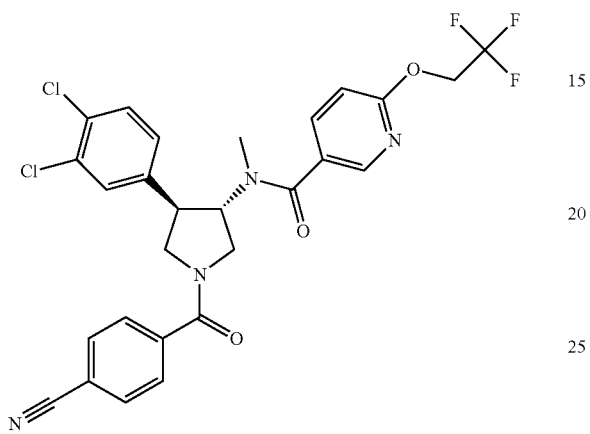

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 6-(2,2,2-Trifluoro-ethoxy)-nicotinic acid (commercially available), ES-MS m/e: 579.2 (M+H+).

EXAMPLE 83 rac-N-[(3S,4R)-1-(4-Cyano-benzoyl)-4-(3,4-dichloro-phenyl)-pyrrolidin-3-yl]-5,N-dimethyl-nicotinamide

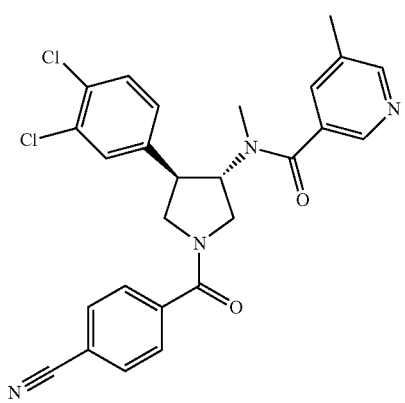 [SMILES: Cc1cncc(C(=O)N(C)[C@@H]2CN(C(=O)c3ccc(C#N)cc3)C[C@H]2c2ccc(Cl)c(Cl)c2)c1]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 5-Methyl-nicotinic acid (commercially available), ES-MS m/e: 493.2 (M+H+).

EXAMPLE 84 rac-N-[(3S,4R)-1-(4-Cyano-benzoyl)-4-(3,4-dichloro-phenyl)-pyrrolidin-3-yl]-5-fluoro-N-methyl-nicotinamide

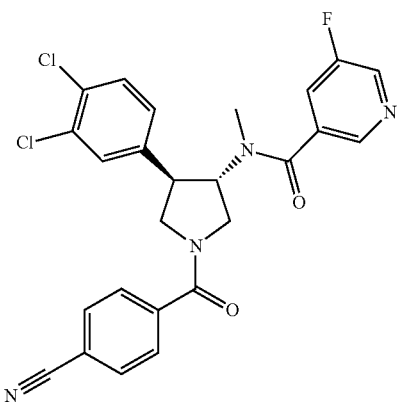 [SMILES: CN(C(=O)c1cncc(F)c1)[C@@H]1CN(C(=O)c2ccc(C#N)cc2)C[C@H]1c1ccc(Cl)c(Cl)c1]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 5-Fluoro-nicotinic acid (commercially available), ES-MS m/e: 497.3 (M+H+).

EXAMPLE 85 rac-N-[(3S,4R)-1-(4-Cyano-benzoyl)-4-(3,4-dichloro-phenyl)-pyrrolidin-3-yl]-6-fluoro-N-methyl-nicotinamide

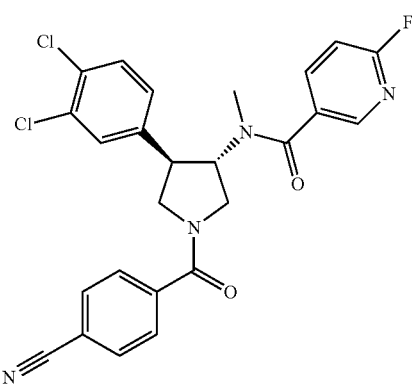 [SMILES: CN(C(=O)c1ccc(F)nc1)[C@@H]1CN(C(=O)c2ccc(C#N)cc2)C[C@H]1c1ccc(Cl)c(Cl)c1]

Coupling according to general procedure II:

Pyrrolidine intermediate: rac-4-[(3R,4S)-3-(3,4-Dichloro-phenyl)-4-methylamino-pyrrolidine-1-carbonyl]-benzonitrile (XI-5), Carboxylic acid: 6-Fluoro-nicotinic acid (commercially available), ES-MS m/e: 499.2 (M+H⁺).

EXAMPLE 86 rac-N-[(3S,4R)-1-(4-Cyano-benzoyl)-4-(3,4-dichloro-phenyl)-pyrrolidin-3-yl]-6-methoxy-N-methyl-nicotinamide

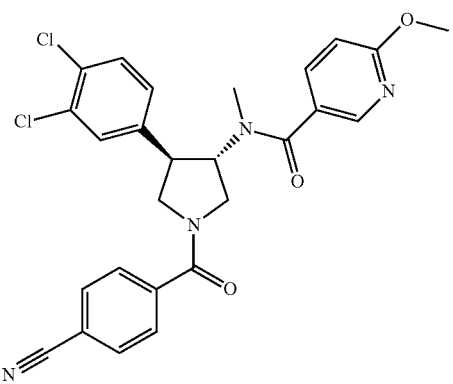 [SMILES: COc1ccc(C(=O)N(C)[C@@H]2CN(C(=O)c3ccc(C#N)cc3)C[C@H]2c2ccc(Cl)c(Cl)c2)cn1]

Coupling according to general procedure II:
Pyrrolidine intermediate: rac-4-[(3R,4S)-3-(3,4-Dichloro-phenyl)-4-methylamino-pyrrolidine-1-carbonyl]-benzonitrile (XI-5),
Carboxylic acid: 6-Methoxy-nicotinic acid (commercially available), ES-MS m/e: 509.0 (M+H⁺).

EXAMPLE 87

N-{(3RS,4SR)-4-(4-Chloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide

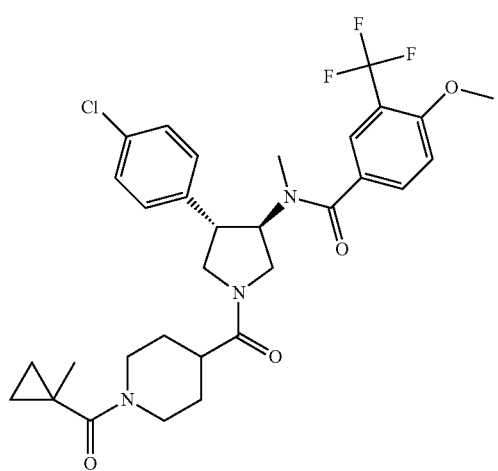 [SMILES: COc1ccc(C(=O)N(C)[C@H]2CN(C(=O)C3CCN(C(=O)C4(C)CC4)CC3)C[C@@H]2c2ccc(Cl)cc2)cc1C(F)(F)F]

a) N-[(3RS,4SR)-1-Benzyl-4-(4-chloro-phenyl)-pyrrolidin-3-yl]-4-methoxy-N-methyl-3-trifluoromethyl-benzamide

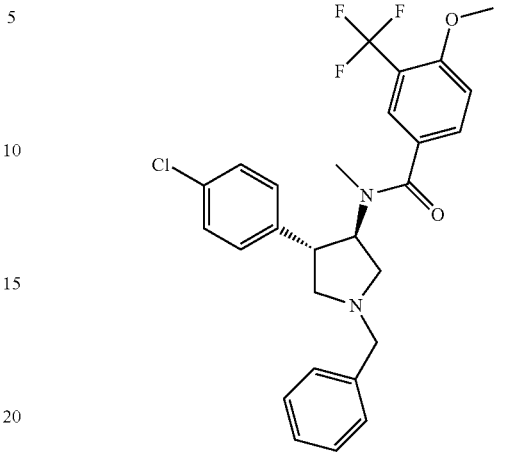

Coupling according to general procedure I:
Pyrrolidine intermediate: [(3RS,4SR)-1-Benzyl-4-(4-chloro-phenyl)-pyrrolidin-3-yl]-methyl-amine (XI-2c),
Acide chloride: 4-Methoxy-3-(trifluoromethyl)benzoyl chloride ES-MS m/e: 503.2 (M+H⁺).

b) N-[(3RS,4SR)-4-(4-Chloro-phenyl)-pyrrolidin-3-yl]-4-methoxy-N-methyl-3-trifluoromethyl-benzamide

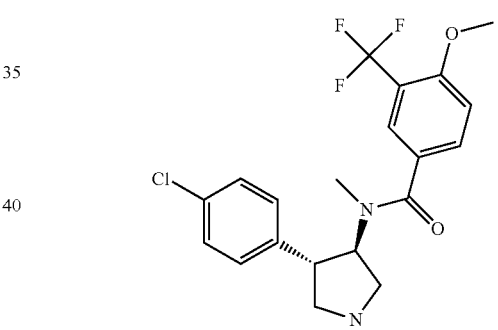

To a solution of N-[(3RS,4SR)-1-benzyl-4-(4-chloro-phenyl)-pyrrolidin-3-yl]-4-methoxy-N-methyl-3-trifluoromethyl-benzamide (7.44 g, 14.8 mmol) and N,N-diisopropyl ethyl amine (3.29 ml, 19 mmol) in toluene (106 mL) was added at ambient temperature over a period of 5 min 1-chloroethyl chloroformate (2.10 mL, 19.2 mmol) and the reaction mixture stirred for 3 h at this temperature. The light brown solution was concentrated in vacuo at 45° C. and the residue was dissolved in methanol (106 mL) and stirred for 3 h at ambient temperature. The solution was concentrated in vacuo. The residue was diluted with an aqueous solution of hydrochloric acid (1M, 30 mL) and water (100 mL). The aqueous layer was washed twice with TBME (50 ml). The organic. layers were extracted with water (50 mL). The combined aqueous biphasic layers were diluted with TBME (50 mL) and basified by addition of a 32% solution of sodium hydroxide (4 mL). The aqueous layer was extracted with TBME (50 mL) and washed with brine (30 mL). The combined organic layers were dried over sodium sulfate. Purification by chromatography (SiO$_2$, dichloromethane:methanol:ammonia=95:4.5:0.5 to 90:9:1) afforded the title compound (2.56 mg, 42%) as a brown oil. MS m/e: 413.2 [M]$^+$.

c) N-{(3RS,4SR)-4-(4-Chloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide To a solution of N-[(3RS,4SR)-4-(4-chloro-phenyl)-pyrrolidin-3-yl]-4-methoxy-N-methyl-3-trifluoromethyl-benzamide (200 mg, 0.484 mmol) in DMF (2 mL) was added 1-(1-methyl-cyclopropanecarbonyl)-piperidine-4-carboxylic acid (113 mg, 0.533 mmol), O-(7-azabenzotriazol-1-yl)-N,N,N',N'-tetramethyluronium hexafluorophosphate (221 mg, 0.581 mmol) and N,N-diisopropyl ethyl amine (498 µl, 2.90 mmol). The solution was stirred for 3 h at ambient temperature. After diluting with ethyl acetate (15 mL) the solution was washed twice with water (15 mL) and brine (10 mL). The aqueous layers were extracted with ethyl acetate (15 mL) and dried over sodium sulfate. Purification by chromatography (SiO$_2$, heptane:ethyl acetate:methanol=50:50:0 to 0:90:10) afforded the title compound (210 mg, 72%) as a light brown oil. MS m/e: 606.2 [M]$^+$.

EXAMPLE 88

N-[(3RS,4SR)-4-(4-Chloro-phenyl)-1-(4-fluoro-benzoyl)-pyrrolidin-3-yl]-4-methoxy-N-methyl-3-trifluoromethyl-benzamide

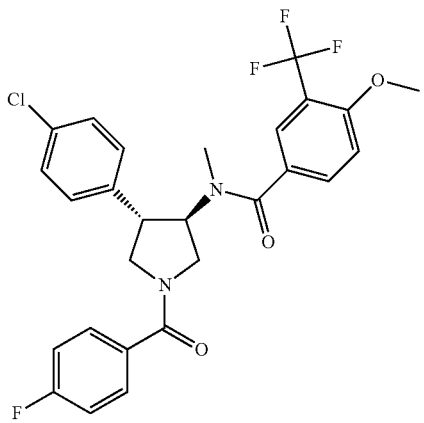 [SMILES: COc1ccc(C(=O)N(C)[C@H]2CN(C(=O)c3ccc(F)cc3)C[C@@H]2c2ccc(Cl)cc2)cc1C(F)(F)F]

To a solution of N-[(3RS,4SR)-4-(4-chloro-phenyl)-pyrrolidin-3-yl]-4-methoxy-N-methyl-3-trifluoromethyl-benzamide (200 mg, 0.484 mmol) in dichloromethane (2 mL) was added 4-fluorobenzoyl chloride (63 µl, 0.533 mmol) and N,N-diisopropyl ethyl amine (124 µl, 0.727 mmol). The solution was stirred for 3 h at ambient temperature. After diluting with ethyl acetate (15 mL) the solution was washed twice with water (15 mL) and brine (10 mL). The aqueous layers were extracted with ethyl acetate (15 mL) and dried over sodium sulfate. Purification by chromatography (SiO$_2$, heptane:ethyl acetate=50:50 to 0:100) afforded the title compound (245 mg, 95%) as a light brown oil. MS m/e: 535.2 [M+H]$^+$.

EXAMPLE 89

N-[(3RS,4SR)-4-(4-Chloro-phenyl)-1-(4-fluoro-2-methyl-benzoyl)-pyrrolidin-3-yl]-4-methoxy-N-methyl-3-trifluoromethyl-benzamide

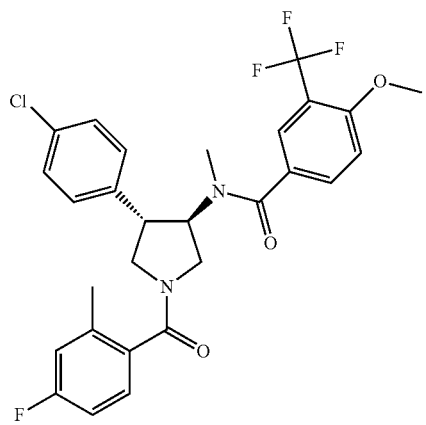 [SMILES: COc1ccc(C(=O)N(C)[C@H]2CN(C(=O)c3ccc(F)cc3C)C[C@@H]2c2ccc(Cl)cc2)cc1C(F)(F)F]

In analogy to the procedure described for the synthesis of example 87 (step c), the title compound N-[(3RS,4SR)-4-(4-chloro-phenyl)-1-(4-fluoro-2-methyl-benzoyl)-pyrrolidin-3-yl]-4-methoxy-N-methyl-3-trifluoromethyl-benzamide was prepared from N-[(3RS,4SR)-4-(4-chloro-phenyl)-pyrrolidin-3-yl]-4-methoxy-N-methyl-3-trifluoromethyl-benzamide using 4-fluoro-2-methylbenzoic acid instead of 1-(1-methyl-cyclopropanecarbonyl)-piperidine-4-carboxylic acid and was obtained as a light brown oil. MS m/e: 549.2 [M+H]$^+$.

EXAMPLE 90

N-[(3RS,4SR)-4-(4-Chloro-phenyl)-1-(6-cyano-pyridine-3-carbonyl)-pyrrolidin-3-yl]-4-methoxy-N-methyl-3-trifluoromethyl-benzamide

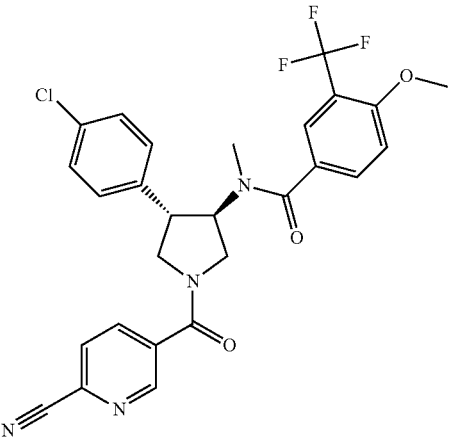 [SMILES: COc1ccc(C(=O)N(C)[C@H]2CN(C(=O)c3ccc(C#N)nc3)C[C@@H]2c2ccc(Cl)cc2)cc1C(F)(F)F]

In analogy to the procedure described for the synthesis of example 87 (step c), the title compound N-[(3RS,4SR)-4-(4-chloro-phenyl)-1-(6-cyano-pyridine-3-carbonyl)-pyrrolidin-3-yl]-4-methoxy-N-methyl-3-trifluoromethyl-benzamide was prepared from N-[(3RS,4SR)-4-(4-chloro-phenyl)-pyrrolidin-3-yl]-4-methoxy-N-methyl-3-trifluoromethyl-benzamide using 6-cyanonicotinic acid instead of 1-(1-methylcyclopropanecarbonyl)-piperidine-4-carboxylic acid and was obtained as a light brown oil. MS m/e: 543.1 [M+H]+.

EXAMPLE 91

N-[(3RS,4SR)-4-(4-Chloro-phenyl)-1-(4-isopropoxy-benzoyl)-pyrrolidin-3-yl]-4-methoxy-N-methyl-3-trifluoromethyl-benzamide

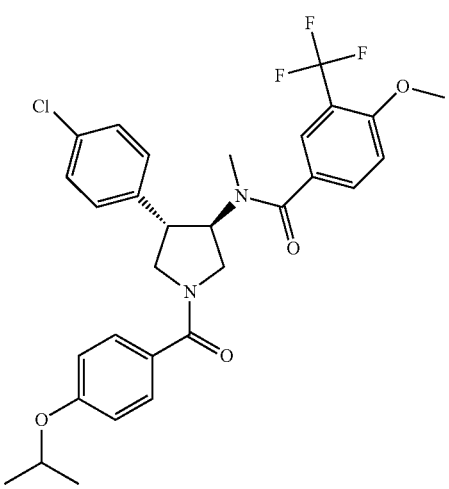 [SMILES: COc1ccc(C(=O)N(C)[C@H]2CN(C(=O)c3ccc(OC(C)C)cc3)C[C@@H]2c2ccc(Cl)cc2)cc1C(F)(F)F]

In analogy to the procedure described for the synthesis of example 87 (step c), the title compound N-[(3RS,4SR)-4-(4-chloro-phenyl)-1-(4-isopropoxy-benzoyl)-pyrrolidin-3-yl]-4-methoxy-N-methyl-3-trifluoromethyl-benzamide was prepared from N-[(3RS,4SR)-4-(4-chloro-phenyl)-pyrrolidin-3-yl]-4-methoxy-N-methyl-3-trifluoromethyl-benzamide using 4-isopropoxybenzoic acid instead of 1-(1-methyl-cyclopropanecarbonyl)-piperidine-4-carboxylic acid and was obtained as a light brown oil. MS m/e: 575.2 [M+H]+.

EXAMPLE 92

N-[(3RS,4SR)-4-(4-Chloro-phenyl)-1-(4-cyano-benzoyl)-pyrrolidin-3-yl]-4-methoxy-N-methyl-3-trifluoromethyl-benzamide

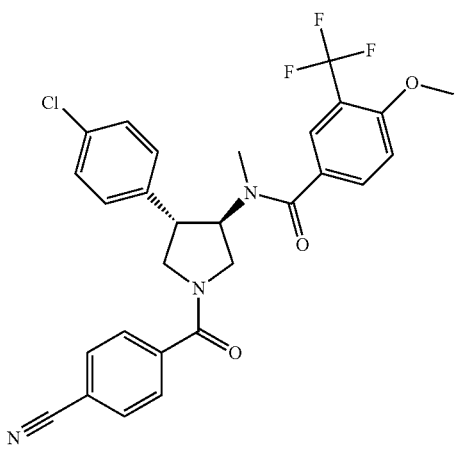 [SMILES: COc1ccc(C(=O)N(C)[C@H]2CN(C(=O)c3ccc(C#N)cc3)C[C@@H]2c2ccc(Cl)cc2)cc1C(F)(F)F]

In analogy to the procedure described for the synthesis of example 88, the title compound N-[(3RS,4SR)-4-(4-chloro-phenyl)-1-(4-cyano-benzoyl)-pyrrolidin-3-yl]-4-methoxy-N-methyl-3-trifluoromethyl-benzamide was prepared from N-[(3RS,4SR)-4-(4-chloro-phenyl)-pyrrolidin-3-yl]-4-methoxy-N-methyl-3-trifluoromethyl-benzamide using 4-cyanobenzoyl chloride instead of 4-fluorobenzoyl chloride and was obtained as a light brown oil. MS m/e: 542.1 [M+H]+.

EXAMPLE 93

N-{(3R,4S)-4-(4-Chloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide

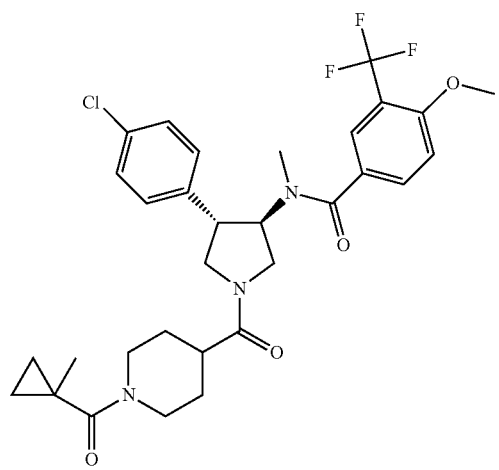 [SMILES: COc1ccc(C(=O)N(C)[C@H]2CN(C(=O)C3CCN(C(=O)C4(C)CC4)CC3)C[C@@H]2c2ccc(Cl)cc2)cc1C(F)(F)F]

and

EXAMPLE 94

N-{(3S,4R)-4-(4-Chloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide

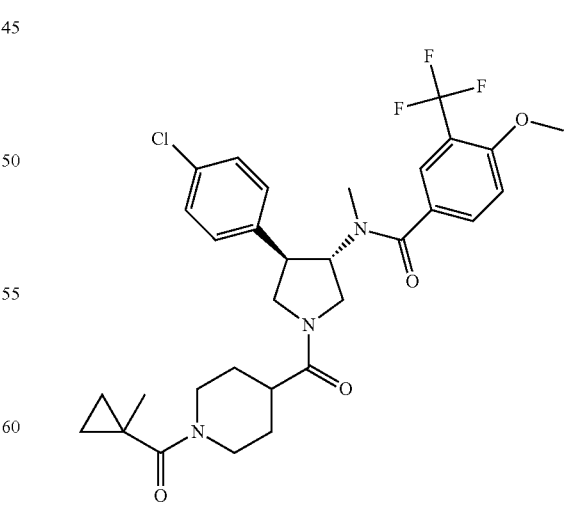

N-{(3RS,4SR)-4-(4-Chloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide was subjected to column chromatography on chiral phase to yield N-{(3R,4S)-4-(4-chloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide (MS (m/e): 606.2 [M]$^+$) as a colorless oil and N-{(3S,4R)-4-(4-chloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide (MS (m/e): 606.2 [M]$^+$) as a colorless oil.

EXAMPLE 95

4-{(3SR,4RS)-3-(4-Chloro-phenyl)-4-[(4-methoxy-3-trifluoromethyl-benzoyl)-methyl-amino]-pyrrolidine-1-carbonyl}-piperidine-1-carboxylic acid tert-butyl ester

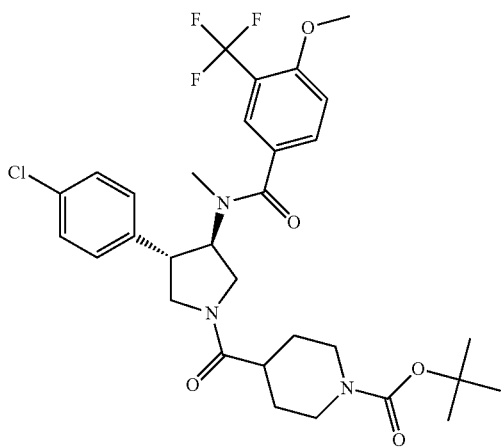 [SMILES: COc1ccc(C(=O)N(C)[C@H]2CN(C(=O)C3CCN(C(=O)OC(C)(C)C)CC3)C[C@@H]2c2ccc(Cl)cc2)cc1C(F)(F)F]

In analogy to the procedure described for the synthesis of example 87 (step c), the title compound 4-{(3SR,4RS)-3-(4-chloro-phenyl)-4-[(4-methoxy-3-trifluoromethyl-benzoyl)-methyl-amino]-pyrrolidine-1-carbonyl}-piperidine-1-carboxylic acid tert-butyl ester was prepared from N-[(3RS,4SR)-4-(4-chloro-phenyl)-pyrrolidin-3-yl]-4-methoxy-N-methyl-3-trifluoromethyl-benzamide using piperidine-1,4-dicarboxylic acid mono-tert-butyl ester instead of 1-(1-methyl-cyclopropanecarbonyl)-piperidine-4-carboxylic acid and was obtained as a light brown foam. MS m/e: 624.3 [M]$^+$.

EXAMPLE 96

N-{(3RS,4SR)-4-(3,4-Dichloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide

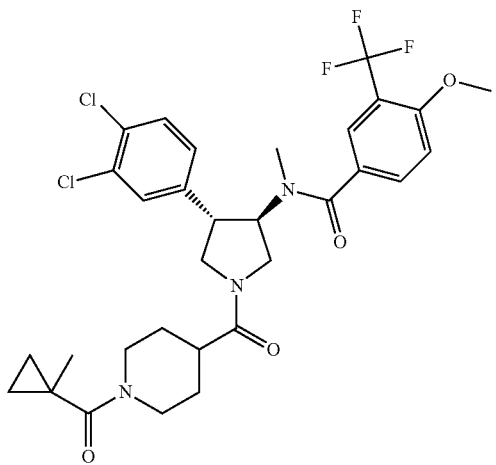 [SMILES: COc1ccc(C(=O)N(C)[C@H]2CN(C(=O)C3CCN(C(=O)C4(C)CC4)CC3)C[C@@H]2c2ccc(Cl)c(Cl)c2)cc1C(F)(F)F]

a) [(3RS,4SR)-1-Benzyl-4-(3,4-dichloro-phenyl)-pyrrolidin-3-yl]-methyl-carbamic acid tert-butyl ester

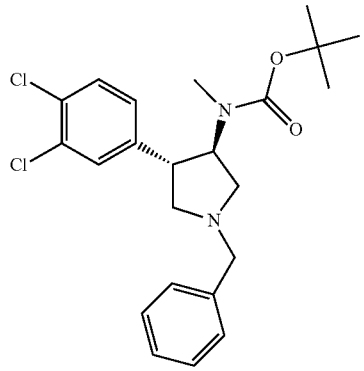 [SMILES: CN(C(=O)OC(C)(C)C)[C@H]1CN(Cc2ccccc2)C[C@@H]1c1ccc(Cl)c(Cl)c1]

To a solution of [(3RS,4SR)-1-benzyl-4-(3,4-dichloro-phenyl)-pyrrolidin-3-yl]-methyl-amine (Pyrrolidine VI-I, 2.85 g, 8.50 mmol) in dichloromethane (29 mL) was added at ambient temperature triethylamine (2.4 mL, 17.0 mmol), 4-dimethylaminopyridine (0.10 g, 0.85 mmol) and di-tert-butyl-dicarbonate (2.04 g, 9.35 mmol). The resulting solution was stirred in a water bath for 2 h at ambient temperature. It was diluted with water (30 mL). The organic layer was washed with water (30 mL). The aqueous layers were extracted twice with dichloromethane (20 mL) and the combined organic layers were dried over sodium sulfate. Purification by chromatography (SiO$_2$, heptane:ethyl acetate=100:0 to 60:40) afforded the title compound (3.52 g, 95%) as a light brown oil. MS m/e: 435.2 [M]$^+$.

b) [(3RS,4SR)-4-(3,4-Dichloro-phenyl)-pyrrolidin-3-yl]-methyl-carbamic acid tert-butyl ester

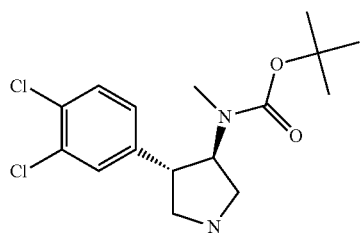 [SMILES: CN(C(=O)OC(C)(C)C)[C@H]1CNC[C@@H]1c1ccc(Cl)c(Cl)c1]

In analogy to the procedure described for the synthesis of example 87 (step b), the title compound [(3RS,4SR)-4-(3,4-dichloro-phenyl)-pyrrolidin-3-yl]-methyl-carbamic acid tert-butyl ester was prepared from [(3RS,4SR)-1-benzyl-4-(3,4-dichloro-phenyl)-pyrrolidin-3-yl]-methyl-carbamic acid tert-butyl ester and was obtained as a light brown oil. MS m/e: 345.1 [M]$^+$.

c) {(3RS,4SR)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester

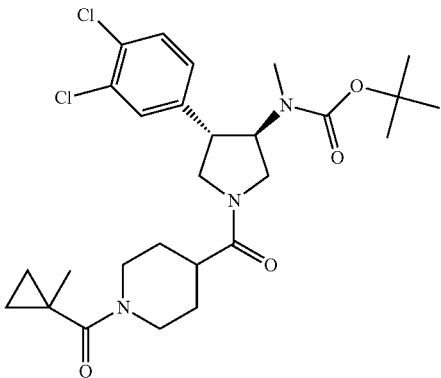 [SMILES: CN(C(=O)OC(C)(C)C)[C@H]1CN(C(=O)C2CCN(C(=O)C3(C)CC3)CC2)C[C@@H]1c1ccc(Cl)c(Cl)c1]

In analogy to the procedure described for the synthesis of example 87 (step c), the title compound {(3RS,4SR)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester was prepared from [(3RS,4SR)-4-(3,4-dichloro-phenyl)-pyrrolidin-3-yl]-methyl-carbamic acid tert-butyl ester and was obtained as a light brown foam. MS m/e: 538.3 [M]+.

d) {4-[(3SR,4RS)-3-(3,4-Dichloro-phenyl)-4-methylamino-pyrrolidine-1-carbonyl]-piperidin-1-yl}-(1-methyl-cyclopropyl)-methanone

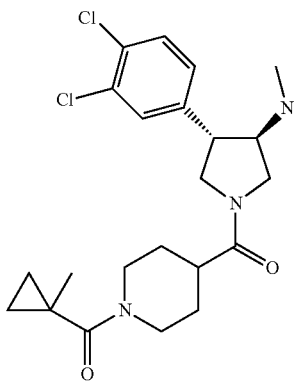 [SMILES: CN[C@H]1CN(C(=O)C2CCN(C(=O)C3(C)CC3)CC2)C[C@@H]1c1ccc(Cl)c(Cl)c1]

Under an atmosphere of nitrogen was added to a solution of {(3RS,4SR)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester (3.02 g, 5.61 mmol) in dichloromethane (30 mL) at ambient temperature trifluoroacetic acid (4.3 mL, 56 mmol) and stirred for 20 h at this temperature. The reaction mixture was added slowly onto an aqueous solution of sodium carbonate (1M, 60 mL). The organic layer was separated and washed with brine (50 mL). The aqueous layers were extracted with dichloromethane (30 mL) and the combined organic layers were dried over sodium sulfate. Purification by chromatography (SiO$_2$, heptane:ethyl acetate:methanol=50:50:0 to 0:90:10) afforded the title compound (1.79 g, 73%) as a light brown oil. MS m/e: 438.3 [M]+.

e) N-{(3RS,4SR)-4-(3,4-Dichloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide To a solution of {4-[(3SR,4RS)-3-(3,4-dichloro-phenyl)-4-methylamino-pyrrolidine-1-carbonyl]-piperidin-1-yl}-(1-methyl-cyclopropyl)-methanone (200 mg, 0.456 mmol) in THF (2 mL) was added N,N-diisopropyl ethyl amine (117 µl, 0.684 mmol), 4-methoxy-3-(trifluoromethyl)benzoyl chloride (131 mg, 0.547 mmol) and stirred for 4 h at ambient temperature. The reaction mixture was diluted with ethzl acetatec (10 mL) and was washed with an aqueous solution of sodium carbonate (1 M, 10 mL), water (10 mL) and brine (10 mL). The aqueous layers were extracted with ethyl acetate (20 mL) and the combined organic layers were dried over sodium sulfate. Purification by chromatography (SiO$_2$, heptane:ethyl acetate:methanol=50:50:0 to 0:90:10) afforded the title compound (230 mg, 79%) as a colorless oil. MS m/e: 640.3 [M]+.

EXAMPLE 97

4-Chloro-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-3-trifluoromethyl-benzamide

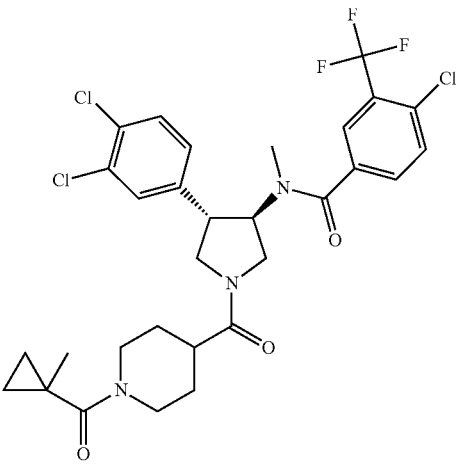 [SMILES: CN(C(=O)c1ccc(Cl)c(C(F)(F)F)c1)[C@H]1CN(C(=O)C2CCN(C(=O)C3(C)CC3)CC2)C[C@@H]1c1ccc(Cl)c(Cl)c1]

To a mixture of 4-chloro-3-(trifluoromethyl)benzoic acid (31 mg, 0.14 mmol) and 1-(3-dimethylaminopropyl)-3-ethylcarbodiimide hydrochloride (27 mg, 0.14 mmol) was added at 0° C. under an atmosphere of nitrogen a solution {4-[(3SR, 4RS)-3-(3,4-dichloro-phenyl)-4-methylamino-pyrrolidine-1-carbonyl]-piperidin-1-yl}-(1-methyl-cyclopropyl)-methanone (50 mg, 0.11 mmol) in dichloromethane (1 mL). The solution was stirred for 3 d in a thawing ice bath. The resulting solution was diluted with dichloromethane and was washed twice with water (10 mL). The aqueous layers were extracted with dichloromethane (10 mL) and the combined organic layers were dried over sodium sulfate. Purification by chromatography (SiO$_2$, heptane:ethyl acetate:methanol=50:50:0 to 0:90:10) afforded the title compound (63 mg, 86%) as a light brown foam. MS m/e: 646.3 [M+H]+.

EXAMPLE 98

N-{(3RS,4SR)-4-(3,4-Dichloro-phenyl)-1-[1-(1-methyl-cyclopropanecarbonyl)-piperidine-4-carbonyl]-pyrrolidin-3-yl}-4-fluoro-N-methyl-3-trifluoromethoxy-benzamide

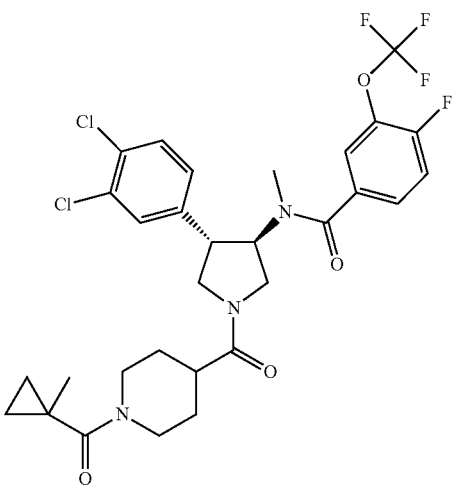 [SMILES: CN(C(=O)c1ccc(F)c(OC(F)(F)F)c1)[C@H]1CN(C(=O)C2CCN(C(=O)C3(C)CC3)CC2)C[C@@H]1c1ccc(Cl)c(Cl)c1]

In analogy to the procedure described for the synthesis of example 97, the title compound N-{(3RS,4SR)-4-(3,4-dichloro-phenyl)-1-[1-(1-methyl-cyclopropanecarbonyl)-piperidine-4-carbonyl]-pyrrolidin-3-yl}-4-fluoro-N-methyl-3-trifluoromethoxy-benzamide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 4-fluoro-3-(trifluoromethyl)benzoic acid instead of 4-chloro-3-(trifluoromethyl)benzoic acid and was obtained as a light brown foam. MS m/e: 644.4 [M]+.

EXAMPLE 99

4-Chloro-N-{(3RS,4SR)-4-(3,4-dichloro-phenyl)-1-[1-(1-methyl-cyclopropanecarbonyl)-piperidine-4-carbonyl]-pyrrolidin-3-yl}-3-methoxy-N-methyl-benzamide

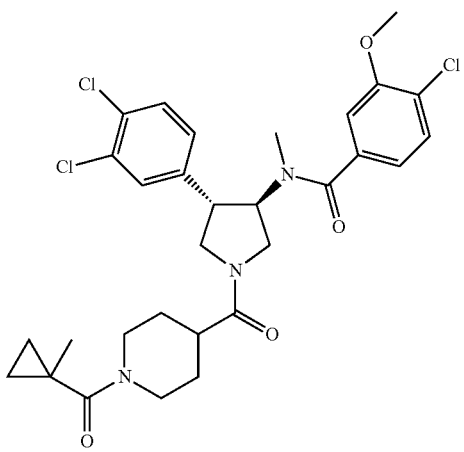 [SMILES: COc1cc(C(=O)N(C)[C@H]2CN(C(=O)C3CCN(C(=O)C4(C)CC4)CC3)C[C@@H]2c2ccc(Cl)c(Cl)c2)ccc1Cl]

In analogy to the procedure described for the synthesis of example 97, the title compound 4-chloro-N-{(3RS,4SR)-4-(3,4-dichloro-phenyl)-1-[1-(1-methyl-cyclopropanecarbonyl)-piperidine-4-carbonyl]-pyrrolidin-3-yl}-3-methoxy-N-methyl-benzamide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 4-chloro-3-methoxybenzoic acid instead of 4-chloro-3-(trifluoromethyl)benzoic acid and was obtained as a light brown foam. MS m/e: 608.1 [M+H]+.

EXAMPLE 100

N-{(3RS,4SR)-4-(3,4-Dichloro-phenyl)-1-[1-(1-methyl-cyclopropanecarbonyl)-piperidine-4-carbonyl]-pyrrolidin-3-yl}-4-fluoro-N-methyl-benzamide

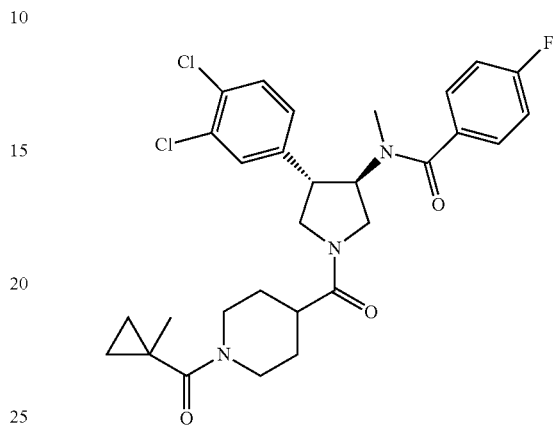

In analogy to the procedure described for the synthesis of example 96 (step e), the title compound N-{(3RS,4SR)-4-(3,4-dichloro-phenyl)-1-[1-(1-methyl-cyclopropanecarbonyl)-piperidine-4-carbonyl]-pyrrolidin-3-yl}-4-fluoro-N-methyl-benzamide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 4-fluorobenzoyl chloride instead of 4-methoxy-3-(trifluoromethyl)benzoyl chloride and was obtained as a light brown foam. MS m/e: 560.1 [M]+.

EXAMPLE 101

N-{(3RS,4SR)-4-(3,4-Dichloro-phenyl)-1-[1-(1-methyl-cyclopropanecarbonyl)-piperidine-4-carbonyl]-pyrrolidin-3-yl}-2-(4-fluoro-phenyl)-N-methyl-acetamide

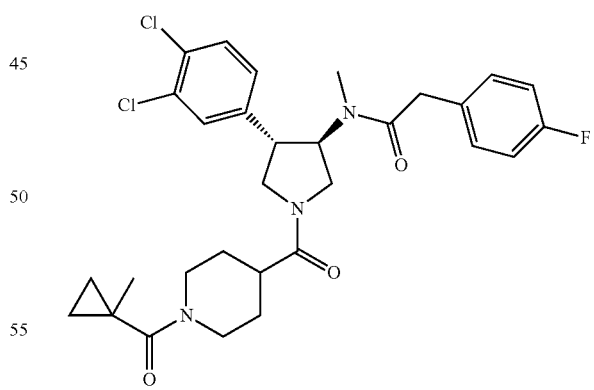

In analogy to the procedure described for the synthesis of example 97, the title compound N-{(3RS,4SR)-4-(3,4-dichloro-phenyl)-1-[1-(1-methyl-cyclopropanecarbonyl)-piperidine-4-carbonyl]-pyrrolidin-3-yl}-2-(4-fluoro-phenyl)-N-methyl-acetamide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 4-fluorophenylacetic acid instead of 4-chloro-3-(trifluoromethyl)benzoic acid and was obtained as a light brown foam. MS m/e: 574.2 [M]+.

EXAMPLE 102

N-{(3RS,4SR)-4-(3,4-Dichloro-phenyl)-1-[1-(1-methyl-cyclopropanecarbonyl)-piperidine-4-carbonyl]-pyrrolidin-3-yl}-3-(4-fluoro-phenyl)-N-methyl-propionamide

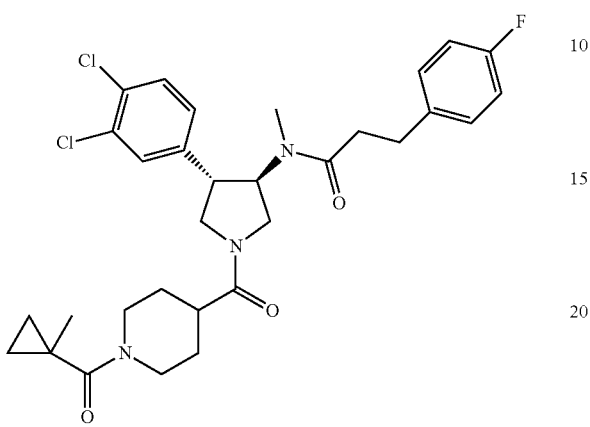

In analogy to the procedure described for the synthesis of example 97, the title compound N-{(3RS,4SR)-4-(3,4-dichloro-phenyl)-1-[1-(1-methyl-cyclopropanecarbonyl)-piperidine-4-carbonyl]-pyrrolidin-3-yl}-3-(4-fluoro-phenyl)-N-methyl-propionamide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 3-(4-fluorophenyl)propionic acid instead of 4-chloro-3-(trifluoromethyl)benzoic acid and was obtained as a light brown foam. MS m/e: 588.2 [M]+.

EXAMPLE 103

N-[(3RS,4SR)-4-(4-Chloro-phenyl)-1-(piperidine-4-carbonyl)-pyrrolidin-3-yl]-4-methoxy-N-methyl-3-trifluoromethyl-benzamide

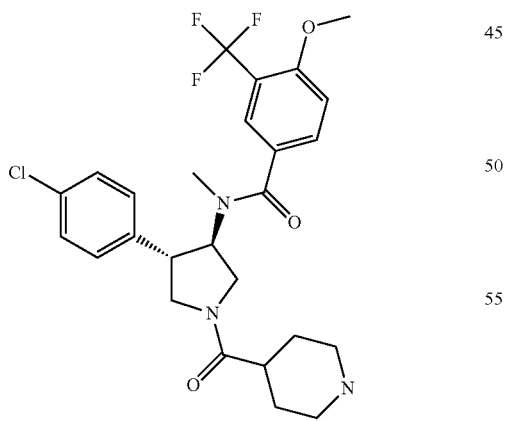

In analogy to the procedure described for the synthesis of example 96 (step d), the title compound N-[(3RS,4SR)-4-(4-chloro-phenyl)-1-(piperidine-4-carbonyl)-pyrrolidin-3-yl]-4-methoxy-N-methyl-3-trifluoromethyl-benzamide was prepared from 4-{(3SR,4RS)-3-(4-chloro-phenyl)-4-[(4-methoxy-3-trifluoromethyl-benzoyl)-methyl-amino]-pyrrolidine-1-carbonyl}-piperidine-1-carboxylic acid tert-butyl ester and was obtained as a white foam. MS m/e: 524.3 [M+H]+.

EXAMPLE 104

N-[(3RS,4SR)-4-(4-Chloro-phenyl)-1-(1-isopropyl-piperidine-4-carbonyl)-pyrrolidin-3-yl]-4-methoxy-N-methyl-3-trifluoromethyl-benzamide

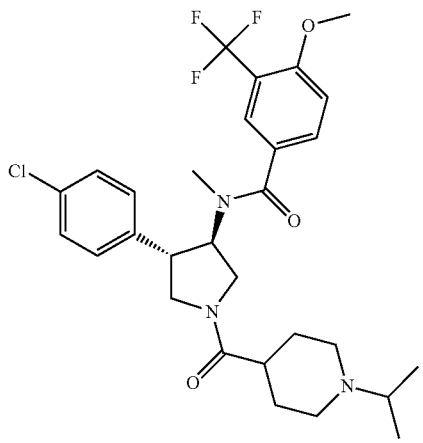 [SMILES: COc1ccc(C(=O)N(C)[C@H]2CN(C(=O)C3CCN(C(C)C)CC3)C[C@@H]2c2ccc(Cl)cc2)cc1C(F)(F)F]

To a solution of N-[(3RS,4SR)-4-(4-chloro-phenyl)-1-(piperidine-4-carbonyl)-pyrrolidin-3-yl]-4-methoxy-N-methyl-3-trifluoromethyl-benzamide (50 mg, 0.095 mmol) in dichloromethane (1 mL) was added under an atmosphere of nitrogen acetone (70 μl, 0.95 mmol) and sodium triacetoxyborohydride (81 mg, 0.38 mmol). The reaction mixture was stirred for 18 h at ambient temperature before it was treated with an aqueous solution of sodium carbonate (1 M, 10 ml) and stirred for 1 h at this temperature. It was diluted with ethyl acetate (15 mL). The aqueous layer was extracted with ethyl acetate (15 mL) and the organic layers were washed with brine (15 mL). The combined organic layers were dried over sodium sulfate and concentrated. Purification by chromatography (SiO$_2$, dichloromethane:methanol=100:0 to 70:30) afforded the title compound (40 mg, 73%) as a light brown oil. MS m/e: 566.3 [M]+.

EXAMPLE 105

N-[(3RS,4SR)-4-(4-Chloro-phenyl)-1-(1-cyclopropylmethyl-piperidine-4-carbonyl)-pyrrolidin-3-yl]-4-methoxy-N-methyl-3-trifluoromethyl-benzamide

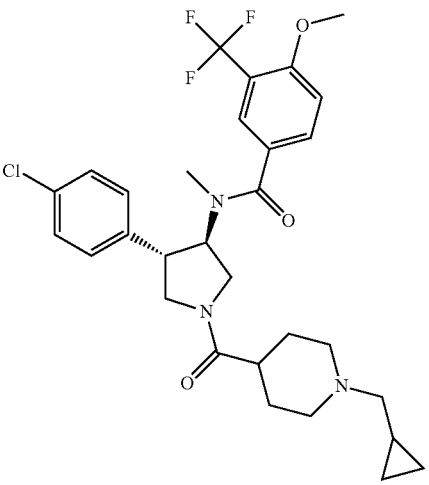 [SMILES: COc1ccc(C(=O)N(C)[C@H]2CN(C(=O)C3CCN(CC4CC4)CC3)C[C@@H]2c2ccc(Cl)cc2)cc1C(F)(F)F]

In analogy to the procedure described for the synthesis of example 104, the title compound N-[(3RS,4SR)-4-(4-chloro-phenyl)-1-(1-cyclopropylmethyl-piperidine-4-carbonyl)- pyrrolidin-3-yl]-4-methoxy-N-methyl-3-trifluoromethyl-benzamide was prepared from N-[(3RS,4SR)-4-(4-chloro-phenyl)-1-(piperidine-4-carbonyl)-pyrrolidin-3-yl]-4-methoxy-N-methyl-3-trifluoromethyl-benzamide using cyclopropanecarboxaldehyde instead of acetone and was obtained as a light brown oil. MS m/e: 578.2 [M]+.

EXAMPLE 106

N-{(3R,4S)-4-(3,4-Dichloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide

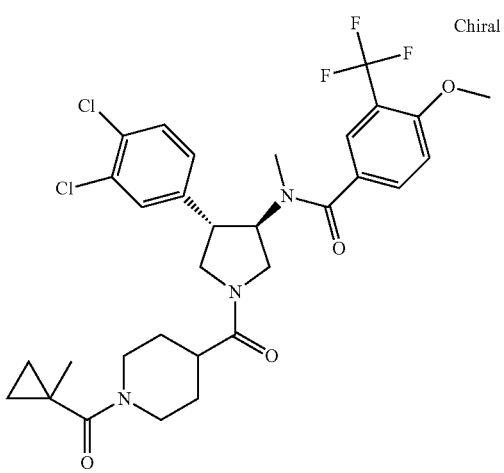 [SMILES: COc1ccc(C(=O)N(C)[C@H]2CN(C(=O)C3CCN(C(=O)C4(C)CC4)CC3)C[C@@H]2c2ccc(Cl)c(Cl)c2)cc1C(F)(F)F]

and

EXAMPLE 107

N-{(3S,4R)-4-(3,4-Dichloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide

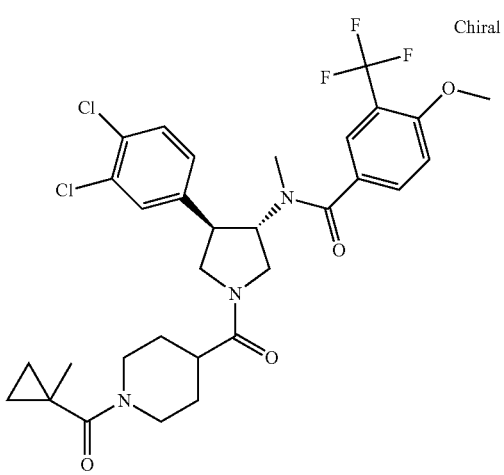 [SMILES: COc1ccc(C(=O)N(C)[C@@H]2CN(C(=O)C3CCN(C(=O)C4(C)CC4)CC3)C[C@H]2c2ccc(Cl)c(Cl)c2)cc1C(F)(F)F]

N-{(3SR,4RS)-4-(3,4-Dichloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide was subjected to column chromatography on chiral phase to yield N-{(3S,4R)-4-(3,4-Dichloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide (MS (m/e): 640.3 [M]+) as a light brown oil and N-{(3R,4S)- 4-(3,4-Dichloro-phenyl)-1-[1-(1-methyl-cyclopropanecarbonyl)-piperidine-4-carbonyl]-pyrrolidin-3-yl}-4-methoxy-N-methyl-3-trifluoromethyl-benzamide (MS (m/e): 640.3 [M]+) as a light brown oil.

EXAMPLE 108

5-Chloro-pyridine-2-carboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide

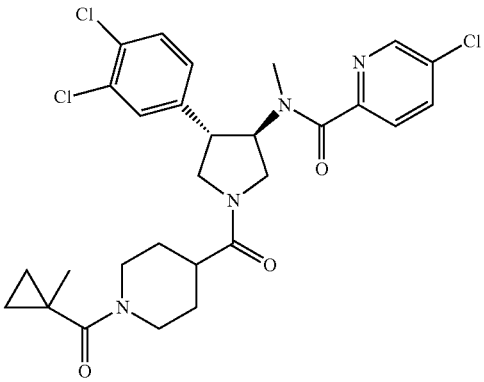 [SMILES: CN(C(=O)c1ccc(Cl)cn1)[C@H]1CN(C(=O)C2CCN(C(=O)C3(C)CC3)CC2)C[C@@H]1c1ccc(Cl)c(Cl)c1]

In analogy to the procedure described for the synthesis of example 97, the title compound 5-chloro-pyridine-2-carboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 5-chloro-2-pyridinecarboxylic acid instead of 4-chloro-3-(trifluoromethyl)benzoic acid and was obtained as a light brown oil. MS m/e: 577.2 [M]+.

EXAMPLE 109

3-Cyano-N-{(3RS,4SR)-4-(3,4-dichloro-phenyl)-1-[1-(1-methyl-cyclopropanecarbonyl)-piperidine-4-carbonyl]-pyrrolidin-3-yl}-4-fluoro-N-methyl-benzamide

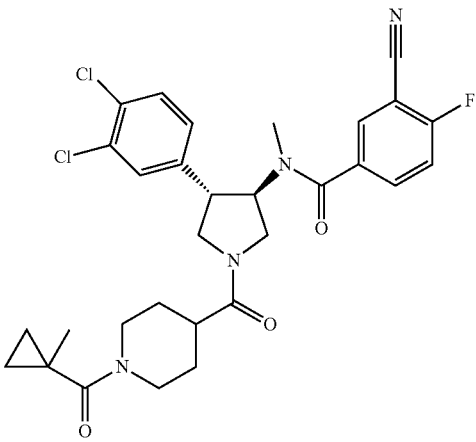 [SMILES: CN(C(=O)c1ccc(F)c(C#N)c1)[C@H]1CN(C(=O)C2CCN(C(=O)C3(C)CC3)CC2)C[C@@H]1c1ccc(Cl)c(Cl)c1]

In analogy to the procedure described for the synthesis of example 97, the title compound 3-cyano-N-{(3RS,4SR)-4-(3,4-dichloro-phenyl)-1-[1-(1-methyl-cyclopropanecarbonyl)-piperidine-4-carbonyl]-pyrrolidin-3-yl}-4-fluoro-N-methyl-benzamide was prepared from {4-[(3SR,4RS)-3-(3,4-dichloro-phenyl)-4-methylamino-pyrrolidine-1- carbonyl]-piperidin-1-yl}-(1-methyl-cyclopropyl)-methanone using 3-cyano-4-fluorobenzoic acid instead of 4-chloro-3-(trifluoromethyl)benzoic acid and was obtained as a light brown oil. MS m/e: 585.2 [M]+.

EXAMPLE 110

N-{(3RS,4SR)-4-(4-Chloro-phenyl)-1-[1-(3,3,3-trifluoro-propyl)-piperidine-4-carbonyl]-pyrrolidin-3-yl}-4-methoxy-N-methyl-3-trifluoromethyl-benzamide

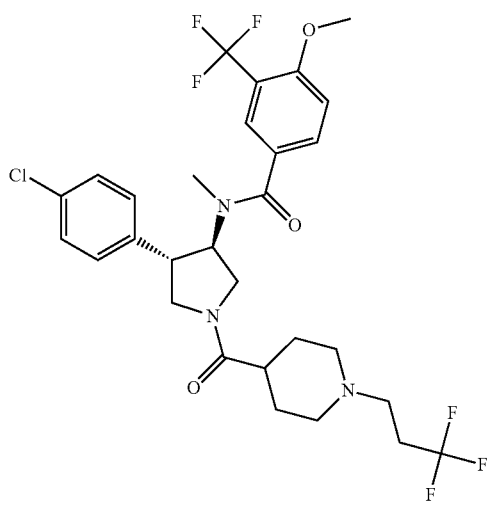 [SMILES: COc1ccc(C(=O)N(C)[C@H]2CN(C(=O)C3CCN(CCC(F)(F)F)CC3)C[C@@H]2c2ccc(Cl)cc2)cc1C(F)(F)F]

In analogy to the procedure described for the synthesis of example 104, the title compound N-{(3RS,4SR)-4-(4-chloro-phenyl)-1-[1-(3,3,3-trifluoro-propyl)-piperidine-4-carbonyl]-pyrrolidin-3-yl}-4-methoxy-N-methyl-3-trifluoromethyl-benzamide was prepared from N-[(3RS,4SR)-4-(4-chloro-phenyl)-1-(piperidine-4-carbonyl)-pyrrolidin-3-yl]-4-methoxy-N-methyl-3-trifluoromethyl-benzamide using 3,3,3-trifluoropropanal instead of acetone and was obtained as a light brown oil. MS m/e: 620.3 [M]+.

EXAMPLE 111

N-{(3RS,4SR)-4-(4-Chloro-phenyl)-1-[1-(3,3-dimethyl-butyl)-piperidine-4-carbonyl]-pyrrolidin-3-yl}-4-methoxy-N-methyl-3-trifluoromethyl-benzamide

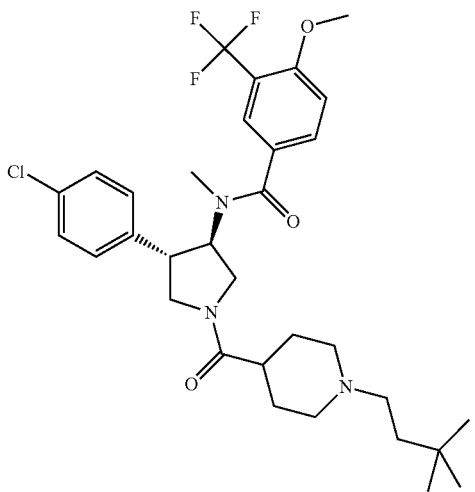 [SMILES: COc1ccc(C(=O)N(C)[C@H]2CN(C(=O)C3CCN(CCC(C)(C)C)CC3)C[C@@H]2c2ccc(Cl)cc2)cc1C(F)(F)F]

In analogy to the procedure described for the synthesis of example 104, the title compound N-{(3RS,4SR)-4-(4-chloro-phenyl)-1-[1-(3,3-dimethyl-butyl)-piperidine-4-carbonyl]-pyrrolidin-3-yl}-4-methoxy-N-methyl-3-trifluoromethyl-benzamide was prepared from N-[(3RS,4SR)-4-(4-chloro-phenyl)-1-(piperidine-4-carbonyl)-pyrrolidin-3-yl]-4-methoxy-N-methyl-3-trifluoromethyl-benzamide using 3,3-dimethylbutyraldehyde instead of acetone and was obtained as a light brown oil. MS m/e: 608.2 [M]+.

EXAMPLE 112

Cis-4-Hydroxy-cyclohexanecarboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide

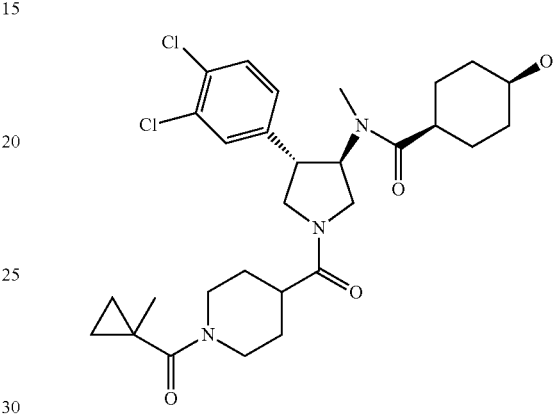

In analogy to the procedure described for the synthesis of example 97, the title compound cis-4-hydroxy-cyclohexanecarboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using cis-4-hydroxycyclohexanecarboxylic acid instead of 4-chloro-3-(trifluoromethyl)benzoic acid and was obtained as a light brown oil. MS m/e: 564.4 [M]+.

EXAMPLE 113

2-Cyclopentyl-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-acetamide

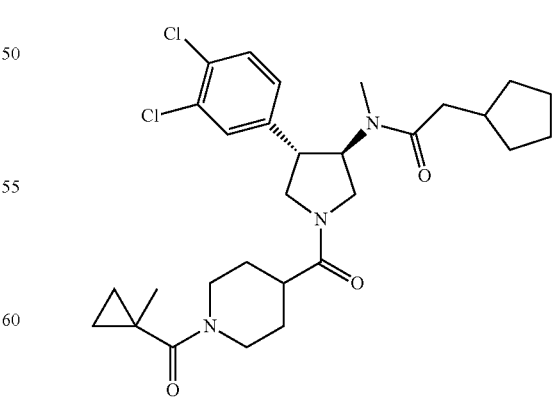

In analogy to the procedure described for the synthesis of example 97, the title compound 2-cyclopentyl-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-acetamide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using cyclopentylacetic acid instead of 4-chloro-3-(trifluoromethyl)benzoic acid and was obtained as a light brown oil. MS m/e: 548.3 [M]+.

EXAMPLE 114

3-Cyclopropyl-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-propionamide

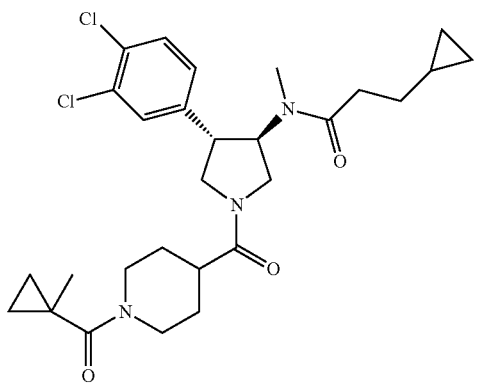 [SMILES: CN(C(=O)CCC1CC1)[C@H]1CN(C(=O)C2CCN(C(=O)C3(C)CC3)CC2)C[C@@H]1c1ccc(Cl)c(Cl)c1]

In analogy to the procedure described for the synthesis of example 97, the title compound 3-cyclopropyl-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-propionamide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 3-cyclopropylpropionic acid instead of 4-chloro-3-(trifluoromethyl)benzoic acid and was obtained as a light brown oil. MS m/e: 534.3 [M]+.

EXAMPLE 115

N-{(3RS,4SR)-4-(3,4-Dichloro-phenyl)-1-[1-(1-methyl-cyclopropanecarbonyl)-piperidine-4-carbonyl]-pyrrolidin-3-yl}-3,3,N-trimethyl-butyramide

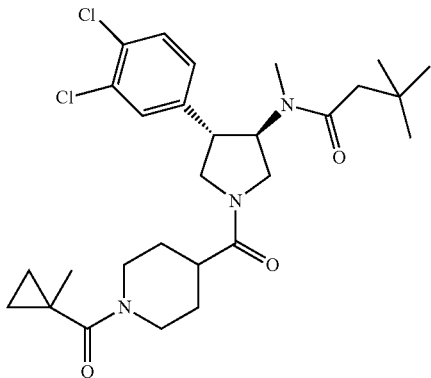 [SMILES: CN(C(=O)CC(C)(C)C)[C@H]1CN(C(=O)C2CCN(C(=O)C3(C)CC3)CC2)C[C@@H]1c1ccc(Cl)c(Cl)c1]

In analogy to the procedure described for the synthesis of example 97, the title compound N-{(3RS,4SR)-4-(3,4-dichloro-phenyl)-1-[1-(1-methyl-cyclopropanecarbonyl)-piperidine-4-carbonyl]-pyrrolidin-3-yl}-3,3,N-trimethyl-butyramide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using tert-butylacetic acid instead of 4-chloro-3-(trifluoromethyl)benzoic acid and was obtained as a light brown oil. MS m/e: 536.3 [M]+.

EXAMPLE 116

N-{(3RS,4SR)-4-(3,4-Dichloro-phenyl)-1-[1-(1-methyl-cyclopropanecarbonyl)-piperidine-4-carbonyl]-pyrrolidin-3-yl}-2-(4-fluoro-phenyl)-3,N-dimethyl-butyramide

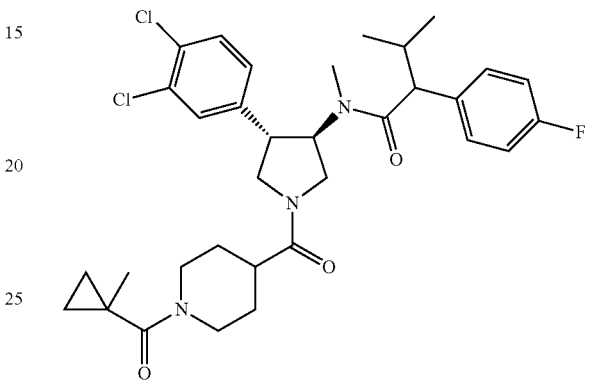

In analogy to the procedure described for the synthesis of example 97, the title compound N-{(3RS,4SR)-4-(3,4-dichloro-phenyl)-1-[1-(1-methyl-cyclopropanecarbonyl)-piperidine-4-carbonyl]-pyrrolidin-3-yl}-2-(4-fluoro-phenyl)-3,N-dimethyl-butyramide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 2-(4-fluoro-phenyl)-3-methyl-butyric acid instead of 4-chloro-3-(trifluoromethyl)benzoic acid and was obtained as a light brown oil. MS m/e: 616.4 [M]+.

EXAMPLE 117

1-(4-Fluoro-phenyl)-cyclopentanecarboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide

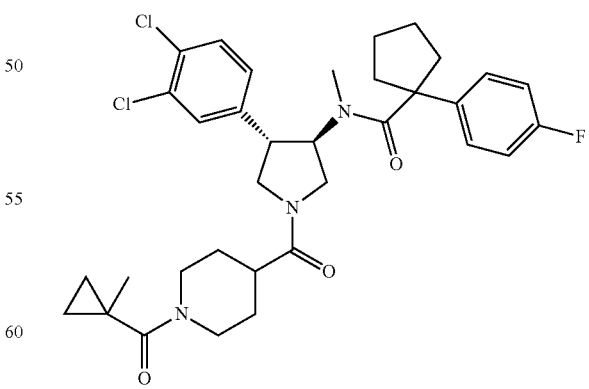

In analogy to the procedure described for the synthesis of example 97, the title compound 1-(4-fluoro-phenyl)-cyclopentanecarboxylic acid {(3RS,4SR)-4-(3,4-dichloro-phenyl)-1-[1-(1-methyl-cyclopropanecarbonyl)-piperidine-4- carbonyl]-pyrrolidin-3-yl}-methyl-amide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 1-(4-fluoro-phenyl)-cyclopentanecarboxylic acid instead of 4-chloro-3-(trifluoromethyl) benzoic acid and was obtained as a light brown oil. MS m/e: 628.3 [M]+.

EXAMPLE 118

N-{(3R,4S)-4-(3,4-Dichloro-phenyl)-1-[1-(1-methyl-cyclopropanecarbonyl)-piperidine-4-carbonyl]-pyrrolidin-3-yl}-2-(4-fluoro-phenyl)-N-methyl-acetamide

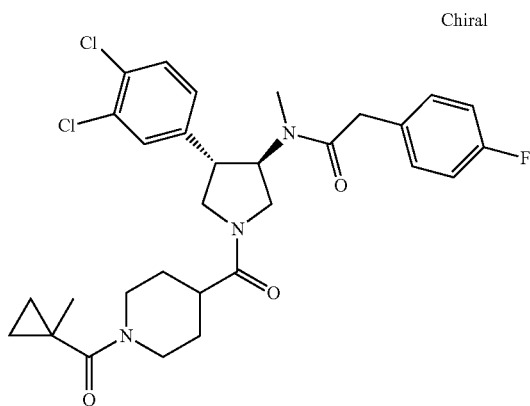 [SMILES: CN(C(=O)Cc1ccc(F)cc1)[C@H]1CN(C(=O)C2CCN(C(=O)C3(C)CC3)CC2)C[C@@H]1c1ccc(Cl)c(Cl)c1]

and

EXAMPLE 119

N-{(3S,4R)-4-(3,4-Dichloro-phenyl)-1-[1-(1-methyl-cyclopropanecarbonyl)-piperidine-4-carbonyl]-pyrrolidin-3-yl}-2-(4-fluoro-phenyl)-N-methyl-acetamide

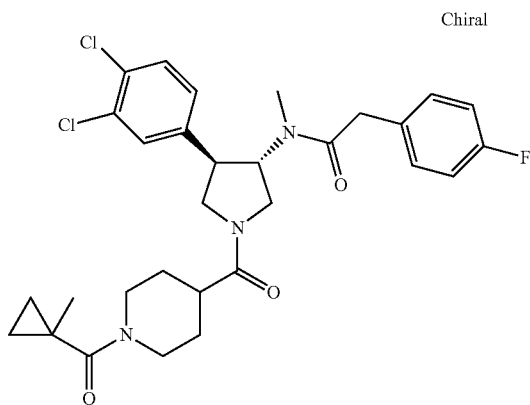 [SMILES: CN(C(=O)Cc1ccc(F)cc1)[C@@H]1CN(C(=O)C2CCN(C(=O)C3(C)CC3)CC2)C[C@H]1c1ccc(Cl)c(Cl)c1]

N-{(3RS,4SR)-4-(3,4-Dichloro-phenyl)-1-[1-(1-methyl-cyclopropanecarbonyl)-piperidine-4-carbonyl]-pyrrolidin-3-yl}-2-(4-fluoro-phenyl)-N-methyl-acetamide was subjected to column chromatography on chiral phase to yield N-{(3R,4S)-4-(3,4-Dichloro-phenyl)-1-[1-(1-methyl-cyclopropanecarbonyl)-piperidine-4-carbonyl]-pyrrolidin-3-yl}-2-(4-fluoro-phenyl)-N-methyl-acetamide (MS (m/e): 574.2 [M]+) as a light brown oil and N-{(3S,4R)-4-(3,4-Dichloro-phenyl)-1-[1-(1-methyl-cyclopropanecarbonyl)-piperidine-4-carbonyl]-pyrrolidin-3-yl}-2-(4-fluoro-phenyl)-N-methyl-acetamide (MS (m/e): 574.2 [M]+) as a light brown oil.

EXAMPLE 120

N-{(3RS,4SR)-4-(4-Chloro-phenyl)-1-[1-(2,2-dimethyl-propyl)-piperidine-4-carbonyl]-pyrrolidin-3-yl}-4-methoxy-N-methyl-3-trifluoromethyl-benzamide

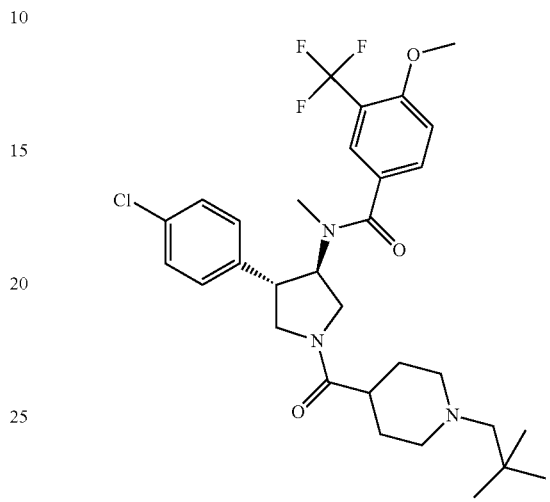

In analogy to the procedure described for the synthesis of example 104, the title compound N-{(3RS,4SR)-4-(4-chloro-phenyl)-1-[1-(2,2-dimethyl-propyl)-piperidine-4-carbonyl]-pyrrolidin-3-yl}-4-methoxy-N-methyl-3-trifluoromethyl-benzamide was prepared from N-[(3RS,4SR)-4-(4-chloro-phenyl)-1-(piperidine-4-carbonyl)-pyrrolidin-3-yl]-4-methoxy-N-methyl-3-trifluoromethyl-benzamide using trimethylacetaldehyde (75% in tert butanol) instead of acetone and was obtained as a light brown oil. MS m/e: 594.3 [M]+.

EXAMPLE 121

N-[(3RS,4SR)-4-(4-Chloro-phenyl)-1-(1-ethyl-piperidine-4-carbonyl)-pyrrolidin-3-yl]-4-methoxy-N-methyl-3-trifluoromethyl-benzamide

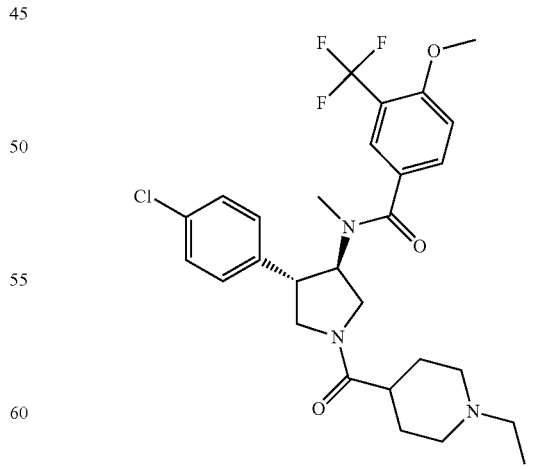

In analogy to the procedure described for the synthesis of example 104, the title compound N-[(3RS,4SR)-4-(4-chloro-phenyl)-1-(1-ethyl-piperidine-4-carbonyl)-pyrrolidin-3-yl]-4-methoxy-N-methyl-3-trifluoromethyl-benzamide was prepared from N-[(3RS,4SR)-4-(4-chloro-phenyl)-1-

(piperidine-4-carbonyl)-pyrrolidin-3-yl]-4-methoxy-N-methyl-3-trifluoromethyl-benzamide using acetaldehyde instead of acetone and was obtained as a light brown oil. MS m/e: 552.2 [M]+.

EXAMPLE 122

N-{(3RS,4SR)-4-(4-Chloro-2-methyl-phenyl)-1-[1-(1-methyl-cyclopropanecarbonyl)-piperidine-4-carbonyl]-pyrrolidin-3-yl}-4-methoxy-3-trifluoromethyl-benzamide

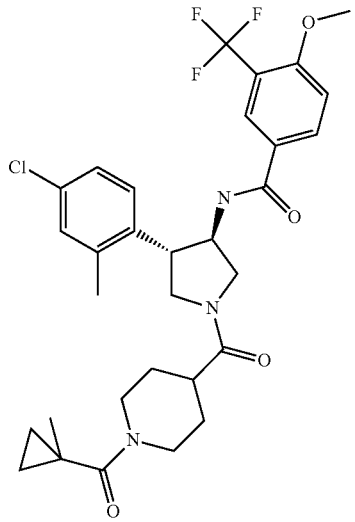

a) 4-Chloro-2-methyl-1-((E)-2-nitro-vinyl)-benzene

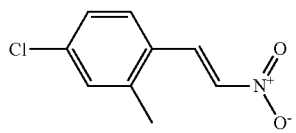

Under an atmosphere of nitrogen was added to a solution of 4-chloro-2-methylbenzaldehyde (10.0 g, 64.9 g) in acetic acid (70 mL) ammonium acetate (11.5 g, 149 mmol) and nitromethane (10.0 ml, 185 mmol). The solution was stirred at reflux (oil bath 140° C.) for 2 h. After cooling to ambient temperature water (70 mL) was added and extracted twice with ethyl acetate (70 mL). The organic layers were washed with water (70 mL) and brine (70 mL) and were dried over sodium sulfate. The filtrated was concentrated and the resulting solid was suspended in methanol (30 mL), at 0° C. filtered off and was washed with cold methanol (10 mL) affording the title compound (8.30 g, 65%) as a yellow solid. MS m/e: 197.0 [M]+.

b) (3SR,4RS)-1-Benzyl-3-(4-chloro-2-methyl-phenyl)-4-nitro-pyrrolidine

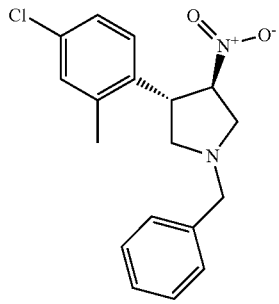 [SMILES: Cc1cc(Cl)ccc1[C@H]1CN(Cc2ccccc2)C[C@@H]1[N+](=O)[O-]]

In analogy to the procedure described for the synthesis of pyrrolidine intermediate VIII-1 (step a), the title compound (3SR,4RS)-1-benzyl-3-(4-chloro-2-methyl-phenyl)-4-nitro-pyrrolidine was prepared from 4-chloro-2-methyl-1-((E)-2-nitro-vinyl)-benzene instead of 1,2-dichloro-4-((E)-2-nitro-vinyl)-benzene and was obtained as a light brown oil. MS m/e: 331.1 [M+H]+.

c) (3RS,4SR)-1-Benzyl-4-(4-chloro-2-methyl-phenyl)-pyrrolidin-3-ylamine

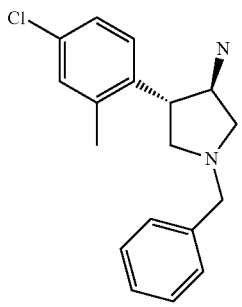 [SMILES: Cc1cc(Cl)ccc1[C@H]1CN(Cc2ccccc2)C[C@@H]1N]

In analogy to the procedure described for the synthesis of pyrrolidine intermediate VIII-1 (step b), the title compound (3RS,4SR)-1-benzyl-4-(4-chloro-2-methyl-phenyl)-pyrrolidin-3-ylamine was prepared from (3SR,4RS)-1-benzyl-3-(4-chloro-2-methyl-phenyl)-4-nitro-pyrrolidine instead of (3SR,4RS)-1-benzyl-3-(3,4-dichloro-phenyl)-4-nitro-pyrrolidine and was obtained as a light brown foam. MS m/e: 301.2 [M+H]+.

d) [(3RS,4SR)-1-Benzyl-4-(4-chloro-2-methyl-phenyl)-pyrrolidin-3-yl]-methyl-amine

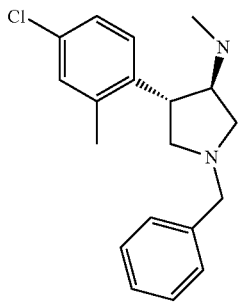 [SMILES: CN[C@H]1CN(Cc2ccccc2)C[C@@H]1c1ccc(Cl)cc1C]

In analogy to the procedure described for the synthesis of pyrrolidine intermediate VIII-1 (step c), the title compound [(3RS,4SR)-1-benzyl-4-(4-chloro-2-methyl-phenyl)-pyrrolidin-3-yl]-methyl-amine was prepared from (3RS,4SR)-1-benzyl-4-(4-chloro-2-methyl-phenyl)-pyrrolidin-3-ylamine instead of (3RS,4SR)-1-benzyl-4-(3,4-dichloro-phenyl)-pyrrolidin-3-ylamine and was obtained as a colorless oil. MS m/e: 315.1 [M+H]+.

e) N-[(3RS,4SR)-1-Benzyl-4-(4-chloro-2-methyl-phenyl)-pyrrolidin-3-yl]-4-methoxy-N-methyl-3-trifluoromethyl-benzamide

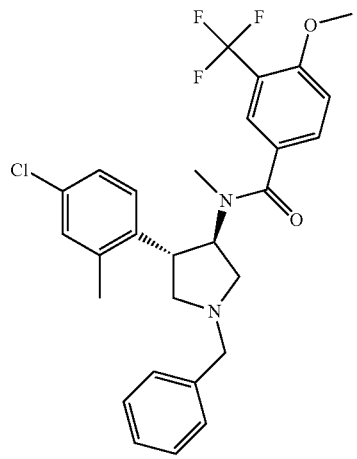 [SMILES: COc1ccc(C(=O)N(C)[C@H]2CN(Cc3ccccc3)C[C@@H]2c2ccc(Cl)cc2C)cc1C(F)(F)F]

In analogy to the procedure described for the synthesis of pyrrolidine intermediate VIII-1 (step d), the title compound N-[(3RS,4SR)-1-benzyl-4-(4-chloro-2-methyl-phenyl)-pyrrolidin-3-yl]-4-methoxy-N-methyl-3-trifluoromethyl-benzamide was prepared from [(3RS,4SR)-1-benzyl-4-(4-chloro-2-methyl-phenyl)-pyrrolidin-3-yl]-methyl-amine instead of [(3RS,4SR)-1-benzyl-4-(3,4-dichloro-phenyl)-pyrrolidin-3-yl]-methyl-amine and was obtained as a light yellow oil. MS m/e: 517.1 [M+H]$^+$.

f) N-[(3RS,4SR)-4-(4-Chloro-2-methyl-phenyl)-pyrrolidin-3-yl]-4-methoxy-N-methyl-3-trifluoromethyl-benzamide

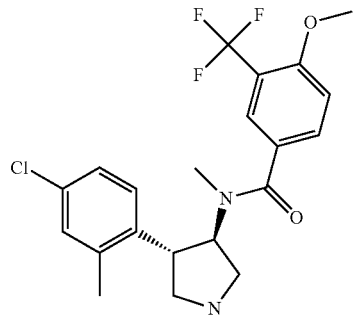 [SMILES: COc1ccc(C(=O)N(C)[C@H]2CNC[C@@H]2c2ccc(Cl)cc2C)cc1C(F)(F)F]

In analogy to the procedure described for the synthesis of example 87 (step b), the title compound N-[(3RS,4SR)-4-(4-chloro-2-methyl-phenyl)-pyrrolidin-3-yl]-4-methoxy-N-methyl-3-trifluoromethyl-benzamide was prepared from N-[(3RS,4SR)-1-benzyl-4-(4-chloro-2-methyl-phenyl)-pyrrolidin-3-yl]-4-methoxy-N-methyl-3-trifluoromethyl-benzamide instead of N-[(3RS,4SR)-1-benzyl-4-(4-chloro-phenyl)-pyrrolidin-3-yl]-4-methoxy-N-methyl-3-trifluoromethyl-benzamide and was obtained as a yellow oil. MS m/e: 427.2 [M+H]$^+$.

g) N-{(3RS,4SR)-4-(4-Chloro-2-methyl-phenyl)-1-[1-(1-methyl-cyclopropanecarbonyl)-piperidine-4-carbonyl]-pyrrolidin-3-yl}-4-methoxy-3-trifluoromethyl-benzamide In analogy to the procedure described for the synthesis of example 87 (step c), the title compound N-{(3RS,4SR)-4-(4-chloro-2-methyl-phenyl)-1-[1-(1-methyl-cyclopropanecarbonyl)-piperidine-4-carbonyl]-pyrrolidin-3-yl}-4-methoxy-3-trifluoromethyl-benzamide was prepared from N-[(3RS,4SR)-4-(4-chloro-2-methyl-phenyl)-pyrrolidin-3-yl]-4-methoxy-N-methyl-3-trifluoromethyl-benzamide instead of N-[(3RS,4SR)-4-(4-chloro-phenyl)-pyrrolidin-3-yl]-4-methoxy-N-methyl-3-trifluoromethyl-benzamide and was obtained as a colorless oil. MS m/e: 606.3 [M]$^+$.

EXAMPLE 123

N-{(3R,4S)-4-(4-Chloro-2-methyl-phenyl)-1-[1-(1-methyl-cyclopropanecarbonyl)-piperidine-4-carbonyl]-pyrrolidin-3-yl}-4-methoxy-N-methyl-3-trifluoromethyl-benzamide

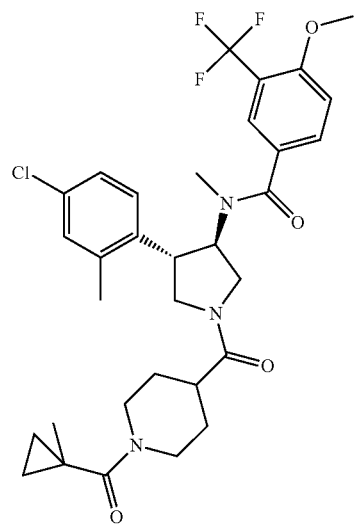 [SMILES: COc1ccc(C(=O)N(C)[C@H]2CN(C(=O)C3CCN(C(=O)C4(C)CC4)CC3)C[C@@H]2c2ccc(Cl)cc2C)cc1C(F)(F)F]

In analogy to the procedure described for the synthesis of example 87 (step c), the title compound N-{(3RS,4SR)-4-(4-chloro-2-methyl-phenyl)-1-[1-(1-methyl-cyclopropanecarbonyl)-piperidine-4-carbonyl]-pyrrolidin-3-yl}-4-methoxy-N-methyl-3-trifluoromethyl-benzamide was prepared from N-[(3RS,4SR)-4-(4-chloro-2-methyl-phenyl)-pyrrolidin-3-yl]-4-methoxy-N-methyl-3-trifluoromethyl-benzamide instead of N-[(3RS,4SR)-4-(4-chloro-phenyl)-pyrrolidin-3-yl]-4-methoxy-N-methyl-3-trifluoromethyl-benzamide and was obtained as a colorless oil. MS m/e: 620.3 [M]$^+$.

EXAMPLE 124

N-{(3RS,4SR)-4-(3,4-Dichloro-phenyl)-1-[1-(1-methyl-cyclopropanecarbonyl)-piperidine-4-carbonyl]-pyrrolidin-3-yl}-N-methyl-2-(tetrahydro-pyran-4-yl)-acetamide

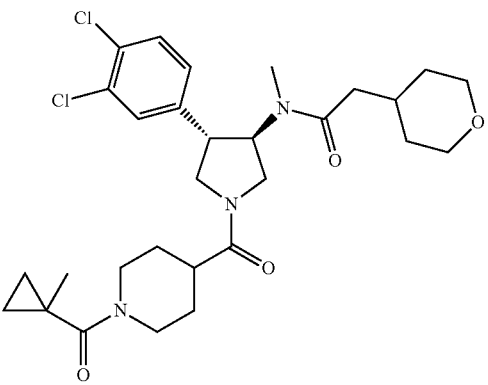 [SMILES: CN(C(=O)CC1CCOCC1)[C@H]1CN(C(=O)C2CCN(C(=O)C3(C)CC3)CC2)C[C@@H]1c1ccc(Cl)c(Cl)c1]

In analogy to the procedure described for the synthesis of example 97, the title compound N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-2-(tetrahydro-pyran-4-yl)-acetamide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using tetrahydropyran-4-yl-acetic acid instead of 4-chloro-3-(trifluoromethyl)benzoic acid and was obtained as a light brown foam. MS m/e: 564.4 [M]+.

EXAMPLE 125

N-{(3RS,4SR)-4-(3,4-Dichloro-phenyl)-1-[1-(1-methyl-cyclopropanecarbonyl)-piperidine-4-carbonyl]-pyrrolidin-3-yl}-2-(4-fluoro-phenyl)-N-methyl-isobutyramide

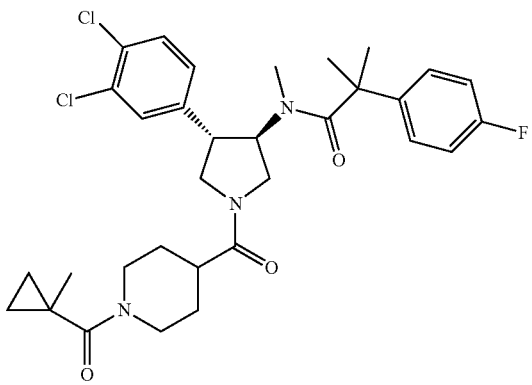 [SMILES: CN(C(=O)C(C)(C)c1ccc(F)cc1)[C@H]1CN(C(=O)C2CCN(C(=O)C3(C)CC3)CC2)C[C@@H]1c1ccc(Cl)c(Cl)c1]

In analogy to the procedure described for the synthesis of example 97, the title compound N-{(3RS,4SR)-4-(3,4-dichloro-phenyl)-1-[1-(1-methyl-cyclopropanecarbonyl)-piperidine-4-carbonyl]-pyrrolidin-3-yl}-2-(4-fluoro-phenyl)-N-methyl-isobutyramide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 2-(4-fluoro-phenyl)-2-methyl-propionic acid instead of 4-chloro-3-(trifluoromethyl)benzoic acid and was obtained as a light brown oil. MS m/e: 602.3 [M]+.

EXAMPLE 126

N-{(3RS,4SR)-4-(4-Chloro-phenyl)-1-[1-(3-methylsulfanyl-propyl)-piperidine-4-carbonyl]-pyrrolidin-3-yl}-4-methoxy-N-methyl-3-trifluoromethyl-benzamide

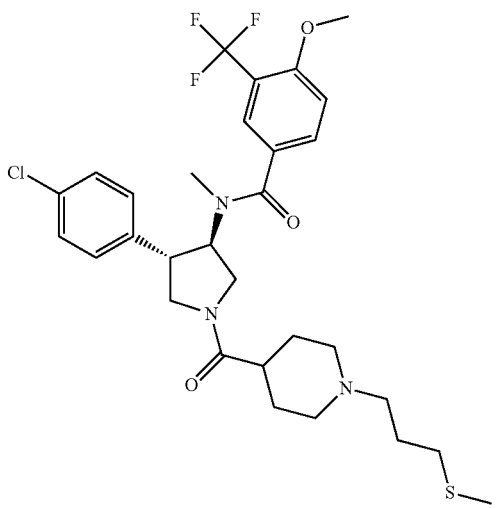 [SMILES: COc1ccc(C(=O)N(C)[C@H]2CN(C(=O)C3CCN(CCCSC)CC3)C[C@@H]2c2ccc(Cl)cc2)cc1C(F)(F)F]

In analogy to the procedure described for the synthesis of example 104, the title compound N-{(3RS,4SR)-4-(4-chloro-phenyl)-1-[1-(3-methylsulfanyl-propyl)-piperidine-4-carbonyl]-pyrrolidin-3-yl}-4-methoxy-N-methyl-3-trifluoromethyl-benzamide was prepared from N-[(3RS,4SR)-4-(4-chloro-phenyl)-1-(piperidine-4-carbonyl)-pyrrolidin-3-yl]-4-methoxy-N-methyl-3-trifluoromethyl-benzamide using 3-(methylthio)propionaldehyde instead of acetone and was obtained as a colorless oil. MS m/e: 612.1 [M]+.

EXAMPLE 127

N-[(3RS,4SR)-4-(3,4-Dichloro-phenyl)-1-(4-methoxy-cyclohexanecarbonyl)-pyrrolidin-3-yl]-2-(4-fluoro-phenyl)-N-methyl-acetamide

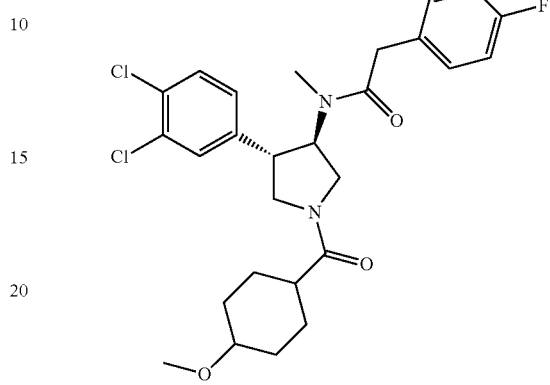

a) N-[(3RS,4SR)-1-Benzyl-4-(3,4-dichloro-phenyl)-pyrrolidin-3-yl]-2-(4-fluoro-phenyl)-N-methyl-acetamide

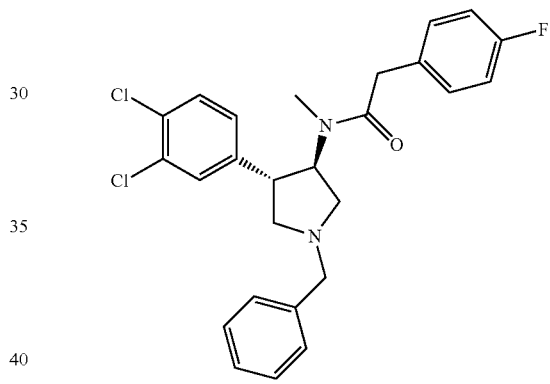

In analogy to the procedure described for the synthesis of example 97, the title compound N-[(3RS,4SR)-1-benzyl-4-(3,4-dichloro-phenyl)-pyrrolidin-3-yl]-2-(4-fluoro-phenyl)-N-methyl-acetamide was prepared from [(3R,4S)-1-benzyl-4-(3,4-dichloro-phenyl)-pyrrolidin-3-yl]-methyl-amine using 4-fluorophenylacetic acid instead of 4-chloro-3-(trifluoromethyl)benzoic acid and was obtained as a light yellow oil. MS m/e: 471.2 [M]+.

b) N-[(3RS,4SR)-4-(3,4-Dichloro-phenyl)-pyrrolidin-3-yl]-2-(4-fluoro-phenyl)-N-methyl-acetamide

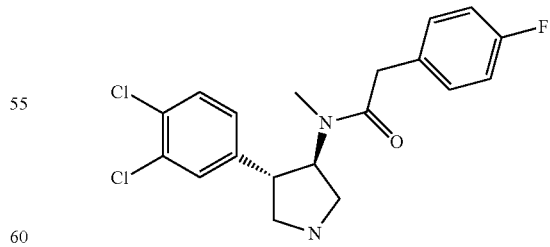

In analogy to the procedure described for the synthesis of example 87 (step b), the title compound N-[(3RS,4SR)-4-(3,4-dichloro-phenyl)-pyrrolidin-3-yl]-2-(4-fluoro-phenyl)-N-methyl-acetamide was prepared from N-[(3RS,4SR)-1-benzyl-4-(3,4-dichloro-phenyl)-pyrrolidin-3-yl]-2-(4-fluoro-phenyl)-N-methyl-acetamide and was obtained as a brown oil. MS m/e: 381.1 [M]+.

c) N-[(3RS,4SR)-4-(3,4-Dichloro-phenyl)-1-(4-methoxy-cyclohexanecarbonyl)-pyrrolidin-3-yl]-2-(4-fluoro-phenyl)-N-methyl-acetamide In analogy to the procedure described for the synthesis of example 87 (step c), the title compound N-[(3RS,4SR)-4-(3,4-dichloro-phenyl)-1-(4-methoxy-cyclohexanecarbonyl)-pyrrolidin-3-yl]-2-(4-fluoro-phenyl)-N-methyl-acetamide was prepared from N-[(3RS,4SR)-4-(3,4-dichloro-phenyl)-pyrrolidin-3-yl]-2-(4-fluoro-phenyl)-N-methyl-acetamide using 4-methoxycylcohexanecarboxylic acid instead of 1-(1-methyl-cyclopropanecarbonyl)-piperidine-4-carboxylic acid and was obtained as a colorless oil. MS m/e: 521.3 [M]$^+$.

EXAMPLE 128

N-{(3RS,4SR)-4-(3,4-Dichloro-phenyl)-1-[2-(1,1-dioxo-1lambda*6*-thiomorpholin-4-yl)-acetyl]-pyrrolidin-3-yl}-2-(4-fluoro-phenyl)-N-methyl-acetamide

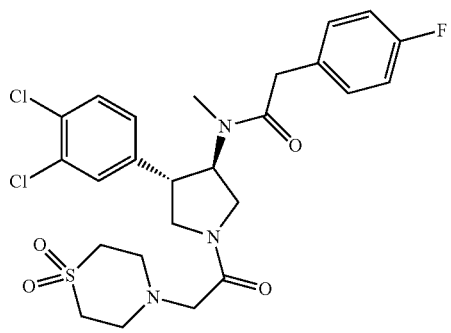 [SMILES: CN(C(=O)Cc1ccc(F)cc1)[C@H]1CN(C(=O)CN2CCS(=O)(=O)CC2)C[C@@H]1c1ccc(Cl)c(Cl)c1]

In analogy to the procedure described for the synthesis of example 87 (step c), the title compound N-{(3RS,4SR)-4-(3,4-dichloro-phenyl)-1-[2-(1,1-dioxo-1lambda*6*-thiomorpholin-4-yl)-acetyl]-pyrrolidin-3-yl}-2-(4-fluoro-phenyl)-N-methyl-acetamide was prepared from N-[(3RS,4SR)-4-(3,4-dichloro-phenyl)-pyrrolidin-3-yl]-2-(4-fluoro-phenyl)-N-methyl-acetamide using (1,1-Dioxo-1lambda*6*-thiomorpholin-4-yl)-acetic acid instead of 1-(1-methyl-cyclopropanecarbonyl)-piperidine-4-carboxylic acid and was obtained as a colorless oil. MS m/e: 556.1 [M]$^+$.

EXAMPLE 129

N-[(3RS,4SR)-4-(3,4-Dichloro-phenyl)-1-(morpholine-4-carbonyl)-pyrrolidin-3-yl]-2-(4-fluoro-phenyl)-N-methyl-acetamide

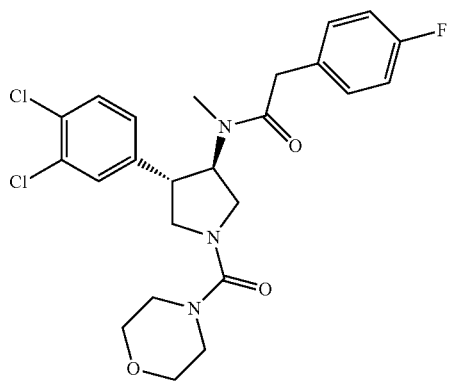 [SMILES: CN(C(=O)Cc1ccc(F)cc1)[C@H]1CN(C(=O)N2CCOCC2)C[C@@H]1c1ccc(Cl)c(Cl)c1]

Coupling according to general procedure I:
Pyrrolidine intermediate: N-[(3RS,4SR)-4-(3,4-dichloro-phenyl)-pyrrolidin-3-yl]-2-(4-fluoro-phenyl)-N-methyl-acetamide,
Carbamoyl chloride: 4-Morpholinecarbonyl chloride
ES-MS m/e: 494.2 (M$^+$).

EXAMPLE 130

N-[(3RS,4SR)-4-(3,4-Dichloro-phenyl)-1-(4-methanesulfonyl-piperazine-1-carbonyl)-pyrrolidin-3-yl]-2-(4-fluoro-phenyl)-N-methyl-acetamide

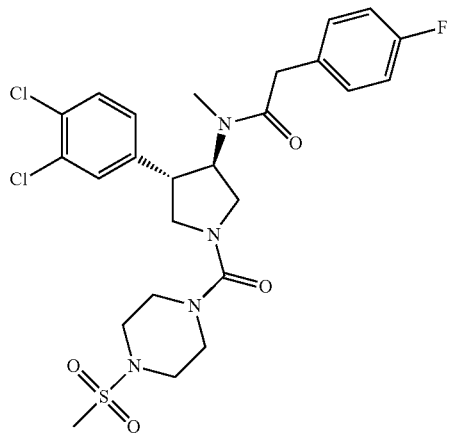 [SMILES: CN(C(=O)Cc1ccc(F)cc1)[C@H]1CN(C(=O)N2CCN(S(C)(=O)=O)CC2)C[C@@H]1c1ccc(Cl)c(Cl)c1]

Coupling according to general procedure I:
Pyrrolidine intermediate: N-[(3RS,4SR)-4-(3,4-dichloro-phenyl)-pyrrolidin-3-yl]-2-(4-fluoro-phenyl)-N-methyl-acetamide,
Carbamoyl chloride: 4-Methanesulfonyl-piperazine-1-carbonyl chloride
ES-MS m/e: 571.1 (M$^+$).

EXAMPLE 131

N-{(3RS,4SR)-4-(4-Chloro-phenyl)-1-[1-(3-methanesulfonyl-propyl)-piperidine-4-carbonyl]-pyrrolidin-3-yl}-4-methoxy-N-methyl-3-trifluoromethyl-benzamide

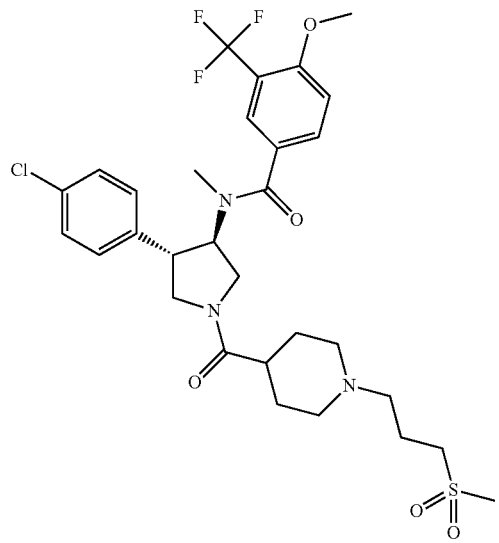 [SMILES: COc1ccc(C(=O)N(C)[C@H]2CN(C(=O)C3CCN(CCCS(C)(=O)=O)CC3)C[C@@H]2c2ccc(Cl)cc2)cc1C(F)(F)F]

To a solution of N-{(3RS,4SR)-4-(4-chloro-phenyl)-1-[1-(3-methylsulfanyl-propyl)-piperidine-4-carbonyl]-pyrrolidin-3-yl}-4-methoxy-N-methyl-3-trifluoromethyl-benzamide (80 mg, 0.13 mmol) in dichloromethane (2 mL) was added under an atmosphere of nitrogen m-chloroperbenzoic acid (47 mg, 0.27 mmol) and stirred for 3 d at ambient temperature. Further addition of m-chloroperbenzoic acid (47 mg, 0.27 mmol) was followed by stirring for 3 h at ambient temperature. After the addition of an aqueous saturated solution of sodium bisulfate (10 mL) and water (10 mL) it was stirred for 1 h at ambient temperature. The reaction mixture was basified by addition of an aqueous solution of sodium carbonate (1 M). The aqueous layer was extracted with dichloromethane (20 mL) and the organic layers were washed with water (15 mL) and dried over sodium sulfate. Purification by chromatography (SiO$_2$, heptane:(ethyl acetate:triethylamine=95:5):methanol=20:80:0 to 0:85:15) afforded the title compound (70 mg, 83%) as a light brown oil. MS m/e: 644.2 [M]$^+$.

EXAMPLE 132

4-{(3SR,4RS)-3-(3,4-Dichloro-phenyl)-4-[(4-methoxy-3-trifluoromethyl-benzoyl)-methyl-amino]-pyrrolidine-1-carbonyl}-piperidine-1-carboxylic acid tert-butyl ester

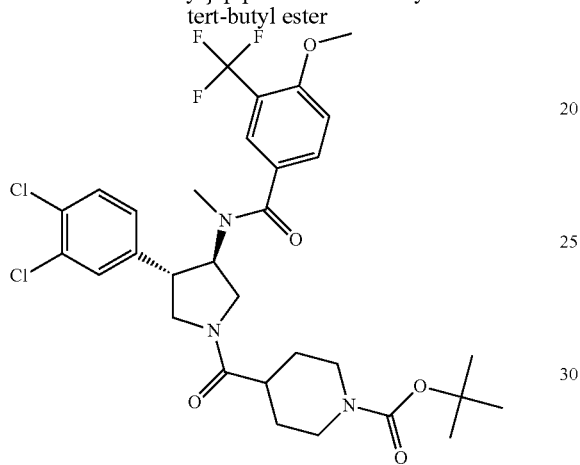

In analogy to the procedure described for the synthesis of example 95, the title compound 4-{(3SR,4RS)-3-(3,4-dichloro-phenyl)-4-[(4-methoxy-3-trifluoromethyl-benzoyl)-methyl-amino]-pyrrolidine-1-carbonyl}-piperidine-1-carboxylic acid tert-butyl ester was prepared from N-[(3RS,4SR)-4-(3,4-dichloro-phenyl)-pyrrolidin-3-yl]-4-methoxy-N-methyl-3-trifluoromethyl-benzamide instead of N-[(3RS,4SR)-4-(4-chloro-phenyl)-pyrrolidin-3-yl]-4-methoxy-N-methyl-3-trifluoromethyl-benzamide and was obtained as a light brown oil. MS m/e: 658.3 [M]$^+$.

EXAMPLE 133

N-[(3RS,4SR)-4-(3,4-Dichloro-phenyl)-1-(piperidine-4-carbonyl)-pyrrolidin-3-yl]-4-methoxy-N-methyl-3-trifluoromethyl-benzamide

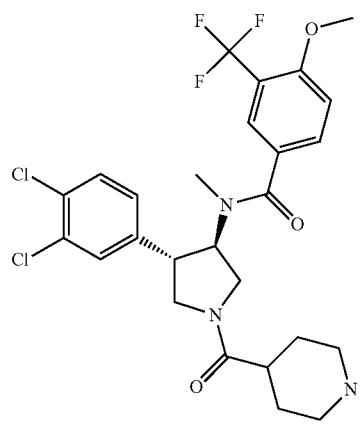 [SMILES: COc1ccc(C(=O)N(C)[C@H]2CN(C(=O)C3CCNCC3)C[C@@H]2c2ccc(Cl)c(Cl)c2)cc1C(F)(F)F]

In analogy to the procedure described for the synthesis of example 103, the title compound N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide was prepared from 4-{(3SR,4RS)-3-(3,4-dichloro-phenyl)-4-[(4-methoxy-3-trifluoromethyl-benzoyl)-methyl-amino]-pyrrolidine-1-carbonyl}-piperidine-1-carboxylic acid tert-butyl ester instead of 4-{(3SR,4RS)-3-(4-chloro-phenyl)-4-[(4-methoxy-3-trifluoromethyl-benzoyl)-methyl-amino]-pyrrolidine-1-carbonyl}-piperidine-1-carboxylic acid tert-butyl ester and was obtained as a light brown oil. MS m/e: 558.0 [M]$^+$.

EXAMPLE 134

N-[(3RS,4SR)-4-(3,4-Dichloro-phenyl)-1-(4-morpholin-4-yl-benzoyl)-pyrrolidin-3-yl]-2-(4-fluoro-phenyl)-N-methyl-acetamide

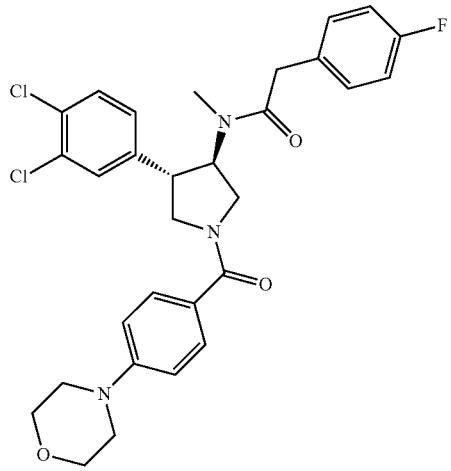 [SMILES: CN(C(=O)Cc1ccc(F)cc1)[C@H]1CN(C(=O)c2ccc(N3CCOCC3)cc2)C[C@@H]1c1ccc(Cl)c(Cl)c1]

In analogy to the procedure described for the synthesis of example 87 (step c), the title compound N-[(3RS,4SR)-4-(3,4-dichloro-phenyl)-1-(4-morpholin-4-yl-benzoyl)-pyrrolidin-3-yl]-2-(4-fluoro-phenyl)-N-methyl-acetamide was prepared from N-[(3RS,4SR)-4-(3,4-dichloro-phenyl)-pyrrolidin-3-yl]-2-(4-fluoro-phenyl)-N-methyl-acetamide using 4-morpholinobenzoic acid instead of 1-(1-methyl-cyclopropanecarbonyl)-piperidine-4-carboxylic acid and was obtained as a light yellow oil. MS m/e: 570.1 [M]$^+$.

EXAMPLE 135

N-[(3RS,4SR)-4-(3,4-Dichloro-phenyl)-1-(6-morpholin-4-yl-pyridine-3-carbonyl)-pyrrolidin-3-yl]-2-(4-fluoro-phenyl)-N-methyl-acetamide

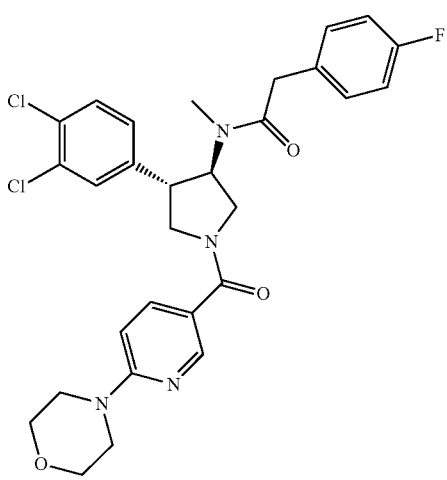 [SMILES: CN(C(=O)Cc1ccc(F)cc1)[C@H]1CN(C(=O)c2ccc(N3CCOCC3)nc2)C[C@@H]1c1ccc(Cl)c(Cl)c1]

In analogy to the procedure described for the synthesis of example 87 (step c), the title compound N-[(3RS,4SR)-4-(3,4-dichloro-phenyl)-1-(6-morpholin-4-yl-pyridine-3-carbonyl)-pyrrolidin-3-yl]-2-(4-fluoro-phenyl)-N-methyl-acetamide was prepared from N-[(3RS,4SR)-4-(3,4-dichloro-phenyl)-pyrrolidin-3-yl]-2-(4-fluoro-phenyl)-N-methyl-acetamide using 6-morpholinonicotinic acid instead of 1-(1-methyl-cyclopropanecarbonyl)-piperidine-4-carboxylic acid and was obtained as a light yellow oil. MS m/e: 571.1 [M]+.

EXAMPLE 136

N-[(3RS,4SR)-4-(3,4-Dichloro-phenyl)-1-(6-methyl-pyridazine-4-carbonyl)-pyrrolidin-3-yl]-2-(4-fluoro-phenyl)-N-methyl-acetamide

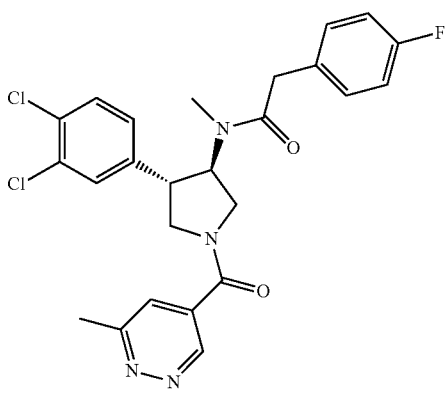 [SMILES: Cc1cc(C(=O)N2C[C@H](c3ccc(Cl)c(Cl)c3)[C@@H](N(C)C(=O)Cc3ccc(F)cc3)C2)cnn1]

In analogy to the procedure described for the synthesis of example 87 (step c), the title compound N-[(3RS,4SR)-4-(3,4-dichloro-phenyl)-1-(6-methyl-pyridazine-4-carbonyl)-pyrrolidin-3-yl]-2-(4-fluoro-phenyl)-N-methyl-acetamide was prepared from N-[(3RS,4SR)-4-(3,4-dichloro-phenyl)-pyrrolidin-3-yl]-2-(4-fluoro-phenyl)-N-methyl-acetamide using 6-methyl-pyridazine-4-carboxylic acid instead of 1-(1-methyl-cyclopropanecarbonyl)-piperidine-4-carboxylic acid and was obtained as a light yellow oil. MS m/e: 501.1 [M]+.

EXAMPLE 137

N-[(3RS,4SR)-4-(3,4-Dichloro-phenyl)-1-(6-morpholin-4-yl-pyridazine-3-carbonyl)-pyrrolidin-3-yl]-2-(4-fluoro-phenyl)-N-methyl-acetamide

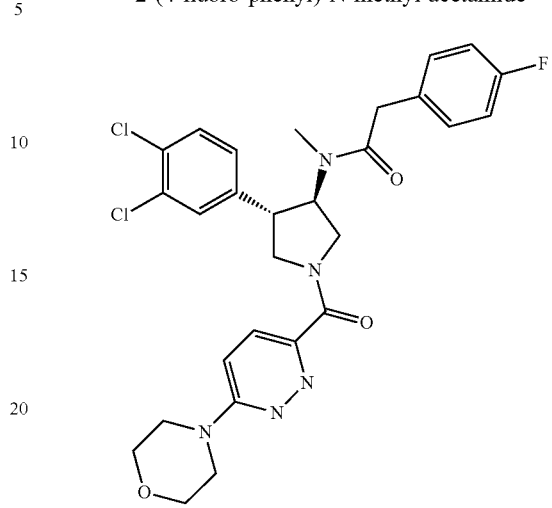

In analogy to the procedure described for the synthesis of example 87 (step c), the title compound N-[(3RS,4SR)-4-(3,4-dichloro-phenyl)-1-(6-morpholin-4-yl-pyridazine-3-carbonyl)-pyrrolidin-3-yl]-2-(4-fluoro-phenyl)-N-methyl-acetamide was prepared from N-[(3RS,4SR)-4-(3,4-dichloro-phenyl)-pyrrolidin-3-yl]-2-(4-fluoro-phenyl)-N-methyl-acetamide using 6-morpholin-4-yl-pyridazine-3-carboxylic acid instead of 1-(1-methyl-cyclopropanecarbonyl)-piperidine-4-carboxylic acid and was obtained as a light yellow oil. MS m/e: 572.2 [M]+.

EXAMPLE 138

N-[(3RS,4SR)-1-(1-Cyclopropylmethyl-piperidine-4-carbonyl)-4-(3,4-dichloro-phenyl)-pyrrolidin-3-yl]-4-methoxy-N-methyl-3-trifluoromethyl-benzamide

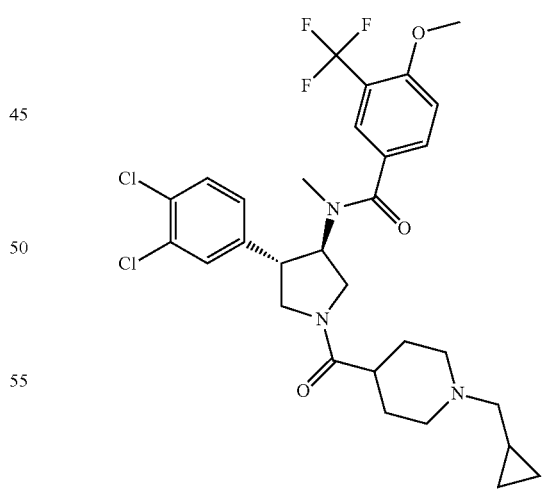

In analogy to the procedure described for the synthesis of example 105, the title compound N-[(3RS,4SR)-1-(1-cyclopropylmethyl-piperidine-4-carbonyl)-4-(3,4-dichloro-phenyl)-pyrrolidin-3-yl]-4-methoxy-N-methyl-3-trifluoromethyl-benzamide was prepared from N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide instead of N-[(3RS,4SR)-4-(4-chloro-phenyl)-1-(piperidine- 4-carbonyl)-pyrrolidin-3-yl]-4-methoxy-N-methyl-3-trifluoromethyl-benzamide and was obtained as a light brown oil. MS m/e: 612.2 [M]+.

EXAMPLE 139

N-{(3RS,4SR)-4-(3,4-Dichloro-phenyl)-1-[1-(3,3,3-trifluoro-propyl)-piperidine-4-carbonyl]-pyrrolidin-3-yl}-4-methoxy-N-methyl-3-trifluoromethyl-benzamide

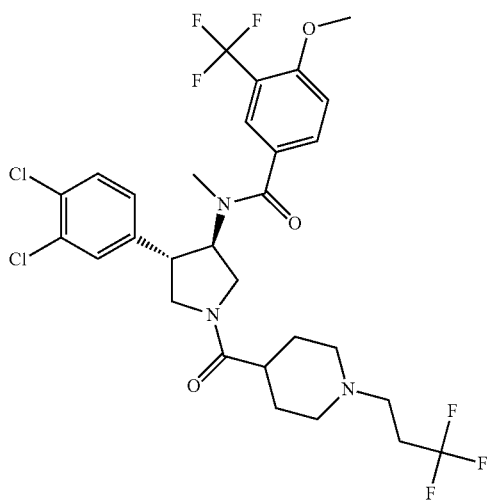 [SMILES: COc1ccc(C(=O)N(C)[C@H]2CN(C(=O)C3CCN(CCC(F)(F)F)CC3)C[C@@H]2c2ccc(Cl)c(Cl)c2)cc1C(F)(F)F]

In analogy to the procedure described for the synthesis of example 105, the title compound N-{(3RS,4SR)-4-(3,4-dichloro-phenyl)-1-[1-(3,3,3-trifluoro-propyl)-piperidine-4-carbonyl]-pyrrolidin-3-yl}-4-methoxy-N-methyl-3-trifluoromethyl-benzamide was prepared from N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide instead of N-[(3RS,4SR)-4-(4-chloro-phenyl)-1-(piperidine-4-carbonyl)-pyrrolidin-3-yl]-4-methoxy-N-methyl-3-trifluoromethyl-benzamide and was obtained as a light brown oil. MS m/e: 645.2 [M]+.

EXAMPLE 140

N-[(3RS,4SR)-4-(3,4-Dichloro-phenyl)-1-(1-ethanesulfonyl-piperidine-4-carbonyl)-pyrrolidin-3-yl]-4-methoxy-N-methyl-3-trifluoromethyl-benzamide

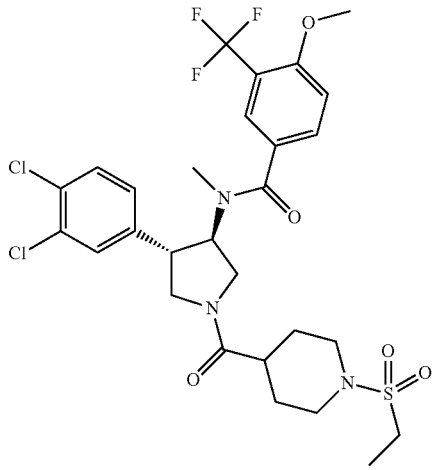 [SMILES: CCS(=O)(=O)N1CCC(C(=O)N2C[C@H](c3ccc(Cl)c(Cl)c3)[C@@H](N(C)C(=O)c3ccc(OC)c(C(F)(F)F)c3)C2)CC1]

To a solution of N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide (50 mg, 0.90 mmol) in acetone (0.5 mL) was added potassium carbonate (finely milled) (19 mg, 0.13 mmol), ethanesulfonyl chloride (13 μL, 0.13 mmol) and acetone (0.5 mL). The suspension was stirred for 18 h at ambient temperature. It was diluted with ethyl acetatec (10 mL) and washed with an aqueous solution of Na2CO3 (1 M, 10 mL) and brine (10 mL). The aqueous layers were extracted with ethyl acetate (10 mL) and the combined organic layers were dried over sodium sulfate. Purification by chromatography (SiO2, heptane:ethyl acetate=30:70 to 0:100) afforded the title compound (44 mg, 76%) as an off-white foam. MS m/e: 650.2 [M]+.

EXAMPLE 141

N-[(3RS,4SR)-1-(1-Cyclopropanesulfonyl-piperidine-4-carbonyl)-4-(3,4-dichloro-phenyl)-pyrrolidin-3-yl]-4-methoxy-N-methyl-3-trifluoromethyl-benzamide

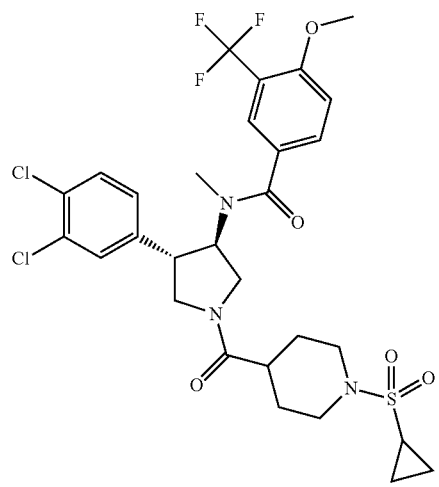 [SMILES: COc1ccc(C(=O)N(C)[C@H]2CN(C(=O)C3CCN(S(=O)(=O)C4CC4)CC3)C[C@@H]2c2ccc(Cl)c(Cl)c2)cc1C(F)(F)F]

In analogy to the procedure described for the synthesis of example 140, the title compound N-[(3RS,4SR)-1-(1-Cyclopropanesulfonyl-piperidine-4-carbonyl)-4-(3,4-dichloro-phenyl)-pyrrolidin-3-yl]-4-methoxy-N-methyl-3-trifluoromethyl-benzamide was prepared from N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide using cyclopropanesulfonylchloride instead of ethanesulfonyl chloride and was obtained as a off-white foam. MS m/e: 662.2 [M]+.

EXAMPLE 142

N-[(3RS,4SR)-1-[1-(2-Cyano-ethyl)-piperidine-4-carbonyl]-4-(3,4-dichloro-phenyl)-pyrrolidin-3-yl]-4-methoxy-N-methyl-3-trifluoromethyl-benzamide

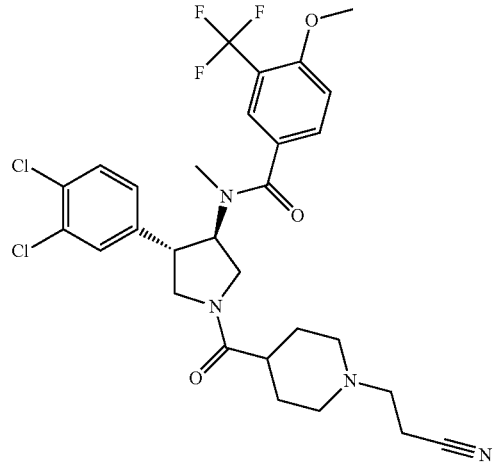 [SMILES: COc1ccc(C(=O)N(C)[C@H]2CN(C(=O)C3CCN(CCC#N)CC3)C[C@@H]2c2ccc(Cl)c(Cl)c2)cc1C(F)(F)F]

To a solution of N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide (50 mg, 0.090 mmol) in dichloromethane (1 mL) was added 3-bromopropionitrile (11 µL, 0.13 mmol) and an aqueous saturated solution of sodium carbonate (1000 µL). The resulting suspension was stirred for 18 h at ambient temperature. After the addition of dichloromethane (1 mL) and further 3-bromopropionitrile (11 µL, 0.13 mmol) it was stirred for 6 h at 40° C. After diluting with ethyl acetate (10 mL) the mixture was washed with an aqueous solution of sodium carbonate (10 mL) and water (10 mL). The aqueous layer was extracted with ethyl acetate (10 mL) and the combined organic layers were dried over sodium sulfate. Purification by chromatography (SiO$_2$, heptane:ethyl acetate:(ethyl acetate:triethylamine=95:5):methanol=20:80:0:0 to 0:0:90:10) afforded the title compound (51 mg, 93%) as an light brown foam. MS m/e: 611.2 [M]$^+$.

EXAMPLE 143

N-[(3RS,4RS)-1-(1-Cyclopropylmethyl-piperidine-4-carbonyl)-4-(3,4-dichloro-phenyl)-pyrrolidin-3-yl]-2-(4-fluoro-phenyl)-N-methyl-acetamide

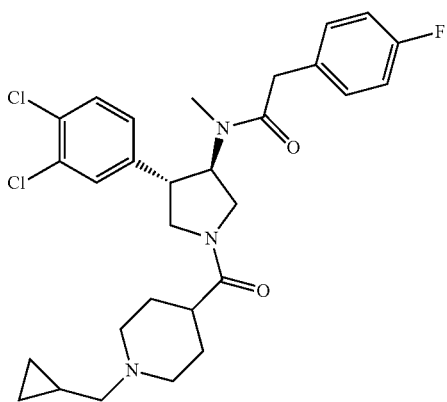 [SMILES: CN(C(=O)Cc1ccc(F)cc1)[C@H]1CN(C(=O)C2CCN(CC3CC3)CC2)C[C@@H]1c1ccc(Cl)c(Cl)c1]

In analogy to the procedure described for the synthesis of example 87 (step c), the title compound N-[(3RS,4RS)-1-(1-cyclopropylmethyl-piperidine-4-carbonyl)-4-(3,4-dichloro-phenyl)-pyrrolidin-3-yl]-2-(4-fluoro-phenyl)-N-methyl-acetamide was prepared from N-[(3RS,4SR)-4-(3,4-dichloro-phenyl)-pyrrolidin-3-yl]-2-(4-fluoro-phenyl)-N-methyl-acetamide using 1-cyclopropylmethyl-piperidine-4-carboxylic acid instead of 1-(1-methyl-cyclopropanecarbonyl)-piperidine-4-carboxylic acid and was obtained as a colorless oil. MS m/e: 546.3 [M]$^+$.

EXAMPLE 144

N-{(3RS,4SR)-4-(3,4-Dichloro-phenyl)-1-[1-(2-methoxy-ethyl)-piperidine-4-carbonyl]-pyrrolidin-3-yl}-4-methoxy-N-methyl-3-trifluoromethyl-benzamide

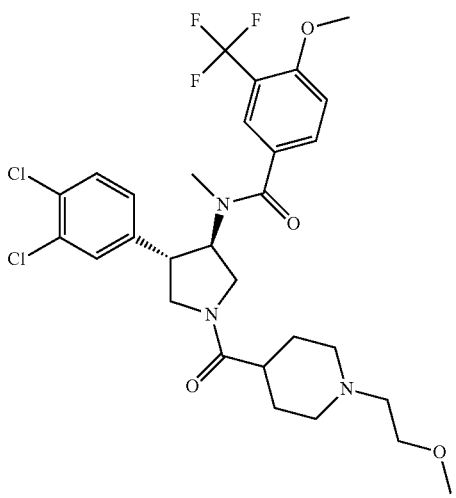 [SMILES: COCCN1CCC(C(=O)N2C[C@H](c3ccc(Cl)c(Cl)c3)[C@@H](N(C)C(=O)c3ccc(OC)c(C(F)(F)F)c3)C2)CC1]

In analogy to the procedure described for the synthesis of example 104, the title compound N-{(3RS,4SR)-4-(3,4-dichloro-phenyl)-1-[1-(2-methoxy-ethyl)-piperidine-4-carbonyl]-pyrrolidin-3-yl}-4-methoxy-N-methyl-3-trifluoromethyl-benzamide was prepared from N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide instead of N-[(3RS,4SR)-4-(4-chloro-phenyl)-1-(piperidine-4-carbonyl)-pyrrolidin-3-yl]-4-methoxy-N-methyl-3-trifluoromethyl-benzamide using methoxyacetaldehyde instead of acetone and was obtained as a colorless oil. MS m/e: 616.4 [M]$^+$.

EXAMPLE 145

4-{(3SR,4RS)-3-(3,4-Dichloro-phenyl)-4-[(4-methoxy-3-trifluoromethyl-benzoyl)-methyl-amino]-pyrrolidine-1-carbonyl}-piperidine-1-carboxylic acid ethyl ester

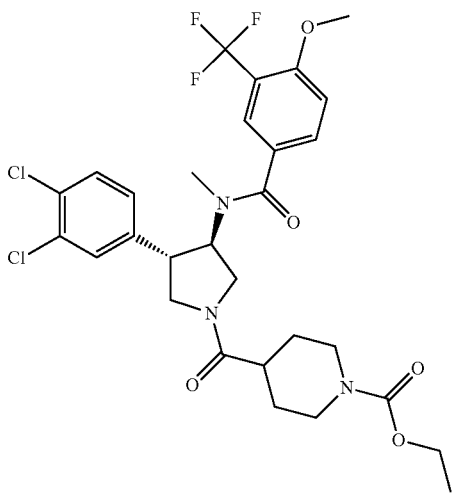 [SMILES: CCOC(=O)N1CCC(C(=O)N2C[C@H](c3ccc(Cl)c(Cl)c3)[C@@H](N(C)C(=O)c3ccc(OC)c(C(F)(F)F)c3)C2)CC1]

In analogy to the procedure described for the synthesis of example 88, the title compound 4-{(3SR,4RS)-3-(3,4- dichloro-phenyl)-4-[(4-methoxy-3-trifluoromethyl-benzoyl)-methyl-amino]-pyrrolidine-1-carbonyl}-piperidine-1-carboxylic acid ethyl ester was prepared from N-[(3RS,4SR)-4-(3,4-Dichloro-phenyl)-1-(piperidine-4-carbonyl)-pyrrolidin-3-yl]-4-methoxy-N-methyl-3-trifluoromethyl-benzamide instead of N-[(3RS,4SR)-4-(4-chloro-phenyl)-pyrrolidin-3-yl]-4-methoxy-N-methyl-3-trifluoromethyl-benzamide using ethyl chloroformate instead of 4-fluorobenzoyl chloride and was obtained as a light brown foam. MS m/e: 630.3 [M]+.

EXAMPLE 146

N-{(3RS,4SR)-4-(3,4-Dichloro-phenyl)-1-[4-(3-methyl-[1,2,4]oxadiazol-5-yl)-benzoyl]-pyrrolidin-3-yl}-2-(4-fluoro-phenyl)-N-methyl-acetamide

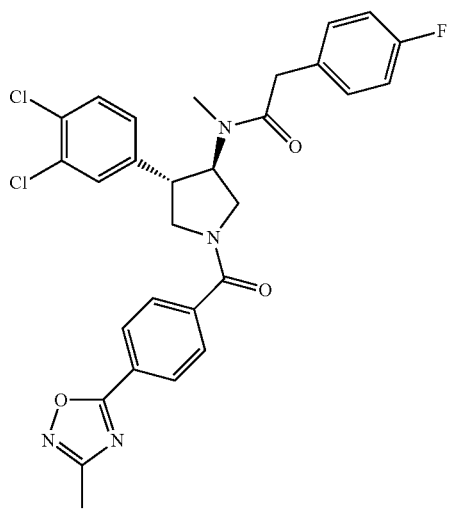 [SMILES: Cc1noc(-c2ccc(C(=O)N3C[C@H](c4ccc(Cl)c(Cl)c4)[C@@H](N(C)C(=O)Cc4ccc(F)cc4)C3)cc2)n1]

In analogy to the procedure described for the synthesis of example 87 (step c), the title compound N-{(3RS,4SR)-4-(3,4-dichloro-phenyl)-1-[4-(3-methyl-[1,2,4]oxadiazol-5-yl)-benzoyl]-pyrrolidin-3-yl}-2-(4-fluoro-phenyl)-N-methyl-acetamide was prepared from N-[(3RS,4SR)-4-(3,4-dichloro-phenyl)-pyrrolidin-3-yl]-2-(4-fluoro-phenyl)-N-methyl-acetamide using 4-(3-methyl-1,2,4-oxadiazol-5-yl)-benzoic acid instead of 1-(1-methyl-cyclopropanecarbonyl)-piperidine-4-carboxylic acid and was obtained as a light yellow oil. MS m/e: 567.1 [M]+.

EXAMPLE 147

N-{(3RS,4SR)-4-(3,4-Dichloro-phenyl)-1-[4-(3-methyl-[1,2,4]oxadiazol-5-yl)-benzoyl]-pyrrolidin-3-yl}-4-methoxy-N-methyl-3-trifluoromethyl-benzamide

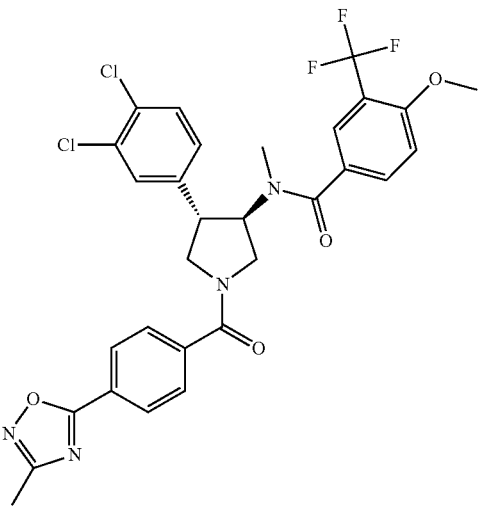 [SMILES: COc1ccc(C(=O)N(C)[C@H]2CN(C(=O)c3ccc(-c4nc(C)no4)cc3)C[C@@H]2c2ccc(Cl)c(Cl)c2)cc1C(F)(F)F]

In analogy to the procedure described for the synthesis of example 87 (step c), the title compound N-{(3RS,4SR)-4-(3,4-dichloro-phenyl)-1-[4-(3-methyl-[1,2,4]oxadiazol-5-yl)-benzoyl]-pyrrolidin-3-yl}-4-methoxy-N-methyl-3-trifluoromethyl-benzamide was prepared from N-[(3RS,4SR)-4-(3,4-dichloro-phenyl)-pyrrolidin-3-yl]-4-methoxy-N-methyl-3-trifluoromethyl-benzamide using 4-(3-methyl-1,2,4-oxadiazol-5-yl)-benzoic acid instead of 1-(1-methyl-cyclopropanecarbonyl)-piperidine-4-carboxylic acid and was obtained as a light yellow oil. MS m/e: 633.1 [M]+.

EXAMPLE 148

N-{(3RS,4SR)-4-(3,4-Dichloro-phenyl)-1-[1-(2-fluoro-allyl)-piperidine-4-carbonyl]-pyrrolidin-3-yl}-4-methoxy-N-methyl-3-trifluoromethyl-benzamide

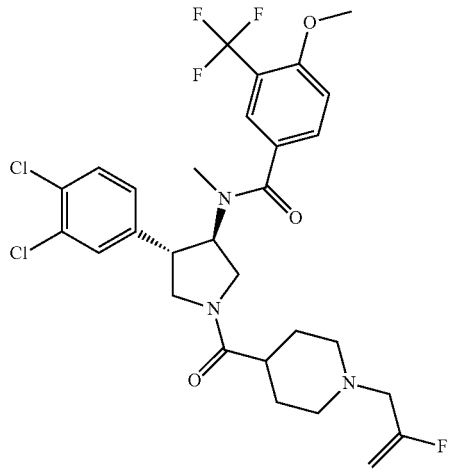 [SMILES: C=C(F)CN1CCC(C(=O)N2C[C@H](c3ccc(Cl)c(Cl)c3)[C@@H](N(C)C(=O)c3ccc(OC)c(C(F)(F)F)c3)C2)CC1]

To a solution of N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide (50 mg, 0.090 mmol) in THF (1 mL) was added under an atmosphere of nitrogen potassium bis(trimethylsilyl)amide (0.885 M in THF, 132 µL, 0.116 mmol). After stirring for 15 min at ambient temperature 3-chloro-2-fluoroprop-1-ene (13 mg, 0.13 mmol) was added and the reaction mixture was stirred for 20 h at this temperature. It was diluted with ethyl acetate (10 mL) and washed with an aqueous solution of sodium carbonate (1 M, 10 mL) and brine (10 mL). The aqueous layers were extracted with ethyl acetate (10 mL) and the combined organic layers dried over sodium sulfate. Purification by chromatography (SiO₂, ethyl acetate:(ethyl acetate:triethylamine=95:5):methanol=100:0:0 to 0:90:10) afforded the title compound (26 mg, 47%) as a light brown foam. MS m/e: 616.4 [M]⁺.

EXAMPLE 149

2-(4-Cyano-phenyl)-N-[(3RS,4SR)-1-(1-cyclopropylmethyl-piperidine-4-carbonyl)-4-(3,4-dichloro-phenyl)-pyrrolidin-3-yl]-N-methyl-acetamide

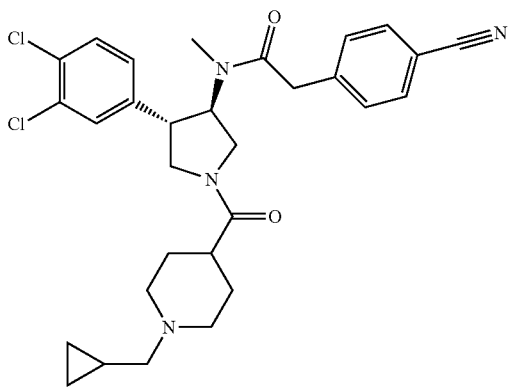 [SMILES: CN(C(=O)Cc1ccc(C#N)cc1)[C@H]1CN(C(=O)C2CCN(CC3CC3)CC2)C[C@@H]1c1ccc(Cl)c(Cl)c1]

a) [(3RS,4SR)-1-(1-Cyclopropylmethyl-piperidine-4-carbonyl)-4-(3,4-dichloro-phenyl)-pyrrolidin-3-yl]-methyl-carbamic acid tert-butyl ester

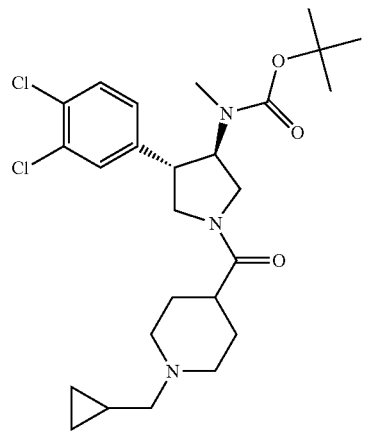 [SMILES: CN(C(=O)OC(C)(C)C)[C@H]1CN(C(=O)C2CCN(CC3CC3)CC2)C[C@@H]1c1ccc(Cl)c(Cl)c1]

In analogy to the procedure described for the synthesis of example 87 (step c), the title compound [(3RS,4SR)-1-(1-cyclopropylmethyl-piperidine-4-carbonyl)-4-(3,4-dichloro-phenyl)-pyrrolidin-3-yl]-methyl-carbamic acid tert-butyl ester was prepared from [(3RS,4SR)-4-(3,4-dichloro-phenyl)-pyrrolidin-3-yl]-methyl-carbamic acid tert-butyl ester instead of N-[(3RS,4SR)-4-(4-chloro-phenyl)-pyrrolidin-3-yl]-4-methoxy-N-methyl-3-trifluoromethyl-benzamide using 1-cyclopropylmethyl-piperidine-4-carboxylic acid instead of 1-(1-methyl-cyclopropanecarbonyl)-piperidine-4-carboxylic acid and was obtained as a dark brown oil, which was directly used without further characterisation.

b) (1-Cyclopropylmethyl-piperidin-4-yl)-[(3SR,4RS)-3-(3,4-dichloro-phenyl)-4-methylamino-pyrrolidin-1-yl]-methanone

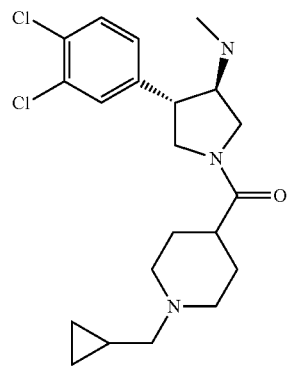 [SMILES: CN[C@H]1CN(C(=O)C2CCN(CC3CC3)CC2)C[C@@H]1c1ccc(Cl)c(Cl)c1]

In analogy to the procedure described for the synthesis of example 96 (step d), the title compound (1-Cyclopropylmethyl-piperidin-4-yl)-[(3SR,4RS)-3-(3,4-dichloro-phenyl)-4-methylamino-pyrrolidin-1-yl]-methanone was prepared from [(3RS,4SR)-1-(1-cyclopropylmethyl-piperidine-4-carbonyl)-4-(3,4-dichloro-phenyl)-pyrrolidin-3-yl]-methyl-carbamic acid tert-butyl ester instead of {(3RS,4SR)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester and was obtained as a brown oil. MS m/e: 410.2 [M]⁺.

c) 2-(4-Cyano-phenyl)-N-[(3RS,4SR)-1-(1-cyclopropylmethyl-piperidine-4-carbonyl)-4-(3,4-dichloro-phenyl)-pyrrolidin-3-yl]-N-methyl-acetamide In analogy to the procedure described for the synthesis of example 87 (step c), the title compound 2-(4-Cyano-phenyl)-N-[(3RS,4SR)-1-(1-cyclopropylmethyl-piperidine-4-carbonyl)-4-(3,4-dichloro-phenyl)-pyrrolidin-3-yl]-N-methyl-acetamide was prepared from (1-cyclopropylmethyl-piperidin-4-yl)-[(3SR,4RS)-3-(3,4-dichloro-phenyl)-4-methylamino-pyrrolidin-1-yl]-methanone instead of N-[(3RS,4SR)-4-(4-chloro-phenyl)-pyrrolidin-3-yl]-4-methoxy-N-methyl-3-trifluoromethyl-benzamide using 4-cyanophenylacetic acid instead of 1-(1-methyl-cyclopropanecarbonyl)-piperidine-4-carboxylic acid and was obtained as a yellow oil. MS m/e: 553.2 [M]⁺.

EXAMPLE 150

N-[(3RS,4SR)-1-(1-Cyclopropylmethyl-piperidine-4-carbonyl)-4-(3,4-dichloro-phenyl)-pyrrolidin-3-yl]-2-(3,4-difluoro-phenyl)-N-methyl-acetamide

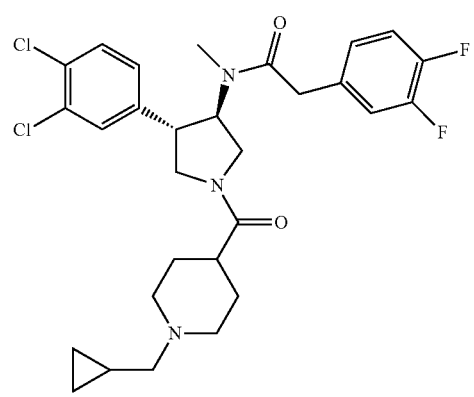 [SMILES: CN(C(=O)Cc1ccc(F)c(F)c1)[C@H]1CN(C(=O)C2CCN(CC3CC3)CC2)C[C@@H]1c1ccc(Cl)c(Cl)c1]

In analogy to the procedure described for the synthesis of example 87 (step c), the title compound N-[(3RS,4SR)-1-(1- cyclopropylmethyl-piperidine-4-carbonyl)-4-(3,4-dichloro-phenyl)-pyrrolidin-3-yl]-2-(3,4-difluoro-phenyl)-N-methyl-acetamide was prepared from (1-cyclopropylmethyl-piperidin-4-yl)-[(3SR,4RS)-3-(3,4-dichloro-phenyl)-4-methylamino-pyrrolidin-1-yl]-methanone instead of N-[(3RS,4SR)-4-(4-chloro-phenyl)-pyrrolidin-3-yl]-4-methoxy-N-methyl-3-trifluoromethyl-benzamide using 3,4-difluorophenylacetic acid instead of 1-(1-methyl-cyclopropanecarbonyl)-piperidine-4-carboxylic acid and was obtained as a light yellow oil. MS m/e: 564.3 [M]$^+$.

EXAMPLE 151

2-Cyclopentyl-N-[(3RS,4SR)-1-(1-cyclopropylm-ethyl-piperidine-4-carbonyl)-4-(3,4-dichloro-phe-nyl)-pyrrolidin-3-yl]-N-methyl-acetamide

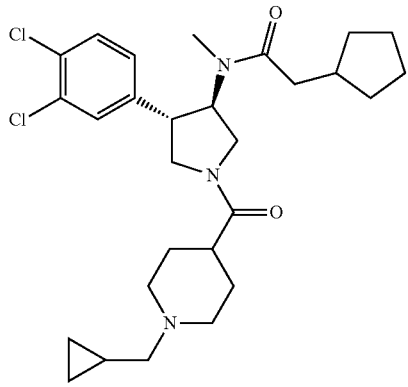 [SMILES: CN(C(=O)CC1CCCC1)[C@H]1CN(C(=O)C2CCN(CC3CC3)CC2)C[C@@H]1c1ccc(Cl)c(Cl)c1]

In analogy to the procedure described for the synthesis of example 88, the title compound 2-cyclopentyl-N-[(3RS,4SR)-1-(1-cyclopropylmethyl-piperidine-4-carbonyl)-4-(3,4-dichloro-phenyl)-pyrrolidin-3-yl]-N-methyl-acetamide was prepared from (1-cyclopropylmethyl-piperidin-4-yl)-[(3SR,4RS)-3-(3,4-dichloro-phenyl)-4-methylamino-pyrrolidin-1-yl]-methanone instead of N-[(3RS,4SR)-4-(4-chloro-phenyl)-pyrrolidin-3-yl]-4-methoxy-N-methyl-3-trifluoromethyl-benzamide using cyclopentylacetyl chloride instead of 4-fluorobenzoyl chloride and was obtained as a light yellow oil. MS m/e: 520.3 [M+H]$^+$.

EXAMPLE 152

N-[(3RS,4SR)-1-(1-Cyclopropylmethyl-piperidine-4-carbonyl)-4-(3,4-dichloro-phenyl)-pyrrolidin-3-yl]-2-(2,3-difluoro-phenyl)-N-methyl-acetamide

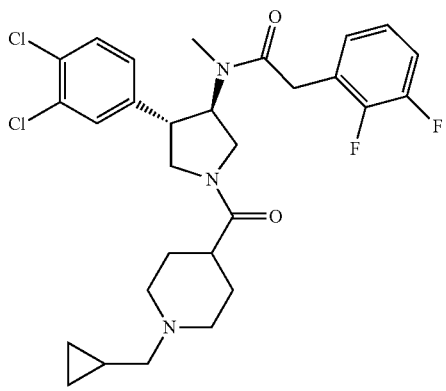 [SMILES: CN(C(=O)Cc1cccc(F)c1F)[C@H]1CN(C(=O)C2CCN(CC3CC3)CC2)C[C@@H]1c1ccc(Cl)c(Cl)c1]

In analogy to the procedure described for the synthesis of example 87 (step c), the title compound N-[(3RS,4SR)-1-(1-cyclopropylmethyl-piperidine-4-carbonyl)-4-(3,4-dichloro-phenyl)-pyrrolidin-3-yl]-2-(2,3-difluoro-phenyl)-N-methyl-acetamide was prepared from (1-cyclopropylmethyl-piperidin-4-yl)-[(3SR,4RS)-3-(3,4-dichloro-phenyl)-4-methylamino-pyrrolidin-1-yl]-methanone instead of N-[(3RS,4SR)-4-(4-chloro-phenyl)-pyrrolidin-3-yl]-4-methoxy-N-methyl-3-trifluoromethyl-benzamide using 2,3-difluorophenylacetic acid instead of 1-(1-methyl-cyclopropanecarbonyl)-piperidine-4-carboxylic acid and was obtained as a colorless semi-solid. MS m/e: 564.4 [M]$^+$.

EXAMPLE 153

4-Chloro-N-[(3R,4S)-4-(4-chloro-phenyl)-1-(1-cy-clopropylmethyl-piperidine-4-carbonyl)-pyrrolidin-3-yl]-N-methyl-3-trifluoromethyl-benzamide

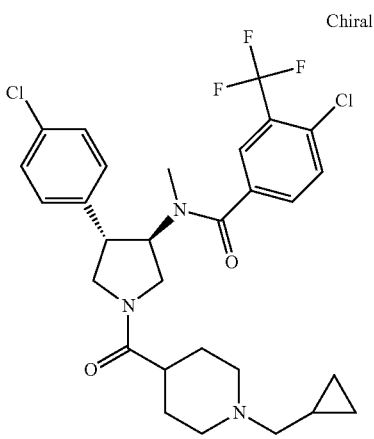 [SMILES: CN(C(=O)c1ccc(Cl)c(C(F)(F)F)c1)[C@H]1CN(C(=O)C2CCN(CC3CC3)CC2)C[C@@H]1c1ccc(Cl)cc1]

and

EXAMPLE 154

4-Chloro-N-[(3S,4R)-4-(4-chloro-phenyl)-1-(1-cy-clopropylmethyl-piperidine-4-carbonyl)-pyrrolidin-3-yl]-N-methyl-3-trifluoromethyl-benzamide

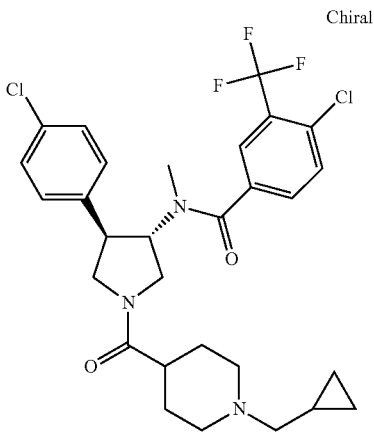 [SMILES: CN(C(=O)c1ccc(Cl)c(C(F)(F)F)c1)[C@@H]1CN(C(=O)C2CCN(CC3CC3)CC2)C[C@H]1c1ccc(Cl)cc1]

4-Chloro-N-[(3RS,4SR)-4-(4-chloro-phenyl)-1-(1-cyclo-propylmethyl-piperidine-4-carbonyl)-pyrrolidin-3-yl]-N-methyl-3-trifluoromethyl-benzamide was subjected to column chromatography on chiral phase to yield 4-chloro-N-[(3R,4S)-4-(4-chloro-phenyl)-1-(1-cyclopropylmethyl-piperidine-4-carbonyl)-pyrrolidin-3-yl]-N-methyl-3-trifluoromethyl-benzamide (MS (m/e): 581.2 [M]$^+$) as a white foam and 4-chloro-N-[(3S,4R)-4-(4-chloro-phenyl)-1-

(1-cyclopropylmethyl-piperidine-4-carbonyl)-pyrrolidin-3-yl]-N-methyl-3-trifluoromethyl-benzamide (MS (m/e): 581.2 [M]+) as an off-white foam.

EXAMPLE 155

4-Chloro-N-{(3R,4S)-4-(4-chloro-phenyl)-1-[1-(1-methyl-cyclopropanecarbonyl)-piperidine-4-carbonyl]-pyrrolidin-3-yl}-N-methyl-3-trifluoromethyl-benzamide

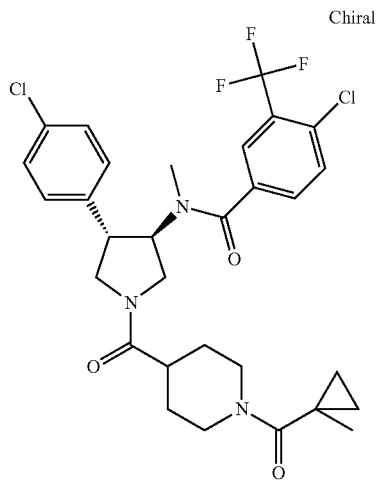 [SMILES: CN(C(=O)c1ccc(Cl)c(C(F)(F)F)c1)[C@H]1CN(C(=O)C2CCN(C(=O)C3(C)CC3)CC2)C[C@@H]1c1ccc(Cl)cc1]

and

EXAMPLE 156

4-Chloro-N-{(3S,4R)-4-(4-chloro-phenyl)-1-[1-(1-methyl-cyclopropanecarbonyl)-piperidine-4-carbonyl]-pyrrolidin-3-yl}-N-methyl-3-trifluoromethyl-benzamide

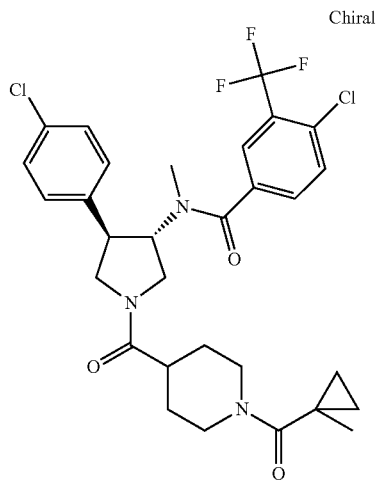 [SMILES: CN(C(=O)c1ccc(Cl)c(C(F)(F)F)c1)[C@@H]1CN(C(=O)C2CCN(C(=O)C3(C)CC3)CC2)C[C@H]1c1ccc(Cl)cc1]

4-Chloro-N-{(3RS,4SR)-4-(4-chloro-phenyl)-1-[1-(1-methyl-cyclopropanecarbonyl)-piperidine-4-carbonyl]-pyrrolidin-3-yl}-N-methyl-3-trifluoromethyl-benzamide was subjected to column chromatography on chiral phase to yield 4-chloro-N-{(3R,4S)-4-(4-chloro-phenyl)-1-[1-(1-methyl-cyclopropanecarbonyl)-piperidine-4-carbonyl]-pyrrolidin-3-yl}-N-methyl-3-trifluoromethyl-benzamide (MS (m/e): 610.2 [M]+) as a white foam and 4-chloro-N-{(3S,4R)-4-(4-chloro-phenyl)-1-[1-(1-methyl-cyclopropanecarbonyl)-piperidine-4-carbonyl]-pyrrolidin-3-yl}-N-methyl-3-trifluoromethyl-benzamide (MS (m/e): 610.2 [M]+) as a white foam.

EXAMPLE 157

4-{(3SR,4RS)-3-(4-Chloro-phenyl)-4-[(4-chloro-3-trifluoromethyl-benzoyl)-methyl-amino]-pyrrolidine-1-carbonyl}-piperidine-1-carboxylic acid tert-butyl ester

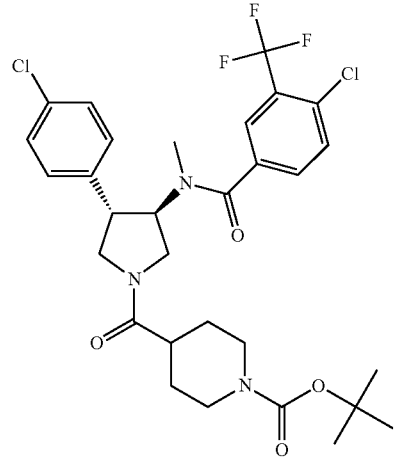 [SMILES: CN(C(=O)c1ccc(Cl)c(C(F)(F)F)c1)[C@H]1CN(C(=O)C2CCN(C(=O)OC(C)(C)C)CC2)C[C@@H]1c1ccc(Cl)cc1]

In analogy to the procedure described for the synthesis of example 97, the title compound 4-{(3SR,4RS)-3-(4-chloro-phenyl)-4-[(4-chloro-3-trifluoromethyl-benzoyl)-methyl-amino]-pyrrolidine-1-carbonyl}-piperidine-1-carboxylic acid tert-butyl ester was prepared from 4-chloro-N-[(3R,4S)-4-(4-chloro-phenyl)-pyrrolidin-3-yl]-N-methyl-3-trifluoromethyl-benzamide instead of {4-[(3SR,4RS)-3-(3,4-dichloro-phenyl)-4-methylamino-pyrrolidine-1-carbonyl]-piperidin-1-yl}-(1-methyl-cyclopropyl)-methanone using piperidine-1,4-dicarboxylic acid mono-tert-butyl ester instead of 4-chloro-3-(trifluoromethyl)benzoic acid and was obtained as a white foam. MS m/e: 528.2 [M-BOC]+.

EXAMPLE 158

2-(4-Chloro-phenyl)-N-[(3RS,4SR)-1-(1-cyclopropylmethyl-piperidine-4-carbonyl)-4-(3,4-dichloro-phenyl)-pyrrolidin-3-yl]-N-methyl-acetamide

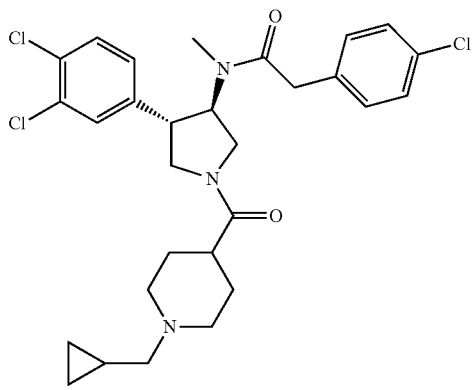 [SMILES: CN(C(=O)Cc1ccc(Cl)cc1)[C@H]1CN(C(=O)C2CCN(CC3CC3)CC2)C[C@@H]1c1ccc(Cl)c(Cl)c1]

In analogy to the procedure described for the synthesis of example 88, the title compound 2-(4-chloro-phenyl)-N-[(3RS,4SR)-1-(1-cyclopropylmethyl-piperidine-4-carbonyl)-4-(3,4-dichloro-phenyl)-pyrrolidin-3-yl]-N-methyl-acetamide was prepared from (1-cyclopropylmethyl-piperidin-4-yl)-[(3SR,4RS)-3-(3,4-dichloro-phenyl)-4-methylamino-pyrrolidin-1-yl]-methanone instead of N-[(3RS,4SR)-4-(4-chloro-phenyl)-pyrrolidin-3-yl]-4-methoxy-N-methyl-3-trifluoromethyl-benzamide using 4-chlorophenylacetyl chloride instead of 4-fluorobenzoyl chloride and was obtained as an off-white semi-solid. MS m/e: 562.2 [M]+.

EXAMPLE 159

N-[(3RS,4SR)-1-(1-Cyclopropylmethyl-piperidine-4-carbonyl)-4-(3,4-dichloro-phenyl)-pyrrolidin-3-yl]-2-(4-fluoro-phenyl)-N-methyl-propionamide

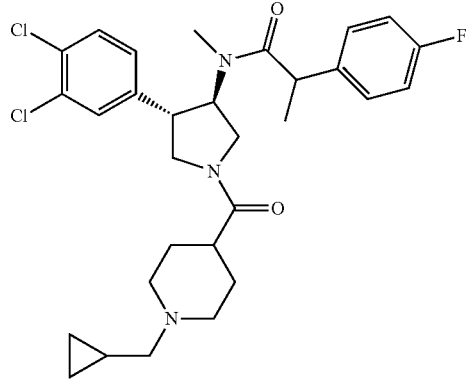 [SMILES: CC(C(=O)N(C)[C@H]1CN(C(=O)C2CCN(CC3CC3)CC2)C[C@@H]1c1ccc(Cl)c(Cl)c1)c1ccc(F)cc1]

In analogy to the procedure described for the synthesis of example 87 (step c), the title compound N-[(3RS,4SR)-1-(1-cyclopropylmethyl-piperidine-4-carbonyl)-4-(3,4-dichloro-phenyl)-pyrrolidin-3-yl]-2-(4-fluoro-phenyl)-N-methyl-propionamide was prepared from (1-cyclopropylmethyl-piperidin-4-yl)-[(3SR,4RS)-3-(3,4-dichloro-phenyl)-4-methylamino-pyrrolidin-1-yl]-methanone instead of N-[(3RS,4SR)-4-(4-chloro-phenyl)-pyrrolidin-3-yl]-4-methoxy-N-methyl-3-trifluoromethyl-benzamide using 4-fluoro-alpha-methylphenyl acetic acid instead of 1-(1-methyl-cyclopropanecarbonyl)-piperidine-4-carboxylic acid and was obtained as a colorless oil. MS m/e: 560.2 [M]+.

EXAMPLE 160

4-Chloro-N-[(3RS,4SR)-4-(4-chloro-phenyl)-1-(piperidine-4-carbonyl)-pyrrolidin-3-yl]-N-methyl-3-trifluoromethyl-benzamide

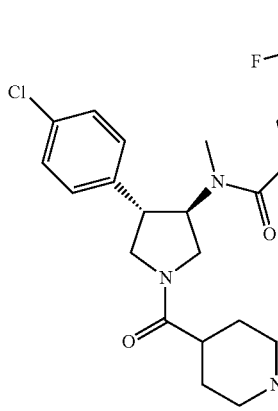

In analogy to the procedure described for the synthesis of example 103, the title compound 4-chloro-N-[(3RS,4SR)-4-(4-chloro-phenyl)-1-(piperidine-4-carbonyl)-pyrrolidin-3-yl]-N-methyl-3-trifluoromethyl-benzamide was prepared from 4-{(3SR,4RS)-3-(4-chloro-phenyl)-4-[(4-chloro-3-trifluoromethyl-benzoyl)-methyl-amino]-pyrrolidine-1-carbonyl}-piperidine-1-carboxylic acid tert-butyl ester instead of 4-{(3SR,4RS)-3-(4-chloro-phenyl)-4-[(4-methoxy-3-trifluoromethyl-benzoyl)-methyl-amino]-pyrrolidine-1-carbonyl}-piperidine-1-carboxylic acid tert-butyl ester and was obtained as a white foam. MS m/e: 528.0 [M]+.

EXAMPLE 161

4-Chloro-N-[(3RS,4SR)-4-(4-chloro-phenyl)-1-(1-cyclopropanesulfonyl-piperidine-4-carbonyl)-pyrrolidin-3-yl]-N-methyl-3-trifluoromethyl-benzamide

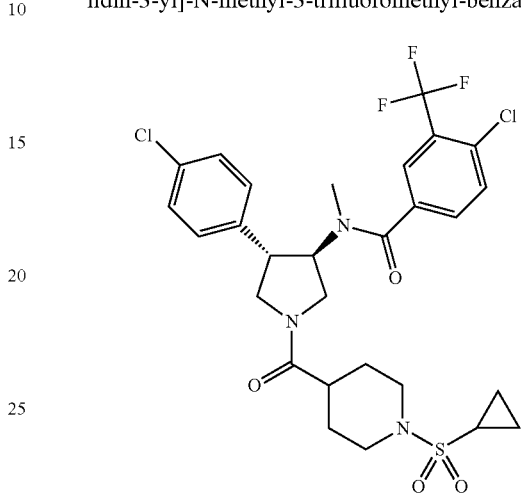

In analogy to the procedure described for the synthesis of example 141, the title compound 4-chloro-N-[(3RS,4SR)-4-(4-chloro-phenyl)-1-(1-cyclopropanesulfonyl-piperidine-4-carbonyl)-pyrrolidin-3-yl]-N-methyl-3-trifluoromethyl-benzamide was prepared from 4-chloro-N-[(3RS,4SR)-4-(4-chloro-phenyl)-1-(piperidine-4-carbonyl)-pyrrolidin-3-yl]-N-methyl-3-trifluoromethyl-benzamide instead of N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide and was obtained as a colorless oil. MS m/e: 632.3 [M]+.

EXAMPLE 162

4-Chloro-N-{(3RS,4SR)-4-(4-chloro-phenyl)-1-[1-(tetrahydro-pyran-4-yl)-piperidine-4-carbonyl]-pyrrolidin-3-yl}-N-methyl-3-trifluoromethyl-benzamide

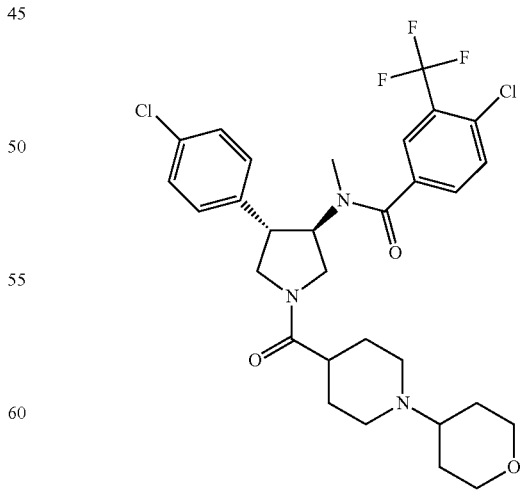

In analogy to the procedure described for the synthesis of example 104, the title compound 4-chloro-N-{(3RS,4SR)-4-(4-chloro-phenyl)-1-[1-(tetrahydro-pyran-4-yl)-piperidine-4-carbonyl]-pyrrolidin-3-yl}-N-methyl-3-trifluoromethylbenzamide was prepared from 4-chloro-N-[(3RS,4SR)-4-(4-chloro-phenyl)-1-(piperidine-4-carbonyl)-pyrrolidin-3-yl]-N-methyl-3-trifluoromethyl-benzamide using tetrahydro-4H-pyran-4-one instead of acetone and was obtained as a white foam. MS m/e: 612.2 [M]⁺.

EXAMPLE 163

4-Chloro-N-[(3RS,4SR)-4-(4-chloro-phenyl)-1-(1-cyanomethyl-piperidine-4-carbonyl)-pyrrolidin-3-yl]-N-methyl-3-trifluoromethyl-benzamide

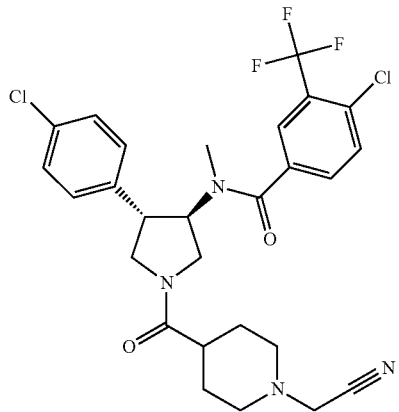 [SMILES: CN(C(=O)c1ccc(Cl)c(C(F)(F)F)c1)[C@H]1CN(C(=O)C2CCN(CC#N)CC2)C[C@@H]1c1ccc(Cl)cc1]

To a solution of 4-chloro-N-[(3RS,4SR)-4-(4-chloro-phenyl)-1-(piperidine-4-carbonyl)-pyrrolidin-3-yl]-N-methyl-3-trifluoromethyl-benzamide (216 mg, 0.382 mmol) in DMF (1 mL) was added sodium hydride (55% dispersion in mineral oil, 6 mg, 0.14 mmol). After stirring for 30 min at ambient temperature iodoacetonitrile (9 μl, 0.12 mmol) was added And the suspension was stirred for 18 h at this temperature. After the addition of further iodoacetonitrile (9 μl, 0.12 mmol) the resulting dark brown solution was stirred for further 5 h at ambient temperature. It was diluted with ethyl acetate (10 mL) and was washed with aqueous sodium carbonate (1 M, 10 mL) and brine (10 mL). The aqueous layers were extracted with ethyl acetate (10 mL) and the combined organic phases were dried over sodium sulfate. Purification by chromatography (SiO₂, (ethyl acetate:triethylamine=95:5):methanol=100:0 to 70:30) afforded the title compound (45 mg, 88%) as a white foam. MS m/e: 567.1 [M]⁺.

EXAMPLE 164

4-Chloro-N-[(3RS,4SR)-1-(1-cyclopropylmethyl-piperidine-4-carbonyl)-4-(3,4-dichloro-phenyl)-pyrrolidin-3-yl]-N-methyl-3-trifluoromethyl-benzamide

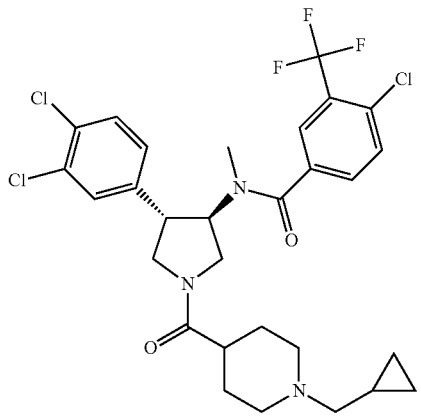 [SMILES: CN(C(=O)c1ccc(Cl)c(C(F)(F)F)c1)[C@H]1CN(C(=O)C2CCN(CC3CC3)CC2)C[C@@H]1c1ccc(Cl)c(Cl)c1]

In analogy to the procedure described for the synthesis of example 87 (step c), the title compound 4-chloro-N-[(3RS,4SR)-1-(1-cyclopropylmethyl-piperidine-4-carbonyl)-4-(3,4-dichloro-phenyl)-pyrrolidin-3-yl]-N-methyl-3-trifluoromethyl-benzamide was prepared from (1-cyclopropylmethyl-piperidin-4-yl)-[(3SR,4RS)-3-(3,4-dichloro-phenyl)-4-methylamino-pyrrolidin-1-yl]-methanone instead of N-[(3RS,4SR)-4-(4-chloro-phenyl)-pyrrolidin-3-yl]-4-methoxy-N-methyl-3-trifluoromethyl-benzamide using 4-chloro-3-(trifluoromethyl)benzoic acid instead of 1-(1-methyl-cyclopropanecarbonyl)-piperidine-4-carboxylic acid and was obtained as a white foam. MS m/e: 616.3 [M]⁺.

EXAMPLE 165

4-Chloro-N-{(3RS,4SR)-4-(4-chloro-phenyl)-1-[1-(2-cyano-ethyl)-piperidine-4-carbonyl]-pyrrolidin-3-yl}-N-methyl-3-trifluoromethyl-benzamide

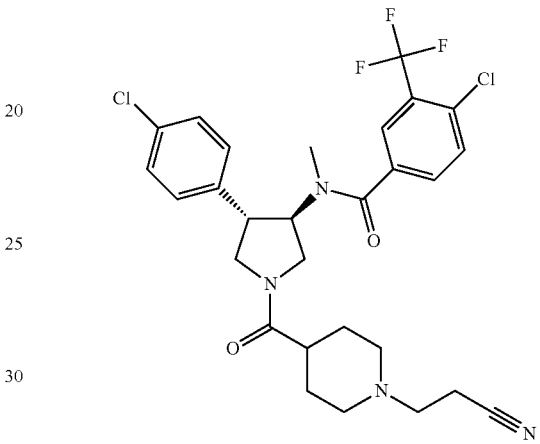

In analogy to the procedure described for the synthesis of example 142, the title compound 4-chloro-N-{(3RS,4SR)-4-(4-chloro-phenyl)-1-[1-(2-cyano-ethyl)-piperidine-4-carbonyl]-pyrrolidin-3-yl}-N-methyl-3-trifluoromethyl-benzamide was prepared from N-[(3RS,4SR)-4-(4-chloro-phenyl)-1-(piperidine-4-carbonyl)-pyrrolidin-3-yl]-4-methoxy-N-methyl-3-trifluoromethyl-benzamide instead of N-[(3RS,4SR)-4-(3,4-dichloro-phenyl)-1-(piperidine-4-carbonyl)-pyrrolidin-3-yl]-4-methoxy-N-methyl-3-trifluoromethyl-benzamide and was obtained as a colorless oil. MS m/e: 581.2 [M]⁺.

EXAMPLE 166

4-Trifluoromethyl-pyridine-2-carboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide

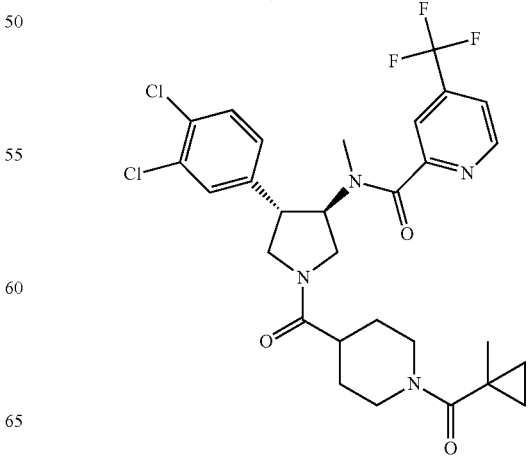

In analogy to the procedure described for the synthesis of example 97, the title compound 4-trifluoromethyl-pyridine-2-carboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 4-(trifluoromethyl)pyridine-2-carboxylic acid instead of 4-chloro-3-(trifluoromethyl)benzoic acid and was obtained as a light brown foam. MS m/e: 611.2 [M]⁺.

EXAMPLE 167

4-Chloro-N-[(3S,4R)-1-(1-cyclopropylmethyl-piperidine-4-carbonyl)-4-(3,4-dichloro-phenyl)-pyrrolidin-3-yl]-N-methyl-3-trifluoromethyl-benzamide

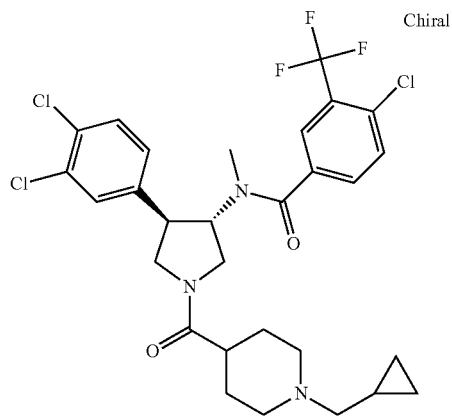 [SMILES: CN(C(=O)c1ccc(Cl)c(C(F)(F)F)c1)[C@@H]1CN(C(=O)C2CCN(CC3CC3)CC2)C[C@H]1c1ccc(Cl)c(Cl)c1]

and

EXAMPLE 168

4-Chloro-N-[(3R,4S)-1-(1-cyclopropylmethyl-piperidine-4-carbonyl)-4-(3,4-dichloro-phenyl)-pyrrolidin-3-yl]-N-methyl-3-trifluoromethyl-benzamide

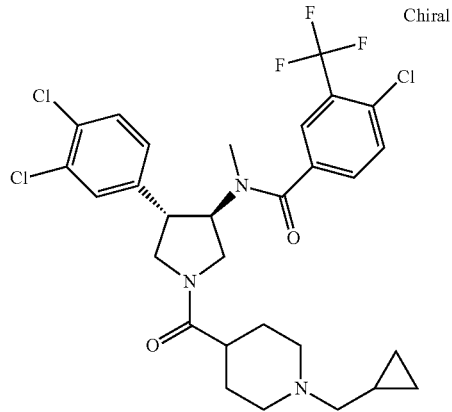 [SMILES: CN(C(=O)c1ccc(Cl)c(C(F)(F)F)c1)[C@H]1CN(C(=O)C2CCN(CC3CC3)CC2)C[C@@H]1c1ccc(Cl)c(Cl)c1]

4-Chloro-N-[(3SR,4RS)-1-(1-cyclopropylmethyl-piperidine-4-carbonyl)-4-(3,4-dichloro-phenyl)-pyrrolidin-3-yl]-N-methyl-3-trifluoromethyl-benzamide was subjected to column chromatography on chiral phase to yield 4-chloro-N-[(3S,4R)-1-(1-cyclopropylmethyl-piperidine-4-carbonyl)-4-(3,4-dichloro-phenyl)-pyrrolidin-3-yl]-N-methyl-3-trifluoromethyl-benzamide (MS (m/e): 616.3 [M]⁺) as a white foam and 4-chloro-N-[(3R,4S)-1-(1-cyclopropylmethyl-piperidine-4-carbonyl)-4-(3,4-dichloro-phenyl)-pyrrolidin-3-yl]-N-methyl-3-trifluoromethyl-benzamide (MS (m/e): 616.3 [M]⁺) as a white foam.

EXAMPLE 169

4-Trifluoromethyl-pyridine-2-carboxylic acid {(3R,4S)-4-(3,4-dichloro-phenyl)-1-[1-(1-methyl-cyclopropanecarbonyl)-piperidine-4-carbonyl]-pyrrolidin-3-yl}-methyl-amide

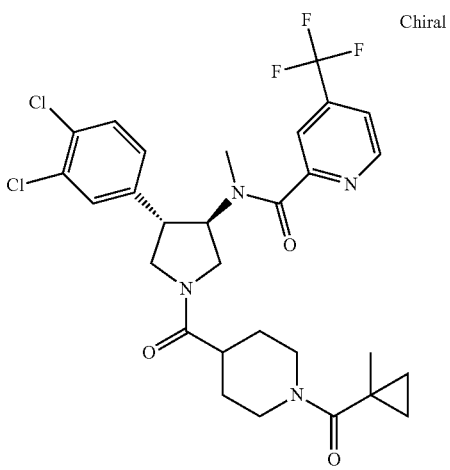 [SMILES: CN(C(=O)c1cc(C(F)(F)F)ccn1)[C@H]1CN(C(=O)C2CCN(C(=O)C3(C)CC3)CC2)C[C@@H]1c1ccc(Cl)c(Cl)c1]

and

EXAMPLE 170

4-Trifluoromethyl-pyridine-2-carboxylic acid {(3S,4R)-4-(3,4-dichloro-phenyl)-1-[1-(1-methyl-cyclopropanecarbonyl)-piperidine-4-carbonyl]-pyrrolidin-3-yl}-methyl-amide

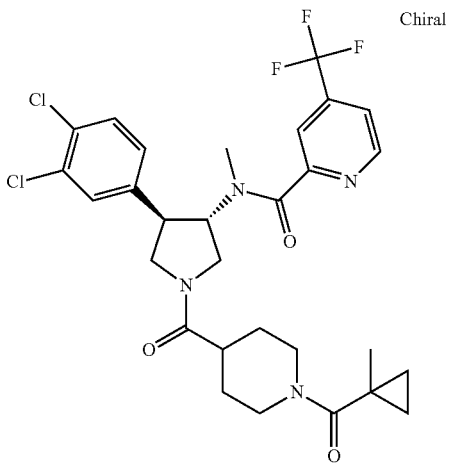 [SMILES: CN(C(=O)c1cc(C(F)(F)F)ccn1)[C@@H]1CN(C(=O)C2CCN(C(=O)C3(C)CC3)CC2)C[C@H]1c1ccc(Cl)c(Cl)c1]

4-Trifluoromethyl-pyridine-2-carboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide was subjected to column chromatography on chiral phase to yield 4-trifluoromethyl-pyridine-2-carboxylic acid {(3R,4S)-4-(3,4-dichloro-phenyl)-1-[1-(1-methyl-cyclopropanecarbonyl)-piperidine-4-carbonyl]-pyrrolidin-3-yl}-methyl-amide (MS (m/e): 611.3 [M]⁺) as an off-white semi-solid and 4-trifluoromethyl-pyridine-2-carboxylic acid {(3S,4R)-4-(3,4-dichloro-phenyl)-1-[1-(1-methyl-cyclopropanecarbonyl)-piperidine-4-carbonyl]-pyrrolidin-3-yl}-methyl-amide (MS (m/e): 611.3 [M]+) as a white semi-solid.

EXAMPLE 171

3-Bromo-4-chloro-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-benzamide

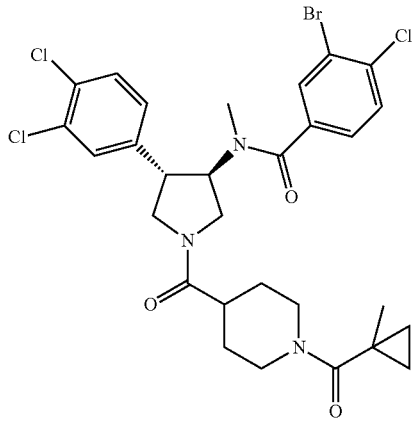 [SMILES: CN(C(=O)c1ccc(Cl)c(Br)c1)[C@H]1CN(C(=O)C2CCN(C(=O)C3(C)CC3)CC2)C[C@@H]1c1ccc(Cl)c(Cl)c1]

In analogy to the procedure described for the synthesis of example 97, the title compound 3-bromo-4-chloro-N-{(3RS, 4SR)-4-(3,4-dichloro-phenyl)-1-[1-(1-methyl-cyclopropanecarbonyl)-piperidine-4-carbonyl]-pyrrolidin-3-yl}-N-methyl-benzamide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using 3-bromo-4-chlorobenzoic acid instead of 4-chloro-3-(trifluoromethyl)benzoic acid and was obtained as a colorless oil. MS m/e: 656.0 [M]+.

EXAMPLE 172

6-Methyl-pyridazine-4-carboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide

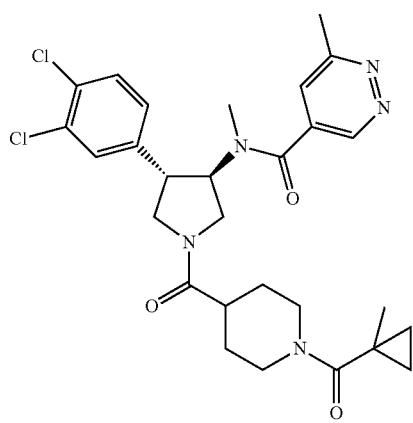 [SMILES: Cc1cc(C(=O)N(C)[C@H]2CN(C(=O)C3CCN(C(=O)C4(C)CC4)CC3)C[C@@H]2c2ccc(Cl)c(Cl)c2)cnn1]

In analogy to the procedure described for the synthesis of example 97, the title compound 6-methyl-pyridazine-4-carboxylic acid {(3RS,4SR)-4-(3,4-dichloro-phenyl)-1-[1-(1-methyl-cyclopropanecarbonyl)-piperidine-4-carbonyl]-pyrrolidin-3-yl}-methyl-amide was prepared from {4-[(3SR, 4RS)-3-(3,4-dichloro-phenyl)-4-methylamino-pyrrolidine-1-carbonyl]-piperidin-1-yl}-(1-methyl-cyclopropyl)-methanone using 6-methyl-pyridazine-4-carboxylic acid instead of 4-chloro-3-(trifluoromethyl)benzoic acid and was obtained as a light brown oil. MS m/e: 557.9 [M]+.

EXAMPLE 173

4-Chloro-3-cyclopropyl-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-benzamide

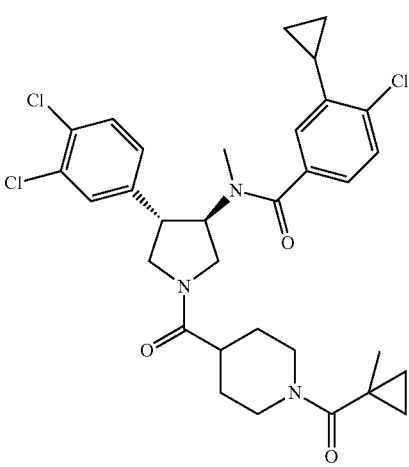 [SMILES: CN(C(=O)c1ccc(Cl)c(C2CC2)c1)[C@H]1CN(C(=O)C2CCN(C(=O)C3(C)CC3)CC2)C[C@@H]1c1ccc(Cl)c(Cl)c1]

To a solution of 3-bromo-4-chloro-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-benzamide (78 mg, 0.12 mmol) in toluene (1 mL) and water (0.048 mL) was added under an atmosphere of nitrogen potassium phosphate, tribasic mono hydrate (88 mg, 0.42 mmol), tricyclohexylphosphine (4 mg, 0.014 mmol) palladium(II) acetate (2 mg, 0.009 mmol). The reaction mixture was stirred for 18 h at 80° C. under an atmosphere of nitrogen. It was concentrated and purification by chromatography (SiO$_2$, ethyl acetate: methanol=100:0 to 85:15) afforded the title compound (71 mg, 97%) as a light brown foam. MS m/e: 616.2 [M]+.

EXAMPLE 174

4-Chloro-N-{(3RS,4SR)-4-(3,4-dichloro-phenyl)-1-[1-(1-methyl-cyclopropanecarbonyl)-piperidine-4-carbonyl]-pyrrolidin-3-yl}-3-ethyl-N-methyl-benzamide

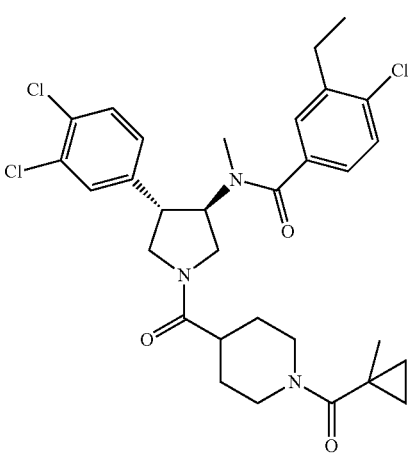 [SMILES: CCc1cc(C(=O)N(C)[C@H]2CN(C(=O)C3CCN(C(=O)C4(C)CC4)CC3)C[C@@H]2c2ccc(Cl)c(Cl)c2)ccc1Cl]

To a solution of 3-bromo-4-chloro-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-benzamide (50 mg; 0.076 mmol) in THF (0.5 mL) was added under an argon atmosphere tetrakis(triphenylphosphine)palladium (0) (5 mg; 0.04 mmol) and diethylzinc (1 M in hexane, 762 µL; 0.762 mmol). The resulting solution was stirred for 5 h at 65° C. before it was diluted with ethyl acetatec (30 mL) and washed with aqueous sodium carbonate (saturated, 20 mL), water (20 mL) and aqueous sodium carbonate. (saturated, 20 mL). The aqueous phases were extracted with ethyl acetate (30 mL) and dried over sodium sulfate. Purification by chromatography (SiO$_2$, ethyl acetate:methanol=100:0 to 90:10) afforded the title compound (37 mg, 47%) as a light brown foam. MS m/e: 604.2 [M]$^+$.

EXAMPLE 175

4-Chloro-3-cyclopropyl-N-{(3R,4S)-4-(3,4-dichloro-phenyl)-1-[1-(1-methyl-cyclopropanecarbonyl)-piperidine-4-carbonyl]-pyrrolidin-3-yl}-N-methyl-benzamide

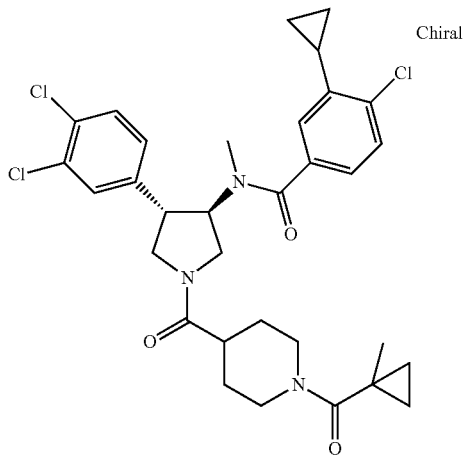 [SMILES: CN(C(=O)c1ccc(Cl)c(C2CC2)c1)[C@H]1CN(C(=O)C2CCN(C(=O)C3(C)CC3)CC2)C[C@@H]1c1ccc(Cl)c(Cl)c1]

and

EXAMPLE 176

4-Chloro-3-cyclopropyl-N-{(3S,4R)-4-(3,4-dichloro-phenyl)-1-[1-(1-methyl-cyclopropanecarbonyl)-piperidine-4-carbonyl]-pyrrolidin-3-yl}-N-methyl-benzamide

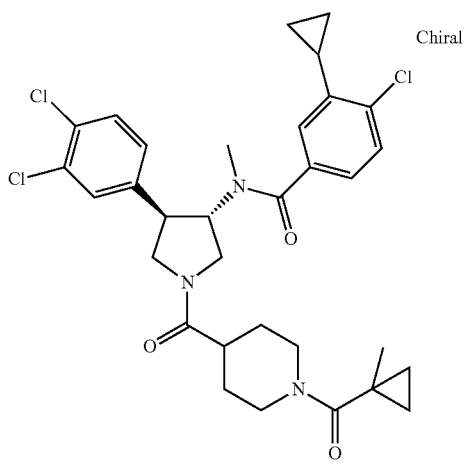 [SMILES: CN(C(=O)c1ccc(Cl)c(C2CC2)c1)[C@@H]1CN(C(=O)C2CCN(C(=O)C3(C)CC3)CC2)C[C@H]1c1ccc(Cl)c(Cl)c1]

4-Chloro-3-cyclopropyl-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-benzamide was subjected to column chromatography on chiral phase to yield 4-chloro-3-cyclopropyl-N-{(3R,4S)-4-(3,4-dichloro-phenyl)-1-[1-(1-methyl-cyclopropanecarbonyl)-piperidine-4-carbonyl]-pyrrolidin-3-yl}-N-methyl-benzamide (MS (m/e): 616.5 [M]$^+$) as a light brown oil and 4-chloro-3-cyclopropyl-N-{(3S,4R)-4-(3,4-dichloro-phenyl)-1-[1-(1-methyl-cyclopropanecarbonyl)-piperidine-4-carbonyl]-pyrrolidin-3-yl}-N-methyl-benzamide (MS (m/e): 616.5 [M]$^+$) as a light brown oil.

EXAMPLE 177

N-{(3RS,4SR)-4-(3,4-Dichloro-phenyl)-1-[1-(1-methyl-cyclopropanecarbonyl)-piperidine-4-carbonyl]-pyrrolidin-3-yl}-4,4,4-trifluoro-N-methyl-butyramide

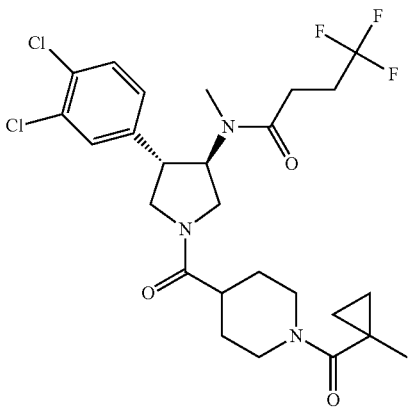 [SMILES: CN(C(=O)CCC(F)(F)F)[C@H]1CN(C(=O)C2CCN(C(=O)C3(C)CC3)CC2)C[C@@H]1c1ccc(Cl)c(Cl)c1]

To a solution of 4,4,4-trifluorobutyric acid (43 mg, 0.304 mmol) in NMP (1 ml) was added at ambient temperature 2-(1H-benzotriazole-1-yl)-1,1,3,3-tetramethyluronium tetrafluoroborate (89 mg, 0.28 mmol) and N,N-diisopropyl ethyl amine (130 µl, 0.760 mmol). After stirring for 15 min a solution {4-[(3SR,4RS)-3-(3,4-dichloro-phenyl)-4-methylamino-pyrrolidine-1-carbonyl]-piperidin-1-yl}-(1-methyl-cyclopropyl)-methanone (111 mg, 0.253 mmol) in NMP (1 mL) was added and stirred for 18 h at ambient temperature. The reaction mixture was diluted with ethyl acetate (15 mL) and washed with aqueous sodium carbonate (1 M, 15 mL), water (15 mL) and brine (15 mL). The aqueous layers were extracted with ethyl acetate (15 mL) and the combined organic layers were dried over sodium sulfate. Purification by chromatography (SiO$_2$, heptane:ethyl acetate:methanol=20:80:0 to 0:85:15) afforded the title compound (109 mg, 77%) as an off-white foam. MS m/e: 562.2 [M]$^+$.

EXAMPLE 178

2-Cyclopropylmethoxy-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-acetamide

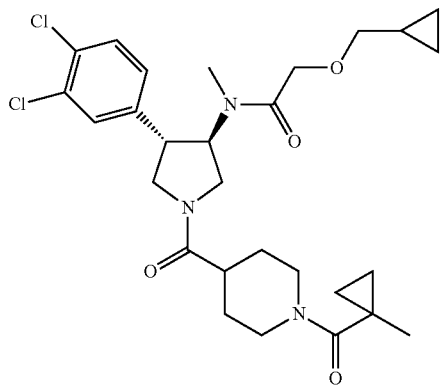 [SMILES: CN(C(=O)COCC1CC1)[C@H]1CN(C(=O)C2CCN(C(=O)C3(C)CC3)CC2)C[C@@H]1c1ccc(Cl)c(Cl)c1]

In analogy to the procedure described for the synthesis of example 177, the title compound 2-cyclopropylmethoxy-N-{(3RS,4SR)-4-(3,4-dichloro-phenyl)-1-[1-(1-methyl-cyclopropanecarbonyl)-piperidine-4-carbonyl]-pyrrolidin-3-yl}-N-methyl-acetamide was prepared from {4-[(3SR,4RS)-3-(3,4-dichloro-phenyl)-4-methylamino-pyrrolidine-1-carbonyl]-piperidin-1-yl}-(1-methyl-cyclopropyl)-methanone using Cyclopropylmethoxy-acetic acid instead of 4,4,4-trifluorobutyric acid and was obtained as an off-white foam. MS m/e: 550.2 [M]$^+$.

The invention claimed is:
1. A compound of formula IA

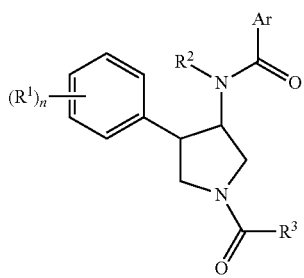

wherein
R$^1$ is hydrogen or halogen; n is 1 or 2;
R$^2$ is lower alkyl;
R$^3$ is

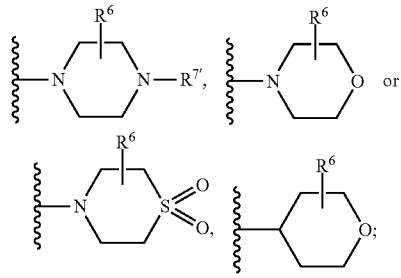

R$^6$ is hydrogen, lower alkyl or hydroxy;
R$^{7'}$ is hydrogen, lower alkyl, S(O)$_2$-lower alkyl, —C(O)-lower alkyl, —C(O)CH$_2$—O-lower alkyl, —CH$_2$CN, —C(O)CN, —C(O)CH$_2$CN, —C(O)-cycloalkyl wherein the cycloalkyl group is optionally substituted by cyano, lower alkyl, one or two halogen atoms, =O or amino, or is —C(O)O-lower alkyl or —CH$_2$O-lower alkyl; or
Ar is aryl- or heteroaryl, wherein the rings of the aryl or heteroaryl group are optionally substituted by one or two substituents R"; and
R" is selected from hydrogen, halogen, lower alkyl, lower alkyl substituted by halogen, lower alkoxy, lower alkoxy substituted by halogen, —O-CH$_2$-cycloalkyl, —NR$^4$R$^5$, —CN, —CH(CH$_3$)CN, —CH$_2$O-lower alkyl and pyrrolyl;
R$^4$ and R$^5$ are each independently hydrogen, C(O)CF$_3$, or lower alkyl;
or a pharmaceutically active salt, racemic mixture, enantiomer, optical isomer or tautomeric form thereof.
2. A compound of claim 1, selected from the group consisting of
rac-N-[(3S,4R)-4-(3,4-dichloro-phenyl)-1-(4-methanesulfonyl-piperazine-1-carbonyl) -pyrrolidin-3-yl]-4-methoxy-N-methyl-3-trifluoromethyl-benzamide;
rac-4-chloro-N-[(3S,4R)-4-(3,4-dichloro-phenyl)-1-(4-methanesulfonyl-piperazine-1-carbonyl)-pyrrolidin-3-yl]-N-methyl-benzamide;
rac-N-[(3S,4R)-4-(3,4-dichloro-phenyl)-1-(4-methanesulfonyl-piperazine-1-carbonyl) -pyrrolidin-3-yl]-4-ethyl-N-methyl-benzamide;
rac-N-[(3S,4R)-4-(3,4-dichloro-phenyl)-1-(4-methanesulfonyl-piperazine-1-carbonyl) -pyrrolidin-3-yl]-N-methyl-4-trifluoromethoxy-benzamide;
rac-N-[(3S,4R)-4-(3,4-dichloro-phenyl)-1-(4-methanesulfonyl-piperazine-1-carbonyl) -pyrrolidin-3-yl]-3-fluoro-N-methyl-4-trifluoromethyl-benzamide;
rac-N-[(3S,4R)-4-(3,4-dichloro-phenyl)-1-(4-methanesulfonyl-piperazine-1-carbonyl) -pyrrolidin-3-yl]-2-fluoro-N-methyl-3-trifluoromethyl-benzamide;
rac-N-[(3S,4R)-4-(3,4-dichloro-phenyl)-1-(4-methanesulfonyl-piperazine-1-carbonyl) -pyrrolidin-3-yl]-4-dimethylamino-N-methyl-benzamide;
rac-N-[(3S,4R)-4-(3,4-dichloro-phenyl)-1-(4-methanesulfonyl-piperazine-1-carbonyl) -pyrrolidin-3-yl]-4-fluoro-3,N-dimethyl-benzamide;
rac-N-[(3S,4R)-4-(3,4-dichloro-phenyl)-1-(4-methanesulfonyl-piperazine-1-carbonyl) -pyrrolidin-3-yl]-3-fluoro-4-methoxy-N-methyl-benzamide;
rac-2,2-difluoro-benzo[1,3]dioxole-5-carboxylic acid [(3S,4R)-4-(3,4-dichloro-phenyl)-1-(4-methanesulfonyl-piperazine-1-carbonyl)-pyrrolidin-3-yl]-methyl-amide; and
rac-N-[(3S,4R)-4-(3,4-dichloro-phenyl)-1-(4-methanesulfonyl-piperazine-1-carbonyl) -pyrrolidin-3-yl]-N-methyl-4-pyrrol-1-yl-benzamide.
3. A compound of claim 1, selected from the group consisting of rac-3-chloro-N-[(3S,4R)-4-(3,4-dichloro-phenyl)-1-(4-methanesulfonyl-piperazine-1-carbonyl)-pyrrolidin-3-yl]-4-fluoro-N-methyl-benzamide;
rac-3-chloro-N-[(3S,4R)-4-(3,4-dichloro-phenyl)-1-(4-methanesulfonyl-piperazine-1-carbonyl)-pyrrolidin-3-yl]-4-methoxy-N-methyl-benzamide;
rac-N-[(3S,4R)-4-(3,4-dichloro-phenyl)-1-(4-methanesulfonyl-piperazine-1-carbonyl) -pyrrolidin-3-yl]-4-fluoro-N-methyl-3-trifluoromethyl-benzamide;
rac-N-[(3S,4R)-4-(3,4-dichloro-phenyl)-1-(4-methanesulfonyl-piperazine-1-carbonyl) -pyrrolidin-3-yl]-4-methoxy-N-methyl-benzamide;
rac-N-[(3S,4R)-4-(3,4-dichloro-phenyl)-1-(4-methanesulfonyl-piperazine-1-carbonyl) -pyrrolidin-3-yl]-2-fluoro-N-methyl-5-trifluoromethyl-benzamide;
N-[(3S,4R)-4-(3,4-dichloro-phenyl)-1-((S)-4-methanesulfonyl-3-methyl-piperazine-1-carbonyl)-pyrrolidin-3-yl]-4-methoxy-N-methyl-3-trifluoromethyl-benzamide; and
N-[(3S,4R)-4-(3,4-dichloro-phenyl)-1-((R)-4-methanesulfonyl-3-methyl-piperazine-1-carbonyl)-pyrrolidin-3-yl]-4-methoxy-N-methyl-3-trifluoromethyl-benzamide.
4. A compound of formula I, having formula I-1

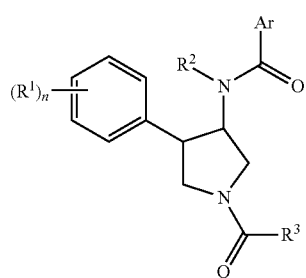

wherein
R$^1$ is hydrogen, halogen, cyano or lower alkyl; n is 1, 2 or 3;
R$^2$ is hydrogen or lower alkyl;

R³ is

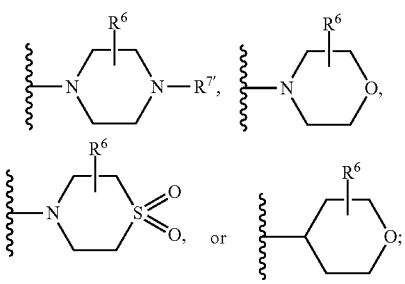

R⁶ is hydrogen, lower alkyl or hydroxy;
R⁷' is hydrogen, lower alkyl, —S(O)₂-lower alkyl, —C(O)-lower alkyl, —C(O)CH₂—O-lower alkyl, —CH₂CN, —C(O)CN, —C(O)CH₂CN, —C(O)-cycloalkyl wherein the cycloalkyl group is optionally substituted by cyano, lower alkyl, one or two halogen atoms, =O or amino, or is —C(O)O-lower alkyl or —CH₂O-lower alkyl; or
Ar is aryl- or heteroaryl, wherein the rings of the aryl or heteroaryl group are optionally substituted by one or two substituents R'';
R'' is selected from hydrogen, halogen, lower alkyl, lower alkyl substituted by halogen, lower alkoxy, lower alkoxy substituted by halogen, —O-CH₂-cycloalkyl, —NR⁴R⁵, —CN, —CH(CH₃)CN, —CH₂O-lower alkyl and pyrrolyl;
R⁴ and R⁵ are each independently hydrogen, —(CO)CF₃ or lower alkyl;
or a pharmaceutically active salt, racemic mixture, enantiomer, optical isomer or tautomeric form thereof.

5. A compound of claim 4, having formula I-11

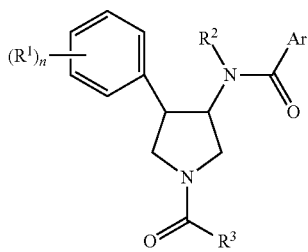

I-11 wherein
R¹ is hydrogen or halogen; n is 1 or 2;
R² is lower alkyl ;
R³ is

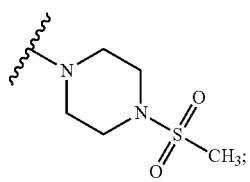 [SMILES: *N1CCN(S(C)(=O)=O)CC1]

Ar is aryl- or heteroaryl, wherein the rings of the aryl or heteroaryl group are optionally substituted by one or two substituents R''; and
R'' is selected from hydrogen, halogen, lower alkyl, lower alkyl substituted by halogen, lower alkoxy, lower alkoxy substituted by halogen, —O-CH₂-cycloalkyl, —NR⁴R⁵, —CN, —CH(CH₃)CN, —CH₂O-lower alkyl and pyrrolyl;
R⁴ and R⁵ are each independently hydrogen or lower alkyl;
or a pharmaceutically active salt, racemic mixture, enantiomer, optical isomer or tautomeric form thereof.

6. A compound of claim 4, having formula I-12

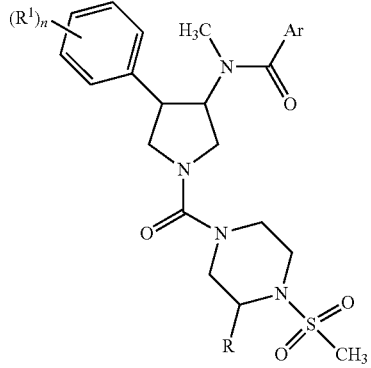

I-12 wherein
R¹ is hydrogen or halogen; n is 1 or 2;
R² is lower alkyl ;
Ar is aryl- or heteroaryl, wherein the rings of the aryl or heteroaryl group are optionally substituted by one or two substituents R''; and
R'' is selected from hydrogen, halogen, lower alkyl, lower alkyl substituted by halogen, lower alkoxy, lower alkoxy substituted by halogen, —O-CH₂-cycloalkyl, —NR⁴R⁵, —CN, —CH(CH₃)CN, —CH₂O-lower alkyl and pyrrolyl;
R⁴ and R⁵ are each independently hydrogen or lower alkyl;
or a pharmaceutically active salt, racemic mixture, enantiomer, optical isomer or tautomeric form thereof.

7. A compound of claim 1, selected from the group consisting of
rac-N-[(3S,4R)-1-(4-Methanesulfonyl-piperazine-1-carbonyl)-4-phenyl-pyrrolidin-3-yl]-N -methyl-3,5-bis-trifluoromethyl-benzamide;
rac-N-[(3S,4R)-1-(4-Methanesulfonyl-piperazine-1-carbonyl)-4-phenyl-pyrrolidin-3-yl]-N -methyl-4-trifluoromethyl-benzamide;
rac-4-Dimethylamino-N-[(3S,4R)-1-(4-methanesulfonyl-piperazine-1-carbonyl)-4-phenyl -pyrrolidin-3-yl]-N-methyl-benzamide;
rac-N-[(3S,4R)-1-(4-Methanesulfonyl-piperazine-1-carbonyl)-4-phenyl-pyrrolidin-3-yl]-4-methoxy-N-methyl-3-trifluoromethyl-benzamide;
rac-3,5-Dichloro-N-[(3S,4R)-1-(4-methanesulfonyl-piperazine-1-carbonyl)-4-phenyl -pyrrolidin-3-yl]-N-methyl-benzamide;
rac-N-[(3S,4R)-4-(4-Chloro-phenyl)-1-(4-methanesulfonyl-piperazine-1-carbonyl) -pyrrolidin-3-yl]-4-methoxy-N-methyl-3-trifluoromethyl-benzamide;
rac-N-[(3S,4R)-4-(4-Chloro-phenyl)-1-(4-methanesulfonyl-piperazine-1-carbonyl) -pyrrolidin-3-yl]-N-methyl-3-trifluoromethyl-benzamide;
rac-N-[(3S,4R)-4-(3,4-Dichloro-phenyl)-1-(4-methanesulfonyl-piperazine-1-carbonyl) -pyrrolidin-3-yl]-N-methyl-benzamide;
rac-N-[(3S,4R)-4-(3,4-Dichloro-phenyl)-1-(4-methanesulfonyl-piperazine-1-carbonyl) -pyrrolidin-3-yl]-4-fluoro-N-methyl-benzamide; and rac-3-Chloro-N-[(3S,4R)-4-(3,4-dichloro-phenyl)-1-(4-methanesulfonyl-piperazine-1-carbonyl)-pyrrolidin-3-yl]-N-methyl-benzamide.

8. A compound of claim 1, selected from the group consisting of rac-4-Cyano-N-[(3S,4R)-4-(3,4-dichloro-phenyl)-1-(4-methanesulfonyl-piperazine-1-carbonyl)-pyrrolidin-3-yl]-N-methyl-benzamide;

rac-3-Cyano-N-[(3S,4R)-4-(3,4-dichloro-phenyl)-1-(4-methanesulfonyl-piperazine-1-carbonyl)-pyrrolidin-3-yl]-N-methyl-benzamide;

rac-N-[(3S,4R)-4-(3,4-Dichloro-phenyl)-1-(4-methane-sulfonyl-piperazine-1-carbonyl)-pyrrolidin-3-yl]-3-fluoro-N-methyl-5-trifluoromethyl-benzamide;

rac-N-[(3S,4R)-4-(3,4-Dichloro-phenyl)-1-(4-methane-sulfonyl-piperazine-1-carbonyl)-pyrrolidin-3-yl]-3,5-difluoro-N-methyl-benzamide;

rac-N-[(3S,4R)-4-(3,4-Dichloro-phenyl)-1-(4-methane-sulfonyl-piperazine-1-carbonyl)-pyrrolidin-3-yl]-3-fluoro-N-methyl-4-trifluoromethyl-benzamide;

rac-3-Chloro-N-[(3S,4R)-4-(3,4-dichloro-phenyl)-1-(4-methanesulfonyl-piperazine-1-carbonyl)-pyrrolidin-3-yl]-2-fluoro-N-methyl-benzamide;

rac-Benzofuran-5-carboxylic acid [(3S,4R)-4-(3,4-dichloro-phenyl)-1-(4-methanesulfonyl-piperazine-1-carbonyl)-pyrrolidin-3-yl]-methyl-amide;

rac-N-[(3S,4R)-4-(3,4-Dichloro-phenyl)-1-(4-methane-sulfonyl-piperazine-1-carbonyl)-pyrrolidin-3-yl]-3,4-difluoro-N-methyl-benzamide;

rac-N-[(3S,4R)-4-(3,4-Dichloro-phenyl)-1-(4-methane-sulfonyl-piperazine-1-carbonyl)-pyrrolidin-3-yl]-N-methyl-4-(2,2,2-trifluoro-acetylamino)-benzamide; and rac-2,3-Dihydro-benzofuran-5-carboxylic acid [(3S,4R)-4-(3,4-dichloro-phenyl)-1-(4-methanesulfonyl-piperazine-1-carbonyl)-pyrrolidin-3-yl]-methyl-amide.

9. A compound of claim 1, selected from the group consisting of rac-Quinoxaline-6-carboxylic acid [(3S,4R)-4-(3,4-dichloro-phenyl)-1-(4-methanesulfonyl-piperazine-1-carbonyl)-pyrrolidin-3-yl]-methyl-amide;

rac-3-(Cyano-methyl-methyl)-N-[(3S,4R)-4-(3,4-dichloro-phenyl)-1-(4-methanesulfonyl-piperazine-1-carbonyl)-pyrrolidin-3-yl]-N-methyl-benzamide; and rac-N-[(3S,4R)-4-(3,4-Dichloro-phenyl)-1-(4-methane-sulfonyl-piperazine-1-carbonyl)-pyrrolidin-3-yl]-N-ethyl-2-fluoro-5-trifluoromethyl-benzamide.

10. A pharmaceutical composition comprising a compound of formula IA

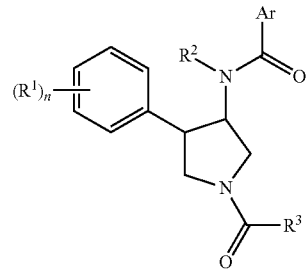

wherein
$R^1$ is hydrogen or halogen; n is 1 or 2 ;
$R^2$ is lower alkyl;
$R^3$ is

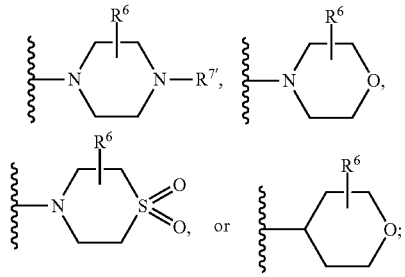

$R^6$ is hydrogen, lower alkyl or hydroxy;
$R^{7'}$ is hydrogen, lower alkyl, —S(O)$_2$-lower alkyl, —C(O)-lower alkyl, —C(O)CH$_2$—O-lower alkyl, —CH$_2$CN, —C(O)CN, —C(O)CH$_2$CN, —C(O)-cycloalkyl wherein the cycloalkyl group is optionally substituted by cyano, lower alkyl, one or two halogen atoms, =O or amino, or is —C(O)O-lower alkyl or —CH$_2$O-lower alkyl; or
Ar is aryl- or heteroaryl, wherein the rings of the aryl or heteroaryl group are optionally substituted by one or two substituents R";
R" is selected from hydrogen, halogen, lower alkyl, lower alkyl substituted by halogen, lower alkoxy, lower alkoxy substituted by halogen, —O—CH$_2$-cycloalkyl, —NR$^4$R$^5$, —CN, —CH(CH$_3$)CN, —CH$_2$O-lower alkyl and pyrrolyl;
$R^4$ and $R^5$ are each independently hydrogen, —(CO)CF$_3$ or lower alkyl;
or a pharmaceutically active salt, racemic mixture, enantiomer, optical isomer or tautomeric form thereof and a pharmaceutically acceptable carrier.

* * * * *